(12) United States Patent
Lee et al.

(10) Patent No.: US 10,174,000 B2
(45) Date of Patent: Jan. 8, 2019

(54) BICYCLIC-FUSED HETEROARYL OR ARYL COMPOUNDS AS IRAK4 MODULATORS

(71) Applicant: PFIZER INC., New York, NY (US)

(72) Inventors: Katherine Lin Lee, West Newton, MA (US); Christophe Philippe Allais, Ledyard, CT (US); Christoph Martin Dehnhardt, Burnaby (CA); Lori Krim Gavrin, Villanova, PA (US); Seungil Han, Mystic, CT (US); David Hepworth, Concord, MA (US); Arthur Lee, Littleton, MA (US); Frank Eldridge Lovering, Acton, MA (US); John Paul Mathias, Concord, MA (US); Dafydd Rhys Owen, Concord, MA (US); Nikolaos Papaioannou, Newton, MA (US); Eddine Saiah, Brookline, MA (US); Joseph Walter Strohbach, Wentzville, MO (US); John David Trzupek, Arlington, VA (US); Stephen Wayne Wright, Old Lyme, CT (US); Christoph Wolfgang Zapf, Marlborough, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/754,650

(22) PCT Filed: Aug. 16, 2016

(86) PCT No.: PCT/IB2016/054906
§ 371 (c)(1),
(2) Date: Feb. 23, 2018

(87) PCT Pub. No.: WO2017/033093
PCT Pub. Date: Mar. 2, 2017

(65) Prior Publication Data
US 2018/0244646 A1    Aug. 30, 2018

Related U.S. Application Data

(60) Provisional application No. 62/210,573, filed on Aug. 27, 2015.

(51) Int. Cl.
*C07D 207/273* (2006.01)
*C07D 401/12* (2006.01)
*C07D 401/14* (2006.01)
*C07D 413/04* (2006.01)
*C07D 413/14* (2006.01)
*C07D 471/04* (2006.01)
*C07D 491/18* (2006.01)
*A61K 31/4015* (2006.01)
*A61K 31/4375* (2006.01)
*A61K 31/4709* (2006.01)
*A61K 31/4725* (2006.01)
*A61K 31/4745* (2006.01)
*A61K 45/06* (2006.01)

(52) U.S. Cl.
CPC ........ *C07D 401/12* (2013.01); *A61K 31/4015* (2013.01); *A61K 31/4375* (2013.01); *A61K 31/4709* (2013.01); *A61K 31/4725* (2013.01); *A61K 31/4745* (2013.01); *A61K 45/06* (2013.01); *C07D 207/273* (2013.01); *C07D 401/14* (2013.01); *C07D 413/04* (2013.01); *C07D 413/14* (2013.01); *C07D 471/04* (2013.01); *C07D 491/18* (2013.01)

(58) Field of Classification Search
None
See application file for complete search history.

(56) References Cited

U.S. PATENT DOCUMENTS

2013/0029949 A1    1/2013    Hoffman et al.

FOREIGN PATENT DOCUMENTS

WO    2015/150995    10/2015

OTHER PUBLICATIONS

Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders", J. Med. Chem., vol. 58(1), pp. 96-110 (2015).
Tumey et al., "Identification and optimization of indolo[2,3-c]quinoline inhibitors of IRAK4", Bioorganic & Medicinal Chemistry Letters, vol. 24(9), pp. 2066-2072 (2014).
Seganish, "Inhibitors of interleukin-1 receptor-associated kinase 4 (IRAK4): a patent review (2012-2015)", Exp. Opin. on Therapeutic Patents, vol. 26(8), pp. 917-932 (2016).

*Primary Examiner* — Alicia L Otton
(74) *Attorney, Agent, or Firm* — James T. Wasicak

(57) ABSTRACT

Compounds, tautomers and pharmaceutically acceptable salts of the compounds are disclosed, wherein the compounds have the structure of Formula Ia, as defined in the specification. Corresponding pharmaceutical compositions, methods of treatment, methods of synthesis, and intermediates are also disclosed.

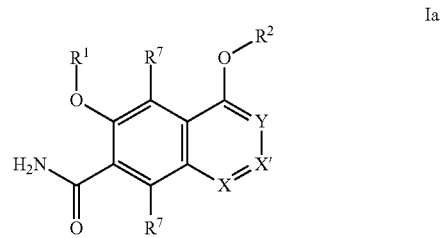

Ia

10 Claims, No Drawings

BICYCLIC-FUSED HETEROARYL OR ARYL COMPOUNDS AS IRAK4 MODULATORS

FIELD OF THE INVENTION

This invention pertains to compounds useful for the treatment of autoimmune and inflammatory diseases associated with Interleukin-1 Receptor Associated Kinase (IRAK) and more particularly compounds that modulate the function of IRAK4.

BACKGROUND OF THE INVENTION

Protein kinases are families of enzymes that catalyze the phosphorylation of specific residues in proteins, broadly classified in tyrosine and serine/threonine kinases. Inappropriate activity arising from dysregulation of certain kinases by a variety of mechanisms is believed to underlie the causes of many diseases, including but not limited to, cancer, cardiovascular diseases, allergies, asthma, respiratory diseases, autoimmune diseases, inflammatory diseases, bone diseases, metabolic disorders, and neurological and neurodegenerative diseases. As such, potent and selective inhibitors of kinases are sought as potential treatments for a variety of human diseases.

There is considerable interest in targeting the innate immune system in the treatment of autoimmune diseases and sterile inflammation. Receptors of the innate immune system provide the first line of defense against bacterial and viral insults. These receptors recognize bacterial and viral products as well as pro-inflammatory cytokines and thereby initiate a signaling cascade that ultimately results in the up-regulation of inflammatory cytokines such as TNFα, IL6, and interferons. Recently it has become apparent that self-generated ligands such as nucleic acids and products of inflammation such as high-mobility group protein B1 (HMGB1) and Advanced Glycated End-products (AGE) are ligands for Toll-like receptors (TLRs) which are key receptors of the innate immune system (O'Neill 2003, Kanzler et al., 2007, Wagner 2006). This demonstrates the role of TLRs in the initiation and perpetuation of inflammation due to autoimmunity.

Interleukin-1 receptor associated kinase 4 (IRAK4) is a ubiquitously expressed serine/threonine kinase involved in the regulation of innate immunity (Suzuki & Saito 2006). IRAK4 is responsible for initiating signaling from TLRs and members of the IL-1/18 receptor family. Kinase-inactive knock-ins and targeted deletions of IRAK4 in mice were reported to cause reductions in TLR and IL-1 induced pro-inflammatory cytokines (Kawagoe et al., 2007; Fraczek et al., 2008; Kim et al., 2007). IRAK4 kinase-dead knock-in mice have also been shown to be resistant to induced joint inflammation in the antigen-induced-arthritis (AIA) and serum transfer-induced (K/BxN) arthritis models (Koziczak-Holbro 2009). Likewise, humans deficient in IRAK4 also appear to display the inability to respond to challenge by Toll ligands and IL-1 (Hernandez & Bastian 2006). However, the immunodeficient phenotype of IRAK4-null individuals is narrowly restricted to challenge by gram positive bacteria, but not gram negative bacteria, viruses or fungi. This gram positive sensitivity also lessens with age, implying redundant or compensating mechanisms for innate immunity in the absence of IRAK4 (Lavine et al., 2007).

These data indicate that inhibitors of IRAK4 kinase activity should have therapeutic value in treating cytokine driven autoimmune diseases while having minimal immunosuppressive side effects. Additional recent studies suggest that targeting IRAK4 may be useful in other inflammatory pathologies such as atherosclerosis and diffuse large B-cell lymphoma (Rekhter et al., 2008; Ngo et al., 2011). Therefore, inhibitors of IRAK4 kinase activity are potential therapeutics for a wide variety of diseases including but not limited to autoimmunity, inflammation, cardiovascular diseases, cancer, and metabolic diseases. See the following references for additional information. N. Suzuki and T. Saito, *Trends in Immunology*, 2006, 27, 566. T. Kawagoe, S. Sato, A. Jung, M. Yamamoto, K. Matsui, H. Kato, S. Uematsu, O. Takeuchi and S. Akira, *Journal of Experimental Medicine*, 2007, 204, 1013. J. Fraczek, T. W. Kim, H. Xiao, J. Yao, Q. Wen, Y. Li, J.-L. Casanova, J. Pryjma and X. Li, *Journal of Biological Chemistry*, 2008, 283, 31697. T. W. Kim, K. Staschke, K. Bulek, J. Yao, K. Peters, K.-H. Oh, Y. Vandenburg, H. Xiao, W. Qian, T. Hamilton, B. Min, G. Sen, R. Gilmour and X. Li, *Journal of Experimental Medicine*, 2007, 204, 1025. M. Koziczak-Holbro, A. Littlewood-Evans, B. Pollinger, J. Kovarik, J. Dawson, G. Zenke, C. Burkhart, M. Muller and H. Gram, *Arthritis & Rheumatism*, 2009, 60, 1661. M. Hernandez and J. F. Bastian, *Current Allergy and Asthma Reports*, 2006, 6, 468. E. Lavine, R. Somech, J. Y. Zhang, A. Puel, X. Bossuyt, C. Picard, J. L. Casanova and C. M. Roifman, *Journal of Allergy and Clinical Immunology*, 2007, 120, 948. M. Rekhter, K. Staschke, T. Estridge, P. Rutherford, N. Jackson, D. Gifford-Moore, P. Foxworthy, C. Reidy, X.-d. Huang, M. Kalbfleisch, K. Hui, M.-S. Kuo, R. Gilmour and C. J. Vlahos, *Biochemical and Biophysical Research Communications*, 2008, 367, 642. O'Neill, L. A. (2003). "Therapeutic targeting of Toll-like receptors for inflammatory and infectious diseases." *Curr Opin Pharmacol* 3(4): 396. Kanzler, H et al., (2007) "Therapeutic targeting of innate immunity with toll-like receptor agonists and antagonists." *Nature Medicine* 13:552. Wagner, H. (2006) "Endogenous TLR ligands and autoimmunity" *Advances in Immunol* 91: 159. Ngo, V. N. et al., (2011) "Oncogenically active MyD88 mutations in human lymphoma" *Nature* 470: 115.

Co-pending U.S. patent application Ser. No. 14/678,114, filed by Pfizer Inc on Apr. 3, 2015, and U.S. Provisional Application 62/204,521, filed on Aug. 13, 2015, describe IRAK4 inhibitors and are hereby incorporated by reference in their entirety for all purposes.

SUMMARY OF THE INVENTION

The invention provides for compounds of the Formula I,

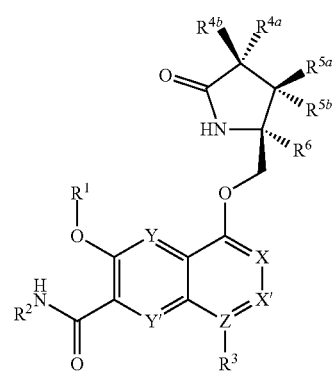

wherein

X, X', Y and Y' are each independently CH or N; Z is C or N; provided that no more than three of X, X', Z, Y and Y' are N;

$R^1$ is $C_1$-$C_6$alkyl or —($C_1$-$C_6$alkyl)$_n$($C_1$-$C_6$cycloalkyl), wherein the alkyl or cycloalkyl is optionally substituted with deuterium, halogen, CN, OH, or $C_1$-$C_6$ alkoxy;

$R^2$ is hydrogen or methyl;

$R^3$ is hydrogen, deuterium, halogen, nitrile, —(CH$_2$)$_t$NR$^{8a}$R$^{8b}$, —(CH$_2$)$_t$(6- to 10-membered aryl) or a —(CH$_2$)$_t$(5- to 10-membered heteroaryl), having one to three heteroatoms selected from N, O or S, wherein said aryl or heteroaryl are optionally substituted by one to three $C_1$-$C_6$alkyl, deuterium, halogen, CN, OH, hydroxyC$_1$-$C_6$alkyl, or $C_1$-$C_6$ alkoxy; wherein the alkyl is optionally substituted with hydroxyl, halogen, CN or $C_1$-$C_3$alkoxy;

$R^{4a}$ and $R^{4b}$ are each independently hydrogen, fluorine, OH, $C_1$-$C_3$ alkoxy, or CH$_2$OR$^7$, wherein $R^7$ taken together with $R^1$ is a $C_1$-$C_4$ alkylene, optionally substituted with halogen or alkyl;

$R^{5a}$ and $R^{5b}$ are each independently hydrogen, $C_1$-$C_3$ alkyl, or $C_1$-$C_3$-alkoxy, wherein said alkyl or alkoxy is optionally substituted with one to three deuterium, halogen, OH or CN; or $R^{5a}$ and $R^{5b}$ taken together with the atom to which they are bonded form a $C_3$-$C_7$ cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl;

$R^6$ is hydrogen or $C_1$-$C_3$ alkyl; or $R^{5b}$ and $R^6$ taken together with the atoms to which they are bonded form a $C_3$-$C_7$cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl;

$R^{8a}$ and $R^{8b}$ are each independently hydrogen, —S(O)$_2$R$^9$ or —C(O)R$^9$;

$R^9$ is $C_1$-$C_6$alkyl, $C_1$-$C_6$cycloalkyl, 6- to 10-membered aryl, or a 5- to 10-membered heteroaryl, having one to three heteroatoms, wherein said alkyl, cycloalkyl, aryl or heteroaryl is optionally substituted by one to three $C_1$-$C_6$alkyl, halogen, CN, OH, $C_1$-$C_6$ alkoxy or $C_1$-$C_6$ hydroxy;

n is 0 or 1;

t is 0, 1, 2 or 3;

or a pharmaceutically acceptable salt of said compound or a tautomer of said compound or said salt.

The invention also provides for pharmaceutical compositions comprising the compounds, methods of using the compounds, combination therapies utilizing the compounds and other therapeutic agents and methods of preparing the compounds. The invention also provides for intermediates useful in the preparation of the compounds of the invention.

In particular, novel bicyclic kinase enzyme inhibitor compounds of Formula I of the present invention possess a therapeutic role of inhibiting IRAK4 useful in the area of diseases and/or disorders that include, but are not limited to, cancers, allergic diseases, autoimmune diseases, inflammatory diseases and/or disorders and/or conditions associated with inflammation and pain, proliferative diseases, hematopoietic disorders, hematological malignancies, bone disorders, fibrosis diseases and/or disorders, metabolic disorders, muscle diseases and/or disorders, respiratory diseases, pulmonary disorders, genetic development diseases, neurological and neurodegenerative diseases and/or disorders, chronic inflammatory demyelinating neuropathies, cardiovascular, vascular or heart diseases, ophthalmic/ocular diseases, wound repair, infection and viral diseases. Therefore, inhibition of IRAK4 would have the potential for multiple therapeutic indications over a wide range of unmet needs.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

All patents, patent applications and references referred to herein are hereby incorporated by reference in their entirety.

Other features and advantages of this invention will be apparent from this specification and the appendent claims which describe the invention. There are many features of this invention that are not necessarily fully captured by the claims. It is understood, however, that all such novel subject matter is part of the invention.

Definitions

Unless otherwise defined herein, scientific and technical terms used in connection with the present invention have the meaning commonly understood by those of ordinary skill in the art. As used in the specification and the appended claims, the singular forms "a", "an", and "the" include plural referents unless the context clearly dictates otherwise.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated require a tighter range.

The term "alkyl" refers to a linear or branched saturated hydrocarbon moiety, consisting solely of carbon and hydrogen atoms. In one embodiment from one to six carbon atoms; and in another embodiment from one to four carbon atoms; and in another embodiment one to three carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like. As appropriate, an alkyl may be optionally substituted at each carbon as defined in the claims. Typical substitution includes, but is not limited to, fluoro, chloro, OH, cyano, alkyl (optionally substituted), cycloalkyl and the like.

In some instances, the number of carbon atoms in a hydrocarbon substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$-cycloalkyl or $C_{3-6}$-cycloalkyl refers to saturated cycloalkyl containing from 3 to 6 carbon ring atoms.

Unless otherwise indicated, "alkylene," by itself or as part of another term, refers to a saturated, branched or straight chain or cyclic hydrocarbon diradical of the stated number of carbon atoms, typically 1-6 carbon atoms, and having two monovalent radical centers derived by the removal of two hydrogen atoms from the same or two different carbon atoms of a parent alkane. Typical alkylene radicals include, but are not limited to methylene (—CH$_2$—), 1,2-ethylene (—CH$_2$CH$_2$—), 2,2-dimethylene, 1,3-propylene (—CH$_2$CH$_2$CH$_2$—), 2-methylpropylene, 1,4-butylene (—CH$_2$CH$_2$CH$_2$CH$_2$—), and the like; optionally substituted, as appropriate, by 1 to 5 suitable substituents as defined above such as fluoro, chloro, deuteron, cyano, trifluoromethyl, (C$_1$-C$_6$)alkoxy, (C$_6$-C$_{10}$)aryloxy, trifluoromethoxy, difluoromethoxy or (C$_1$-C$_6$)alkyl. When the compounds of the invention contain a C$_{2-6}$alkenyl group, the compound may exist as the pure E (entgegen) form, the pure Z (zusammen) form, or any mixture thereof.

"Alkylidene" or "alkenyl" refers to a divalent group formed from an alkane by removal of two hydrogen atoms from the same carbon atom, the free valencies of which are part of a double bond, optionally substituted as described herein. The term alkylidene also includes "allenes" wherein one carbon atom has double bonds with each of its two adjacent carbon centers, such as, for example, propadiene. As appropriate, an alkenyl may be optionally substituted at each carbon as defined in the claims, optionally substituted, as appropriate, by 1 to 5 suitable substituents as defined above and herein such as fluoro, chloro, deutero, cyano, trifluoromethyl, (C$_1$-C$_6$)alkoxy, (C$_6$-C$_{10}$)aryloxy, trifluoromethoxy, difluoromethoxy or (C$_1$-C$_6$)alkyl.

"Alkynyl" refers to an aliphatic hydrocarbon having at least one carbon-carbon triple bond, including straight chain, branched chain or cyclic groups having at least one carbon-carbon triple bond, optionally substituted as described herein. Preferably, it is a lower alkynyl having 2 to 6 carbon atoms. For example, as used herein, the term "C$_{2-6}$alkynyl" is used herein to mean a straight or branched hydrocarbon chain alkynyl radical as defined above having 2 to 6 carbon atoms and one triple bond. As appropriate, an alkynyl may be optionally substituted at each carbon as defined in the claims. Typical substitution includes, but is not limited to, optionally substituted, as appropriate, by 1 to 5 suitable substituents as defined above and herein, such as fluoro, chloro, deutero, cyano, trifluoromethyl, (C$_1$-C$_6$)alkoxy, (C$_6$-C$_{10}$)aryloxy, trifluoromethoxy, difluoromethoxy or (C$_1$-C$_6$)alkyl.

The term "cycloalkyl" refers to a nonaromatic ring containing 3 to 10 carbons that is fully hydrogenated consisting of mono-, bi- or tricyclic rings. Accordingly, a cycloalkyl may be a single ring, which typically contains from 3 to 7 ring atoms. Examples include, but are not limited to, cyclopropyl, cyclobutyl, cyclopentyl, and cyclohexyl. Alternatively, 2 or 3 rings may be fused together, such as bicyclodecanyl and decalinyl. The term "cycloalkyl" also includes bridged bicycloalkyl systems such as, but not limited to, bicyclo[2.2.1]heptane and bicyclo[1.1.1]pentane. The cycloalkyl group may be optionally substituted as described herein, as appropriate, by 1 to 5 suitable substituents as defined above such as fluoro, chloro, deutero, cyano, trifluoromethyl, (C$_1$-C$_6$)alkoxy, (C$_6$-C$_{10}$)aryloxy, trifluoromethoxy, difluoromethoxy or (C$_1$-C$_6$)alkyl.

The term "heterocycloalkyl" means a monovalent saturated moiety, consisting of one to three rings, incorporating one, two, three or four heteroatoms (selected from N, O or S) and three to 10 carbon atoms. The heterocycloalkyl may be optionally substituted as defined herein. Examples of heterocycloalkyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorphilinylsulfone, dihydroquinolinyl, tetrahydroquinolinyl, tetrahydrisoquinolinyl, and the like. Heterocycloalkyls may be optionally substituted, as appropriate, by 1 to 5 suitable substituents as defined herein such as fluoro, chloro, deutero, cyano, trifluoromethyl, (C$_1$-C$_6$)alkoxy, (C$_6$-C$_{10}$)aryloxy, trifluoromethoxy, difluoromethoxy or (C$_1$-C$_6$)alkyl.

Unless otherwise indicated, the term "heteroalkyl," by itself or in combination with another term, means, unless otherwise stated, a saturated, straight or branched chain hydrocarbon radical consisting of the stated number of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom S may be placed at any position of the heteroalkyl group, including the position at which the alkyl group is attached to the remainder of the molecule. Up to two heteroatoms may be consecutive.

Unless otherwise indicated, the term "heteroalkylene" by itself or as part of another substituent means a divalent group derived from heteroalkyl (as defined above). For heteroalkylene groups, heteroatoms can also occupy either or both of the chain termini.

The term "alkoxy" and "alkyloxy", which may be used interchangeably, refers to a moiety of the formula —OR, wherein R is a straight chain saturated alkyl or branched chain saturated alkyl moiety, as defined herein, bonded through an oxygen atom. The alkoxy group may be optionally substituted as defined herein. Non-limiting examples of such alkoxy groups are methoxy, ethoxy, propoxy, isopropoxy, butoxy, isobutoxy, tertiary butoxy, pentoxy and the like.

The term "aryl" means a carbocyclic aromatic system containing one or two rings wherein such rings may be fused. If the rings are fused, one of the rings must be fully unsaturated and the fused ring(s) may be fully saturated, partially unsaturated or fully unsaturated. The term "fused" means that a second ring is present (i.e., attached or formed) by having two adjacent atoms in common (i.e., shared) with the first ring. The term "fused" is equivalent to the term "condensed". The aryl group may be optionally substituted as defined herein. The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl and 1,2,3,4-tetrahydronaphthalenyl. Aryls may be optionally substituted, as appropriate, by 1 to 5 suitable substituents as defined above such as fluoro, chloro, deutero, cyano, trifluoromethyl, (C$_1$-C$_6$)alkoxy, (C$_6$-C$_{10}$)aryloxy, trifluoromethoxy, difluoromethoxy or (C$_1$-C$_6$)alkyl.

The term "heteroaryl" refers to an aromatic ring structure containing from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered ring substituents such as pyridyl, pyrazyl, pyrimidinyl, and pyridazinyl; and 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring.

Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. The heteroaryl can be optionally substituted, as appropriate, by 1 to 5 suitable substituents as defined herein such as fluoro, chloro, deutero, cyano, trifluoromethyl, $(C_1-C_6)$alkoxy, $(C_6-C_{10})$aryloxy, trifluoromethoxy, difluoromethoxy or $(C_1-C_6)$alkyl.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), and morpholinyl.

The term "heteroaryl" also includes fused ring systems having one or two rings wherein such rings may be fused, wherein fused is as defined above. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "5- to 6-membered heteroaryl" refers to a heteroaryl containing from 5 to 6 atoms, including one or more heteroatoms, in the cyclic moiety of the heteroaryl. The heteroatoms for this invention are selected from nitrogen, oxygen and sulfur.

Compounds of the present invention may contain basic nitrogen atoms (e.g. alkyl amines or heterocycles such as pyridine etc.) which may be converted to N-oxides by treatment with an oxidizing agent (e.g. MCPBA and/or hydrogen peroxides) to afford other compounds of this invention. Thus, all nitrogen-containing compounds that may converted to N-oxide (N→O or —N+—O—) derivatives are part of the invention.

One skilled in the art would appreciate that metabolites may be formed as part of the natural biochemical process of degrading and eliminating the compounds. For example, some compounds of the invention may naturally form an N-oxide, as depicted below in the compound of Formula IIIa and IIIb or in other areas of the compound of Formula Ia. Metabolites such as these or others formed as part of the natural biochemical process are within the scope of the invention.

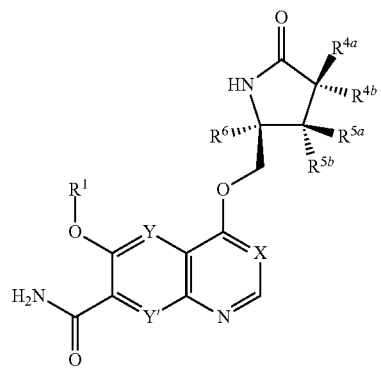

IIIa

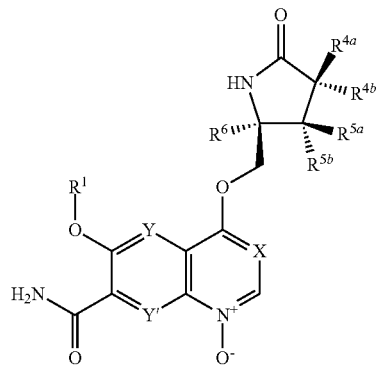

IIIb

If substituents are described as "independently" having more than one variable, each instance of a substituent is selected independent of the other from the list of variables available. Each substituent therefore may be identical to or different from the other substituent(s).

"Patient" or "subject" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

As used herein, the terms "Formula I", "Formula Ia", "Formula IIa-IIy", "Formula IIIa" and "Formula IIIb" may be hereinafter referred to as a "compound(s) of the invention," "the present invention," and collectively the "compound of Formula I." Accordingly, the term "compound of Formula I" includes the compounds of Formula Ia, IIa-IIy, IIIa and IIIb. Such terms are also defined to include all forms of the compound of Formula I, including hydrates, solvates, isomers, crystalline and non-crystalline forms, isomorphs, polymorphs, tautomers and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention have asymmetric carbon atoms. The carbon-carbon bonds of the compounds of the invention may be depicted herein using a solid line (———), a solid wedge (▬▬), or a dotted wedge (╌╌╌). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

Some of the compounds of the invention, such as 23, 27 and 66, may exhibit the phenomenon of tautomerism. For example, the compound exemplified by 23 may exist in several tautomeric forms, including the pyrrolidin-2-one form, Example 23, and the 5-hydroxy-3,4-dihydro-2H-pyrrol form, Example 23a. All such tautomeric forms are included within the scope of the compounds of the Formula I and the scope of the invention. One of ordinary skill in the art would appreciate and recognize that many of the Examples described herein may exhibit tautomerism and are within the scope of the compound of Formula I, Ia, IIa-IIy, IIIa and IIIb. Tautomers exist as mixtures of a tautomeric set in solution. In solid form, usually one tautomer predominates. Even though one tautomer may be described, the present invention includes all tautomers of the compounds of the invention and salts thereof. Examples of tautomers are described by Examples 32 and 32a.

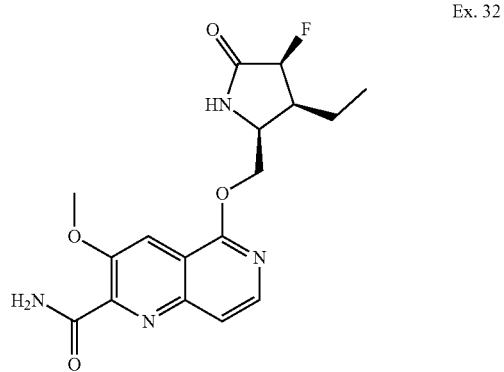

Ex. 32

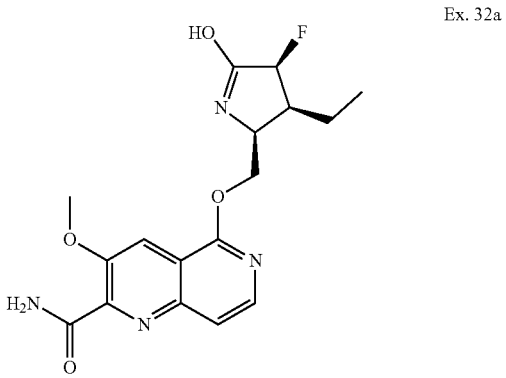

Ex. 32a

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention, which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sulfanilate, cyclohexylaminosulfonate, algenate, p-hydroxybutyrate, galactarate, galacturonate, adipate, alginate, butyrate, camphorate, cam phorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula Ia with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula Ia, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Compounds of the invention as claimed in the claims may specifically define substitution with deutero or deuterium. The absence of the term deuteron, deuteron or deuterium, all of which are used interchangeably, in a substitution group shall not be implied to exclude deutero.

Isotopically labeled compounds of Formula Ia of this invention and prodrugs thereof can generally be prepared by carrying out the procedures disclosed in the Schemes and/or in the Examples and Preparations below, by substituting a readily available isotopically labeled reagent for a non-isotopically labeled reagent.

All patents and publications identified herein are incorporated herein by reference in their entirety and for all purposes.

Compounds of the Invention

In one embodiment, as described above and more fully herein, the invention is directed to a compound of Formula I

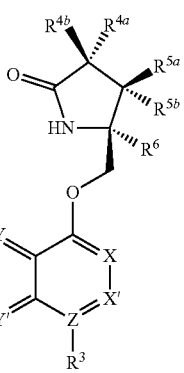

I wherein

X, X', Y and Y' are each independently CH or N; Z is C or N; provided that no more than three of X, X', Z, Y and Y' are N;

$R^1$ is $C_1$-$C_6$alkyl or —$(C_1$-$C_6$alkyl$)_n$($C_1$-$C_6$cycloalkyl), wherein the alkyl or cycloalkyl is optionally substituted with deuterium, halogen, CN, OH, or $C_1$-$C_6$ alkoxy;

$R^2$ is hydrogen or methyl;

$R^3$ is hydrogen, deuterium, halogen, nitrile, —$(CH_2)_t NR^{8a}R^{8b}$, —$(CH_2)_t$(6- to 10-membered aryl) or a —$(CH_2)_t$(5- to 10-membered heteroaryl), having one to three heteroatoms selected from N, O or S, wherein said aryl or heteroaryl are optionally substituted by one to three $C_1$-$C_6$alkyl, deuterium, halogen, CN, OH, hydroxy$C_1$-$C_6$alkyl, or $C_1$-$C_6$ alkoxy; wherein the alkyl is optionally substituted with hydroxyl, halogen, CN or $C_1$-$C_3$alkoxy;

$R^{4a}$ and $R^{4b}$ are each independently hydrogen, fluorine, OH, $C_1$-$C_3$ alkoxy, or $CH_2OR^7$, wherein $R^7$ taken together with $R^1$ is a $C_1$-$C_4$ alkylene, optionally substituted with halogen or alkyl;

$R^{5a}$ and $R^{5b}$ are each independently hydrogen, $C_1$-$C_3$ alkyl, or $C_1$-$C_3$-alkoxy, wherein said alkyl or alkoxy is optionally substituted with one to three deuterium, halogen, OH or CN; or $R^{5a}$ and $R^{5b}$ taken together with the atom to which they are bonded forms a $C_3$-$C_7$ cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl;

$R^6$ is hydrogen or $C_1$-$C_3$ alkyl; or $R^{5b}$ and $R^6$ taken together with the atoms to which they are bonded form a $C_3$-$C_7$cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl $R^{8a}$ and $R^{8b}$ are each independently hydrogen, —$S(O)_2R^9$ or —$C(O)R^9$;

$R^9$ is $C_1$-$C_6$alkyl, $C_1$-$C_6$cycloalkyl, 6- to 10-membered aryl, or a 5- to 10-membered heteroaryl, having one to three heteroatoms, wherein said alkyl, cycloalkyl, aryl or heteroaryl is optionally substituted by one to three $C_1$-$C_6$alkyl, halogen, CN, OH, $C_1$-$C_6$ alkoxy or $C_1$-$C_6$ hydroxy;

n is 0 or 1;

t is 0, 1, 2 or 3;

or a pharmaceutically acceptable salt of said compound or a tautomer of said compound or said salt.

In another embodiment, the invention is directed to compounds wherein X is N, Z is C, X', Y and Y' are CH; alternatively, X' is N, Z is C, X, Y and Y' are CH; alternatively, X, X', Z, Y and Y' are CH; alternatively, Y is N, Z is C, X, X' and Y' are CH; alternatively, Z is C, X and Y' are N, X' and Y are CH; alternatively Z is C, Y' is N, Y, X, and X' are CH; alternatively, X and Z are N, C, X', Y and Y' are CH; alternatively, X' and Z are N, Z is C, X, Y and Y' are CH; alternatively, Z and Y' are N, Y, X, and X' are CH; alternatively, Y and Z are N, X, X' and Y' are CH; alternatively, Z is N, X, X', Y and Y' are CH; or a pharmaceutically acceptable salt of said compound or a tautomer of said compound or said salt.

In another aspect, the invention is directed to a compound of Formula IIa, IIb, IIc, IId, IIe, IIf, IIg, IIh, IIi, IIj, IIk, III, IIm, IIn, IIo, IIp, IIq, IIr, IIs, IIt, IIu, IIv, IIw, IIx or IIy as depicted by the following:

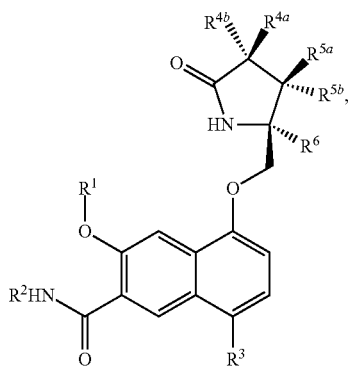

IIa

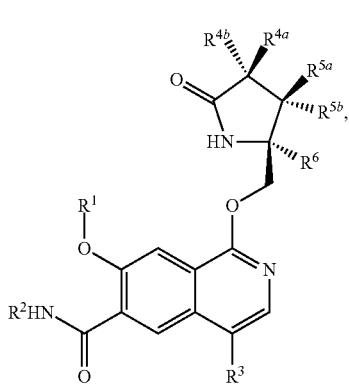

IIb

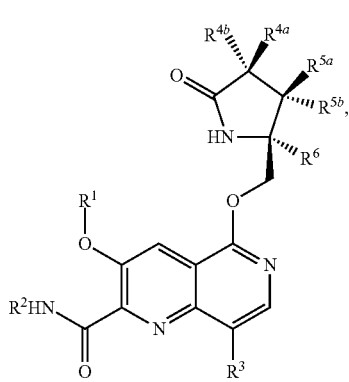

IIc

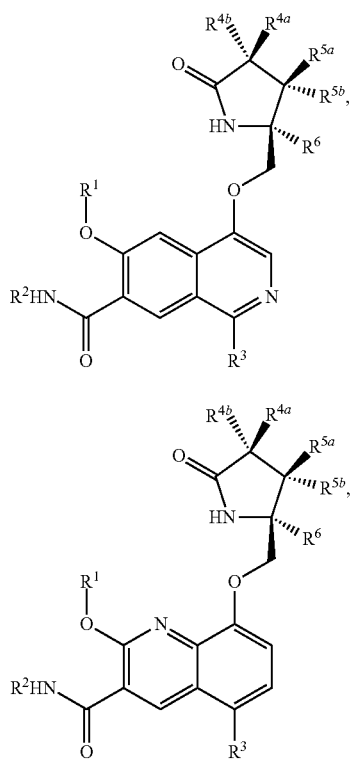
IId
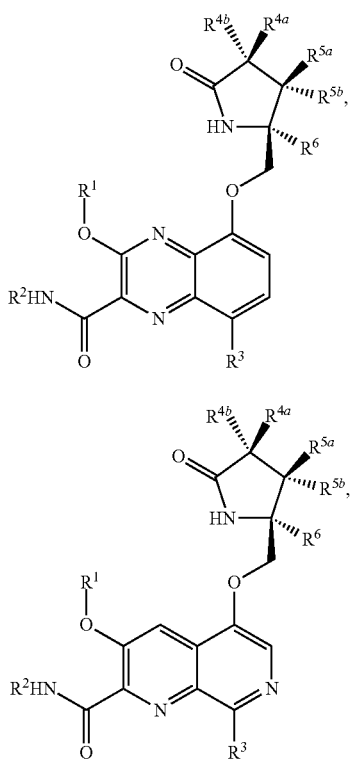
IIh
IIe
IIi
IIf
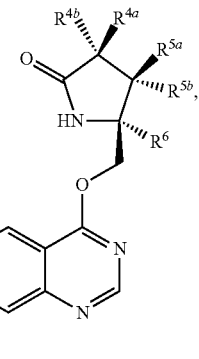
IIj
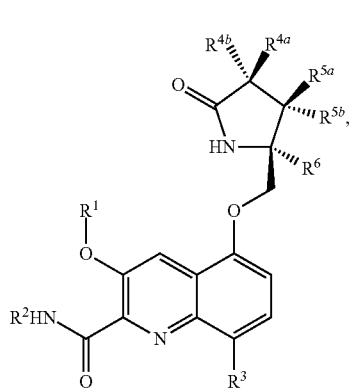
IIg
IIk

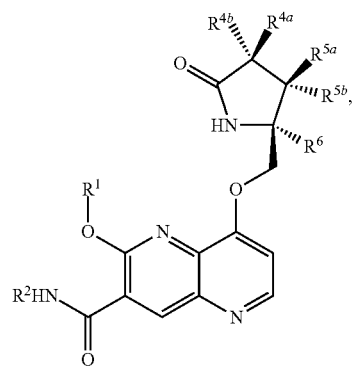
Ill
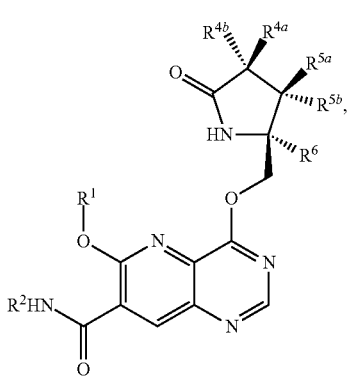
IIm
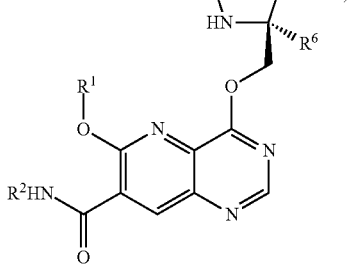
IIn
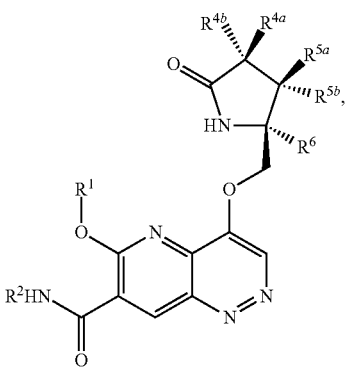 
IIo
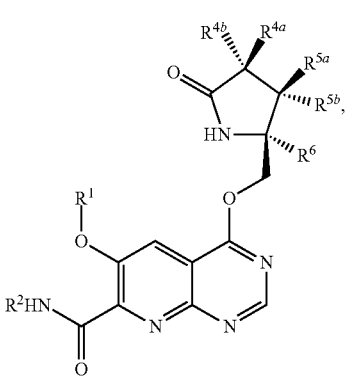
IIp
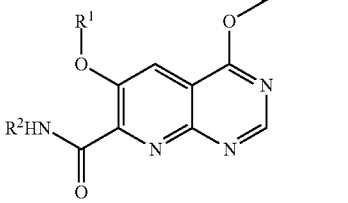
IIq
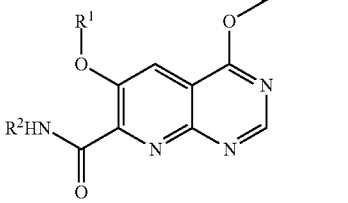
IIr
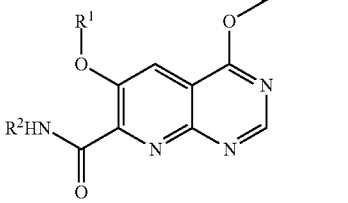
IIs -continued

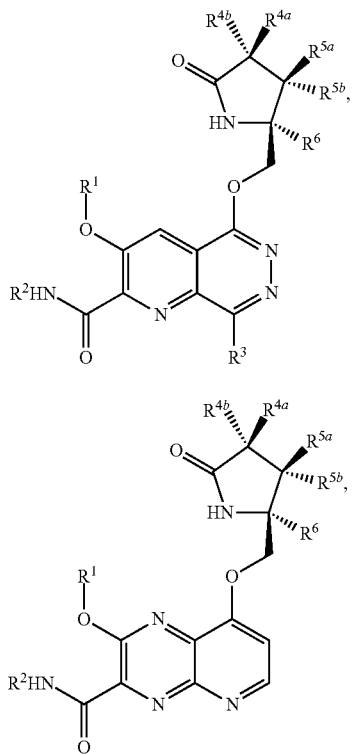

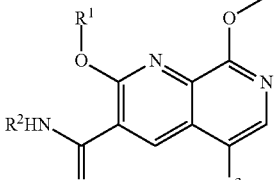

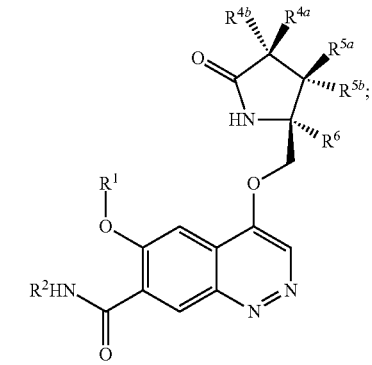

or wherein
R¹ is $C_1$-$C_6$alkyl or —($C_1$-$C_6$alkyl)$_n$($C_1$-$C_6$cycloalkyl), wherein the alkyl or cycloalkyl is optionally substituted with deuterium, halogen, CN, OH, or $C_1$-$C_6$ alkoxy;

R² is hydrogen;

R³ is hydrogen, deuterium, halogen, nitrile, —($CH_2$)$_t$NR$^{8a}$R$^{8b}$, —($CH_2$)$_t$(6- to 10-membered aryl) or a —($CH_2$)$_t$(5- to 10-membered heteroaryl), having one to three heteroatoms selected from N, O or S, wherein said aryl or heteroaryl is optionally substituted by one to three $C_1$-$C_6$alkyl, deuterium, halogen, CN, OH, hydroxy$C_1$-$C_6$ alkyl, or $C_1$-$C_6$ alkoxy;

R$^{4a}$ and R$^{4b}$ are each independently hydrogen, fluorine, OH, $C_1$-$C_3$ alkoxy, or $CH_2OR^7$, wherein R$^7$ taken together with R¹ is a $C_1$-$C_4$alkylene, optionally substituted with halogen or alkyl;

R$^{5a}$ and R$^{5b}$ are independently hydrogen, $C_1$-$C_3$ alkyl, or $C_1$-$C_3$-alkoxy, wherein said alkyl or alkoxy is optionally substituted with one to three deuterium, halogen, OH or CN; or R$^{5a}$ and R$^{5b}$ taken together with the atom to which they are bonded forms a $C_3$-$C_7$cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl;

R⁶ is hydrogen or $C_1$-$C_3$ alkyl; or R$^{5b}$ and R⁶ taken together with the atoms to which they are bonded form a $C_3$-$C_7$cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl;

R$^{8a}$ and R$^{8b}$ are each independently hydrogen, —S(O)$_2$R⁹ or —C(O)R⁹;

R⁹ is $C_1$-$C_6$alkyl, $C_1$-$C_6$cycloalkyl, 6- to 10-membered aryl, or a 5- to 10-membered heteroaryl, having one to three heteroatoms, wherein said alkyl, cycloalkyl, aryl or heteroaryl are optionally substituted by one to three $C_1$-$C_6$alkyl, halogen, CN, OH, $C_1$-$C_6$ alkoxy or $C_1$-$C_6$ hydroxy;

n is 0 or 1; t is 0, 1, 2 or 3.

In another embodiment, $R^1$ is $C_1$-$C_6$alkyl; $R^2$ is hydrogen; $R^3$ is hydrogen, deuterium, —$(CH_2)_tNR^{8a}R^{8b}$, —$(CH_2)_t$(6- to 10-membered aryl) or a —$(CH_2)_t$(5- to 10-membered heteroaryl), having one to three heteroatoms selected from N, O or S, wherein said aryl or heteroaryl is optionally substituted by one to three $C_1$-$C_6$alkyl, deuterium, halogen, CN, OH, hydroxy$C_1$-$C_6$ alkyl or $C_1$-$C_6$ alkoxy;

$R^6$ is hydrogen; $R^{8a}$ and $R^{8b}$ are each independently hydrogen, —$S(O)_2R^9$ or —$C(O)R^9$; $R^9$ is $C_1$-$C_6$alkyl, $C_1$-$C_6$cycloalkyl, 6- to 10-membered aryl, or a 5- to 10-membered heteroaryl, having one to three heteroatoms, wherein said alkyl, cycloalkyl, aryl or heteroaryl are optionally substituted by one to three $C_1$-$C_6$alkyl, halogen, CN, OH, $C_1$-$C_6$ alkoxy or $C_1$-$C_6$ hydroxy; and t is 0 or 1.

In another embodiment, the aryl and heteroaryl of $R^3$ is selected from phenyl, pyrazolyl, imidazolyl and oxazolyl, optionally substituted by one or two $C_1$-$C_6$alkyl or $C_1$-$C_6$hydroxyalkyl; $R^3$ is hydrogen, deuterium or —$(CH_2)_tNR^{8a}R^{8b}$; $R^{8a}$ and $R^{8b}$ are each independently hydrogen or —$S(O)_2R^9$; $R^9$ is $C_1$-$C_6$alkyl, $C_1$-$C_6$cycloalkyl, 6- to 10-membered aryl, or a 5- to 10-membered heteroaryl, having one to three heteroatoms, wherein said alkyl, cycloalkyl, aryl or heteroaryl are optionally substituted by one to three $C_1$-$C_6$alkyl, halogen, CN, OH, $C_1$-$C_6$ alkoxy or $C_1$-$C_6$ hydroxy; and t is 0 or 1.

In another aspect, the invention is directed to a compound selected from

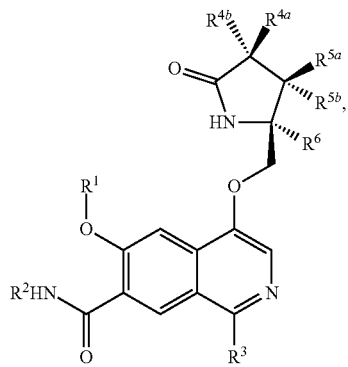

wherein $R^1$ is $C_1$-$C_3$alkyl, is optionally substituted with deuterium or halogen; $R^2$ is hydrogen; $R^3$ is hydrogen, deuterium, —$NH_2$ or a 5- to 10-membered heteroaryl, having one to three heteroatoms selected from N, O or S, wherein said heteroaryl is optionally substituted by one to three $C_1$-$C_6$alkyl, deuterium, halogen, CN, OH or $C_1$-$C_6$ alkoxy; $R^{4a}$ and $R^{4b}$ are each independently hydrogen, fluorine or OH; $R^{5a}$ and $R^{5b}$ are independently hydrogen, $C_1$-$C_3$ alkyl, or $C_1$-$C_3$-alkoxy, wherein said alkyl or alkoxy is optionally substituted with one to three deuterium, halogen, OH or CN; or $R^{5a}$ and $R^{5b}$ taken together with the atom to which they are bonded forms a $C_3$-$C_7$cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl; $R^6$ is hydrogen or $C_1$-$C_3$ alkyl; or $R^{5b}$ and $R^6$ taken together with the atoms to which they are bonded form a $C_3$-$C_7$cycloalkyl or $C_3$-$C_7$heterocycloalkyl, wherein said cycloalkyl or heterocycloalkyl is optionally substituted with one to three deuterium, halogen, OH, CN or $C_1$-$C_3$alkyl; $R^{8a}$ and $R^{8b}$ are each independently hydrogen, —$S(O)_2R^9$ or —$C(O)R^9$; $R^9$ is $C_1$-$C_6$alkyl, $C_1$-$C_6$cycloalkyl, 6- to 10-membered aryl, or a 5- to 10-membered heteroaryl, having one to three heteroatoms, wherein said alkyl, cycloalkyl, aryl or heteroaryl are optionally substituted by one to three $C_1$-$C_6$alkyl, halogen, CN, OH, $C_1$-$C_6$ alkoxy or $C_1$-$C_6$ hydroxy; or a pharmaceutically acceptable salt of said compound or a tautomer of said compound or said salt.

In another embodiment, $R^3$ is hydrogen, —$NH_2$, pyrazolyl, imidazolyl or oxazolyl, wherein said heteroaryls are optionally substituted by one or two $C_1$-$C_3$alkyl; $R^{4a}$ is hydrogen or fluorine; $R^{5a}$ and $R^{5b}$ are independently hydrogen, methyl or ethyl; or $R^{5a}$ and $R^{5b}$ taken together with the atom to which they are bonded forms a cyclopropyl; and $R^6$ is hydrogen.

In another embodiment, $R^{4a}$ and $R^{4b}$ are each independently hydrogen or fluorine; or a pharmaceutically acceptable salt of said compound or a tautomer of said compound or salt. In a further aspect, $R^{4a}$ is fluorine $R^{4b}$ is hydrogen.

In another embodiment, the invention is directed to the compounds of Table I and those which are exemplified herein; or pharmaceutically acceptable salts thereof or tautomers of said compounds or salt.

In another embodiment, the invention is directed to the intermediate compounds described in the Synthetic Schemes and/or Preparations; or a pharmaceutically acceptable salt of said compound or a tautomer of said compound or said salt In another embodiment, the invention is directed to a synthetic process and preparation of the intermediate compounds described herein, as detailed in the Schemes and the preparation section described herein. In another aspect, the invention is directed to a synthetic process and preparation of the compounds of Tables 1 or 3, as detailed in the Schemes and the preparation section described herein.

IRAK4 Indications

The compounds of the invention are also useful in treating and/or preventing a disease or condition mediated by or otherwise associated with an IRAK enzyme; the method comprising administering to a subject in need thereof an effective amount of a compound of the invention.

The disease may be, but not limited to, one of the following classes: auto-immune diseases, inflammatory diseases, allergic diseases, metabolic diseases, infection-based diseases, trauma or tissue-injury based diseases, fibrotic diseases, genetic diseases, diseases driven by over-activity of IL1 pathways, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, bone diseases, and ophthalmic and/or ocular diseases.

Specific autoimmune diseases include, but are not limited to: rheumatoid arthritis, osteoarthritis, psoriasis, allergic dermatitis, systemic lupus erythematosus (and resulting complications), Sjögren's syndrome, multiple sclerosis, asthma, glomerular nephritis, irritable bowel syndrome, inflammatory bowel disease, Crohn's disease, ankylosing spondylitis, Behçet's disease, lupus nephritis, scleroderma, systemic scleroderma, type 1 or juvenile onset diabetes, alopecia universalis, acute disseminated encephalomyelitis, Addison's disease, antiphospholipid antibody syndrome, atrophic gastritis of pernicious anemia, autoimmune alopecia, autoimmune hemolytic anemia, autoimmune hepatitis, autoimmune encephalomyelitis, autoimmune thrombocytopenia, Bullous pemphigoid, Chagas disease, Celiac disease, chronic hepatitis, Cogan's syndrome, dermatomyositis, endometriosis, Goodpasture's syndrome, Graves' disease, Guillain-Barré syndrome, Hashimoto's disease (or Hashimoto's thyroiditis), hemolytic anemia, hidradentitis suppurativa, idiopathic thrombocytopenia purpura, interstitial cystitis, membranous glomerulopathy, morphea, mystenia gravis, narcolepsy, pemphigus, pernicous anemia, polyarteritis nodosa, polymyositis, primary biliary cirrhosis, Reiter's syndrome, schizophrenia, sympathetic opthalmia, systemic sclerosis, temporal arteritis, thyroiditis, vasculitis, vitiglio, vulvodynia, Wegner's granulomatosis, palmoplantar keratoderma, systemic-onset Juvenile Idiopathic Arthritis (SJIA), or an indication listed in a separate category herein.

Specific inflammatory diseases include, but are not limited to: chronic obstructive pulmonary diseases, airway hyper-responsiveness, cystic fibrosis, acute respiratory distress syndrome, sinusitis, rhinitis, gingivitis, atherosclerosis, chronic prostatitis, glomerular nephritis, ulcerative colitis, uveitis, periodontal disease, or an indication listed in a separate category herein.

Specific pain conditions include, but are not limited to: inflammatory pain, surgical pain, visceral pain, dental pain, premenstrual pain, central pain, pain due to burns, migraine or cluster headaches, nerve injury, interstitial cystitis, cancer pain, viral, parasitic or bacterial infection, post-traumatic injury, pain associated with irritable bowel syndrome, gout, pain associated with any of the other indications listed within this specification, or an indication listed in a separate category herein.

Specific respiratory, airway and pulmonary conditions include, but are not limited to: asthma (which may encompass chronic, late, bronchial, allergic, intrinsic, extrinsic or dust), chronic obstructive pulmonary disease, idiopathic pulmonary fibrosis, pulmonary arterial hypertension, cystic fibrosis, interstitial lung disease, acute lung injury, sarcoidosis, allergic rhinitis, chronic cough, bronchitis, recurrent airway obstruction, emphysema, or bronchospasm, or an indication listed in a separate disease category herein.

Specific gastrointestinal (GI) disorders include, but are not limited to: Irritable Bowel Syndrome (IBS), Inflammatory Bowel Disease (IBD), biliary colic and other biliary disorders, renal colic, diarrhea-dominant IBS, pain associated with GI distension, ulcerative colitis, Crohn's Disease, irritable bowel syndrome, Celiac disease, proctitis, eosinophilic gastroenteritis, mastocytosis, or an indication listed in a separate disease category herein.

Specific allergic diseases include, but are not limited to: anaphylaxis, allergic rhinitis, allergic dermatitis, allergic urticaria, angioedema, allergic asthma, allergic reactions to: food, drugs, insect bites, pollen; or an indication listed in a separate disease category herein.

Specific infection-based diseases include, but are not limited to: sepsis, septic shock, viral diseases, malaria, Lyme disease, ocular infections, conjunctivitis, Whipple Disease, or an indication listed in a separate disease category herein.

Specific trauma and tissue injury-based conditions include, but are not limited to: Renal glomerular damage, reperfusion injury (for example to heart, kidney, lung), spinal cord injury, tissue scarring, tissue adhesion, tissue repair, transplant rejection (for examples to heart, lung, bone marrow, cartilage, cornea, kidney, limb, liver, muscle, myoblast, pancreas, pancreatic islet, skin, nerve, small intestine, trachea), hypersensitivities, or an indication listed in a separate disease category herein.

Specific fibrotic diseases include, but are not limited to: Idiopathic pulmonary fibrosis, liver fibrosis, renal fibrosis, or an indication listed in a separate disease category herein.

Specific diseases considered to be driven by over-activity of IL1 pathways include, but are not limited to: Cryopyrin-associated periodic syndromes, myositis, and indications included in the following review article: C. A. Dinarello, A. Simon and J. W. M. van der Meer, Treating inflammation by blocking interleukin-1 in a broad spectrum of diseases, Nat Rev Drug Discov, 2012, 11(8), 633-652, http://dx.doi.org/10.1038/nrd3800 and supplementary information contained therein, or an indication listed in a separate disease category herein.

Specific ophthalmic/ocular diseases include, but are not limited to: uveitis, age-related macular degeneration, diabetic macular edema, keratoconjuctivitis, uveitis associated with Behçet's disease, vernal conjunctivitis, ketatitis, lens-induced uveitis, herpetic keratitis, conical keratitis, corneal epithelial dystrophy, ocular pemphigus, Mooren's ulcer, Scleritis, Graves' ophthalmopathy, Vogt-Koyanagi-Harada syndrome, keratoconjunctivitis sicca, phlyctenule, iridocyclitis, sympathetic ophthalmia, allergic conjunctivitis, ocular neovascularization, dry eye syndrome, or an indication listed in a separate disease category herein.

Specific joint, muscle and bone disorders include, but are not limited to: osteoarthritis, osteoporosis, rheumatoid arthritis, juvenile arthritis, psoriatic arthritis, erosive osteoarthritis of the hand, arthrofibrosis/traumatic knee injury, anterior cruciate knee ligament tear, relapsing polychondritis, recurrent multifocal osteomyelitis, Majeed Syndrome, ankylosing spondylitis, gout of the lumbar spine, antisynthetase syndrome, idiopathic inflammatory myopathies, articular chondrocalcinosis, systemic-onset Juvenile Idiopathic Arthritis (SJIA), gout and pyrophosphate crystal arthritis, or an indication listed in a separate disease category herein.

Specific skin/dermatological diseases include, but are not limited to: psoriasis, atopic dermatitis, cutaneous lupus, acne, dermatomyositis, eczema, pruritus, scleroderma, Sweet Syndrome/neutrophilic dermatosis, neutrophilic panniculitis, acrodermatitis (form of pustular psoriasis), or an indication listed in a separate disease category herein.

Specific renal diseases include, but are not limited to: acute kidney injury (AKI) (sepsis-AKI, coronary artery bypass graft-AKI, cardiac surgery-AKI, non-cardiac surgery-AKI, transplant surgery-AKI cisplatin-AKI, contrast/imaging agent induced-AKI), glomerulonephritis, IgA nephropathy, crescentic GN, lupus nephritis, HIV associated nephropathy, membraneous nephropathy, C3 glomerulopathy, Dense deposit disease, ANCA vasculitis, diabetic nephropathy, hemolytic-uremic syndrome, atypical Hemolytic-uremic syndrome, nephrotic syndrome, nephritic syndrome, hypertensive nephrosclerosis, ApoL1 nephropathy, focal segmental glomerulosclerosis, Alport syndrome, Fanconi, syndrome, crystal nephropathy, nephrolithiasis, nephrotic syndrome, renal transplant rejection, amyloidosis, glomerulonephritis in SJIA, or an indication listed in a separate disease category herein.

Specific genetic diseases include, but are not limited to: Familial Mediterranean fever (FMF), CAPS (FCAS, Muckle-Wells Syndrome, NOMID/CINCA), male hypoinfertility in CAPS, NLRP12 Autoinflammatory Syndrome, or an indication listed in a separate disease category herein.

Specific hematopoietic diseases include, but are not limited to: hemolytic anemia, or an indication listed in a separate disease category herein.

Specific liver diseases include, but are not limited to: liver fibrosis, liver cirrhosis, nonalcoholic steatohepatitis (NASH), or an indication listed in a separate disease category herein.

Specific oral diseases include, but are not limited to: gingivitis, periodontal disease or an indication listed in a separate disease category herein.

Specific metabolic diseases include, but are not limited to: Type 2 diabetes (and resulting complications), gout and hyperuricemia, metabolic syndrome, insulin resistance, obesity, or an indication listed in a separate disease category herein.

Compounds of the current invention are also useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, nonsmall-cell lung carcinoma, lymphomas, Hodgkins and Non-Hodgkins, mammary carcinoma, follicular carcinoma, undifferentiated carcinoma, papillary carcinoma, seminoma, melanoma, smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, intravascular large B-cell lymphoma), or an indication listed in a separate disease category herein.

Cardiovascular conditions include, but are not limited to coronary heart disease, acute coronary syndrome, ischaemic heart disease, first or recurrent myocardial infarction, secondary myocardial infarction, non-ST segment elevation myocardial infarction, or ST segment elevation myocardial infarction, ischemic sudden death, transient ischemic attack, peripheral occlusive arterial disease, angina, atherosclerosis, hypertension, heart failure (such as congestive heart failure), diastolic dysfunction (such as left ventricular diastolic dysfunction, diastolic heart failure, and impaired diastolic filling), systolic dysfunction (such as systolic heart failure with reduced ejection fraction), vasculitis, ANCA vasculitis, post-myocardial infarction cardiac remodeling atrial fibrillation, arrhythmia (ventricular), ischemia, hypertrophic cardiomyopathy, sudden cardiac death, myocardial and vascular fibrosis, impaired arterial compliance, myocardial necrotic lesions, vascular damage, left ventricular hypertrophy, decreased ejection fraction, cardiac lesions, vascular wall hypertrophy, endothelial thickening, fibrinoid necrosis of coronary arteries, adverse remodeling, stroke, and the like, or an indication listed in a separate disease category herein. Also, included are venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

Cardiovascular complications of type 2 diabetes are associated with inflammation, accordingly, the compounds of the present invention may be used to treat diabetes and diabetic complications such as macrovascular disease, hyperglycemia, metabolic syndrome, impaired glucose tolerance, hyperuricemia, glucosuria, cataracts, diabetic neuropathy, diabetic nephropathy, diabetic retinopathy, obesity, dyslipidemia, hypertension, hyperinsulinemia, and insulin resistance syndrome, or an indication listed in a separate disease category herein.

Linkage of innate immunity and inflammation to disease has been demonstrated in neuroinflammatory and neurodegenerative conditions. Therefore, the compounds of the present invention are particularly indicated for use in the treatment of neuroinflammatory and neurodegenerative conditions (i.e., disorders or diseases) in mammals including humans such as multiple sclerosis, migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism), myotrophic lateral sclerosis, chronic fatigue syndrome, or an indication listed in a separate disease category herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88(10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of an IRAK inhibitor compound as provided in the compound of Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal, including a human, in a therapeutically effective amount. By "therapeutically effective amount" it is meant an amount of a compound of the present invention that, when administered alone or in combination with an additional therapeutic agent to a mammal, is effective to treat the desired disease/condition e.g., inflammatory condition such as systemic lupus erythematosus. See also, T. Koutsokeras and T. Healy, Systemic lupus erythematosus and lupus nephritis, *Nat Rev Drug Discov,* 2014, 13(3), 173-174, for therapeutic agents useful treating lupus.

In particular, it is contemplated that the compounds of the invention may be administered with the following therapeutic agents:

Non-steroidal anti-inflammatory drugs (NSAIDs), including but not limited to, non-selective COX1/2 inhibitors such as piroxicam, naproxen, flubiprofen, fenoprofen, ketoprofen, ibuprofen, etodolac (Lodine), mefanamic acid, sulindac, apazone, pyrazolones (such as phenylbutazone), salicylates (such as aspirin); selective COX2 inhibitors such as: celecoxib, rofecoxib, etoricoxib, valdecoxib, meloxicam;

Immunomodulatory and/or anti-inflammatory agents, including but not limited to, methotrexate, leflunomide, ciclesonide chloroquine, hydroxychloroquine, d-penicillamine, auranofin, sulfasalazine, sodium aurothiomalate, cyclosporine, azathioprine, cromolyn, hydroxycarbamide, retinoids, fumarates (such as monomethyl and dimethyl fumarate), glatiramer acetate, mitoxantrone, teriflunomide, suplatast tosilate, mycophenolate mofetil and cyclophosphamide, laquinimod, voclosporin, PUR-118, AMG 357, AMG 811, BCT197;

Antimalarials, including but not limited to, hydroxychloroquine (Plaquenil) and chloroquine (Aralen), cyclophosphamide (Cytoxan), methotrexate (Rheumatrex), azathioprine (Imuran), mesalamine (Asacol) and sulfasalazine (Azulfidine):

Antibiotics, including but not limited to, Flagyl or ciprofloxacin;

Anti-TNFα agents, including but not limited to, infliximab, adalimumab, certolizumab pegol, golimumab and etanercept;

Anti-CD20 agents, including but not limited to, rituximab, ocrelizumab, ofatumumab and PF-05280586;

Antidiarrheals, such as diphenoxylate (Lomotil) and loperamide (Imodium);

Bile acid binding agents, such as cholestyramine, alosetron (Lotronex) and ubiprostone (Amitiza);

Laxatives, such as Milk of Magnesia, polyethylene glycol (MiraLax), Dulcolax, Correctol and Senokot, and anticholinergics or antispasmodics such as dicyclomine (Bentyl);

T lymphocyte activation inhibitors, including but not limited to, abatacept:

Anti-IL1 treatments, including but not limited to, anakinra, rilonacept, canakinumab, gevokizumab, MABp1 and MEDI-8968;

Glucocorticoid receptor modulators that may be dosed orally, by inhalation, by injection, topically, rectally, by ocular delivery, including but not limited to, betamethasone, prednisone, hydrocortisone, prednisolone, flunisolide, triamcinoline acetonide, beclomethasone, dipropionate, budesonide, fluticasone propionate, ciclesonide, mometasone furoate, fluocinonide, desoximetasone, methylprednisolone or PF-04171327;

Aminosalicyic acid derivatives, including but not limited to, sulfasalazine and mesalazine;

Anti-α4 integrin agents, including but not limited to, natalizumab;

α1- or α2-adrenergic agonist agents including but not limited to: propylhexidrine, phenylephrine, phenylpropanolamine, pseudoephedrine or naphazoline hydrochloride, oxymetazoline hydrochloride, tetrahydrozoline hydrochloride, xylometazoline hydrochloride or ethylnorepinephrine hydrochloride;

β-adrenergic agonists, including but not limited to, metaproterenol, isoproterenol, isoprenaline, albuterol, salbutamol, formoterol, salmeterol, terbutaline, orciprenaline, botolterol mesylate, pirbuterol;

Anticholinergic agents, including but not limited to, ipratropium bromide, tiotropium bromide, oxitropium bromide, aclindinium bromide, glycopyrrolate, pirenzipine or telenzepine;

Inhaled long acting beta-agonists, long acting muscarinic antagonists and long acting corticosteroids, including but not limited, to those included in the following reference: Y. Mushtaq, The COPD pipeline, *Nat Rev Drug Discov,* 2014, 13(4), 253-254. http://dx.doi.org/10.1038.nrd425;

Leukotriene pathway modulators, including but not limited to, 5-LO inhibitors (such as zileuton), FLAP antagonists (such as veliflapon, fiboflapon), LTD4 antagonists (such as montelukast, zafirlukast or pranlukast;

H1 receptor antagonists, including but not limited to, cetirizine, loratidine, desloratidine, fexofenadine, astemizole, azelastine or chlorpheniramine;

PDE4 inhibitors, including but not limited to, apremilast, roflumilast or AN2728;

Vitamin D receptor modulators, including but not limited to, paricalcitol;

Nrf2 pathway activators, including but not limited to, fumarates, sulfurophane and bardoxolone methyl;

Modulators of the RAR-related orphan receptor (ROR) family, in particular RORg;

Modulator and/or antagonists of the chemokine receptors, including but not limited to, CCR2 antagonists (such as CCX140, BMS-741672, PF-4634817, CCX-872, NOX-E36), CCR2/5 antagonists (such as PF-4634817), CCR9 (such as vercirnon, CCX507), CCR1 modulators, CCR4 modulators, CCR5 modulators, CCR6 modulators, CXCR6 modulators, CXCR7 modulators) and CXCR2 modulators (such as danirixin, AZD5069);

Prostaglandins, including but not limited to, prostacyclin;

PDE5 inhibitors, including but not limited to, sildenafil, PF-489791, vardenafil and tadalafil;

Endothelin receptor antagonists, including but not limited to, bosentan, ambrisentan, sparsentan, atrasentan, zibotentan and macitentan;

Soluble guanylate cyclase activators, including but not limited to, riociguat;

Interferons, including but not limited to, interferon beta-1a interferon beta-1b;

Sphingosine 1-phosphate receptor modulators, including but not limited to, fingolimod and ponesimod.

Inhibitors of the complement pathway, including but not limited to, C5aR antagonists (such as CCX168, PMX-53, NN8210), C5 inhibitors (such as eculizumab), inhibitors of complement factors B and D, inhibitors of MASP2 (such as OMS-721) and ARC-1905;

Inhibitors of Janus kinases (one of more of JAK1, JAK2, JAK3, TYK2), including but not limited to, decernotinib, cerdulatinib, JTE-052, ruxolitinib, tofacitnib, Baricitinib, Peficitinib, GLPG-0634, INCB-47986, INCB-039110, PF-04965842, XL-019, ABT-494, R-348, GSK-2586184, AC-410, BMS-911543 and PF-06263276;

Inhibitors of other anti-inflammatory or immunomodulatory kinases, including but not limited to, spleen tyrosine kinase (SYK) inhibitors, p38 MAP kinase inhibitors (such as PF-3715455, PH-797804, AZD-7624, AKP-001, UR-13870, FX-005, semapimod, pexmetinib, ARRY-797, RV-568, dilmapimod, ralimetinib), PI3K inhibitors (such as GSK-2126458, pilaralisib, GSK-2269557), PI3Kg and/or PI3Kd inhibitors (such as CAL-101/GS-1101, duvelisib), JNK inhibitors, ERK1 and/or 2 inhibitors, IKKb inhibitors, BTK inhibitors, ITK inhibitors, ASK1 inhibitors (such as GS-4997), PKC inhibitors (such as sotrastaurin), TrkA antagonists (such as CT-327), MEK1 inhibitors (such as E6201);

Antioxidants, including but not limited to, myeloperoxidase inhibitors (such as AZD-3241), NOX4 and other NOX enzymes (such as GKT-137831) and N-acetyl cysteine;

Inhibitors of IL5, including but not limited to, mepolizumab, reslizumab and benralizumab;

Inhibitors of IL4, including but not limited to, pascolizumab, altrakincept and pitrakinra;

Inhibitors of IL13, including but not limited to, tralokinumab, anrukinzumab and lebrikizumab;

Anti-IL6 agents, including but not limited to, tocilizumab, olokizumab, siltuximab, PF-4236921 and sirukumab;

Inhibitors/Antagonists of IL17/IL17R, including but not limited to, secukinumab, RG-7624, brodalumab and ixekizumab;

Antagonists of IL12 and/or IL23, including but not limited to, tildrakizumab, guselkumab, MEDI2070 and AMG 139;

Inhibitors of IL33, including but not limited to, AMG 282;

Inhibitors of IL9, including but not limited to, MEDI-528;

Inhibitors of GM-CSF, including but not limited to, MT203;

Anti CD4 agents, including but not limited to, tregalizumab and rigerimod;

CRTH2 antagonists, including but not limited to, AZD-1981;

Inhibitors of B lymphocyte stimulator (BLYS; also known as BAFF), a protein that is often increased in patients with SLE, including but not limited to, belimumab, tabalumab, blisibimod, and atacicept;

CD22-specific monoclonal antibodies, including but not limited to, epratuzumab;

Inhibitors of interferon-α, including but not limited to, sifalimumab and rontalizumab;

Inhibitor of type I interferon receptors, including but not limited to, MEDI-546;

FcγRIIB agonists, including but not limited to, SM-101;

Modified and/or recombinant versions of Heat Shock Protein 10 (Hsp10, also known as Chaperonin 10 or EPF), including but not limited to, INV-103;

Inhibitors of the TNF superfamily receptor 12A (TWEAK receptor), including but not limited to, BIIB-023, enavatuzumab, and RG-7212;

Inhibitors of xanthine oxidase, including but not limited to, allopurinol, benzbromarone, febuxostat, topiroxostat, tisopurine and inositols;

Inhibitors of URAT1 (also known as SLC22A12), including but not limited to, lesinurad, RDEA 3170, UR1102 and levotofispam;

Additional treatments for gout and/or lowering of uric acid levels, including but not limited to, colchicines, pegloticase, benziodarone, isobrominidione, BCX4208 and arhalofenate;

Inhibitors of toll-like receptors (TLRs), including but not limited to, one or more of TLR7, TLR8, TLR9 (such as IMO-8400, IMO-3100, DV-1179), TLR2 and/or TLR 4 (such as VB-201, OPN-305);

Agonists of TLRs, including but not limited to, TLR7 (such as GSK2245035, AZD8848), TLR9 (such as AZD1419);

Activators SIRT1, including but not limited to, SRT2104;

A3 receptor agonists, including but not limited to, CF101;

Other agents of use of the treatment of psoriasis, including but not limited to, IDP-118, LAS41004, LEO 80185, LEO 90100, PH-10, WBI-1001, CNT01959, BT-061, cimzia, ustekinumab, MK-3222/SCH 900222, ACT-128800, AEB071, alitretinoin, ASP015K, Apo805K1, BMS-582949, FP187, hectoral (doxercalciferol), LEO 22811, Ly3009104 (INCB28050), calcipotriene foam (STF 115469), tofacitinib (CP-690,550), M518101 and CycloPsorb™;

Antifibrotic agents, including but not limited to: pirfenidone, inhibitors of LOXL2 (such as Simtuzumab), FT-011, modulators of epiregulin and/or TGFα (such as LY-3016859), modulators of TGFβ (such as LY-2382770, fresolimumab);

Prolyl hydroxylase inhibitors, including but not limited to, GSK1278863, FG-2216, ASP-1517/FG-4592, AKB-6548, JTZ-951, BAY-85-3934 and DS-1093;

Inhibitors of granulocyte macrophage colony-stimulating factor, including but not limited to, GSK3196165 (MOR103), PD-0360324 and mavrilimumab;

Inhibitors of MAdCAM and/or α4β7 integrin, including but not limited to, PF-00547659 and MEDI7183 (abrilumab);

Inhibitors of connective tissue growth factor (CTGF), including but not limited to, PF-06473871; Inhibitors of cathepsin C, including but not limited to, GSK2793660;

Inhibitors of soluble epoxide hydrolase, including but not limited to, GSK2269557;

Inhibitors of the TNFR1 associated death domain protein, including but not limited to, GSK2862277;

Anti-CD19 agents, including but not limited to, MEDI-551 and AMG 729;

Anti-B7RP1 agents/inhibitors of ICOS ligand, including but not limited to, MEDI5872 and AMG-557;

Inhibitors of thymic stromal lymphoprotein, including but not limited to, AMG157;

Inhibitors of IL2, including but not limited to, daclizumab;

Inhibitors of Leucine rich repeat neuronal protein 6A, including but not limited to, Anti-Lingo (Biogen);

Inhibitors of integrins, including but not limited to, alpha-V/beta-6 (STX-100) and alpha-V/beta-3 (VPI-2690B);

Anti-CD40L agents, including but not limited to, CDP-7657;

Modulators of the dopamine D3 receptor, including but not limited to, ABT-614;

Inhibitors and/or modulators of galectin-3, including but not limited to, GCS-100 and GR-MD-02;

Agents for treating diabetic nephropathy, including but not limited to, DA-9801 and ASP-8232;

Agents for treating acute kidney injury, including but not limited to, THR-184, TRC-160334, NX-001, EA-230, ABT-719, CMX-2043, BB-3 and MTP-131;

Modulators of inflammasomes, including but not limited to, inhibitors of NLRP3;

Modulators of bromodomains, including but not limited to, BRD4;

Modulators of GPR43; and

Inhibitors of TRP channels, including but not limited to, TRPA1, TRPC3, TRPC5, TRPC6 and TRPC6.

Additional therapeutic agents include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, epinephrine, nitroglycerin, nitroprusside, etc.

Combination agents useful for treating vasculitis are included, for example, azathioprine, cyclophosphamide, mycophenolate, mofetil, rituximab, etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another embodiment the second agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another embodiment, the agent is at least one anti-platelet agent. Especially preferred anti-platelet agents are aspirin and clopidogrel. The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as celecoxib or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase. Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil. Examples of suitable cardiac glycosides include digitalis and ouabain.

In one embodiment, a compound of the invention may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™). In another embodiment, a compound of the invention may be co-administered with a loop diuretic. In still another embodiment, the loop diuretic is selected from furosemide and torsemide. In still another embodiment, one or more compounds of the invention may be co-administered with furosemide. In still another embodiment, one or more compounds of the invention may be co-administered with torsemide which may optionally be a controlled or modified release form of torsemide.

In another embodiment, a compound of the invention may be co-administered with a thiazide-type diuretic. In still another embodiment, the thiazide-type diuretic is selected from the group consisting of chlorothiazide and hydrochlorothiazide. In still another embodiment, one or more compounds of the invention may be co-administered with chlorothiazide. In still another embodiment, one or more compounds of the invention may be co-administered with hydrochlorothiazide. In another embodiment, one or more compounds of the invention may be co-administered with a phthalimidine-type diuretic. In still another embodiment, the phthalimidine-type diuretic is chlorthalidone.

Examples of suitable combination mineralocorticoid receptor antagonists include sprionolactone and eplerenone. Examples of suitable combination phosphodiesterase inhibitors include: PDE III inhibitors (such as cilostazol); and PDE V inhibitors (such as sildenafil).

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesteryl ester transfer protein inhibitors.

Anti-inflammatory agents also include sPLA2 and lpPLA2 inhibitors (such as darapladib), 5 LO inhibitors (such as atrelueton) and IL-1 and IL-1r antagonists (such as canakinumab).

Other atherosclerotic agents include agents that modulate the action of PCSK9, for example, called bococizumab.

Cardiovascular complications of type 2 diabetes are associated with inflammation, accordingly, the compounds of the present invention may be used in combination with antidiabetic agents, particularly type 2 anti-diabetic agents. Examples of suitable anti-diabetic agents include (e.g. insulins, metfomin, DPPIV inhibitors, GLP-1 agonists, analogues and mimetics, SGLT1 and SGLT2 inhibitors) Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al., Annual Reports in Medicinal Chemistry 2008, 43, 119-137, GPR119 modulators, particularly agonists, such as those described in WO2010140092, WO2010128425, WO2010128414, WO2010106457, Jones, R. M. et al., in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The compounds of the present invention may be used in combination with neuroinflammatory and neurodegenerative agents in mammals. Examples of additional neuroinflammatory and neurodegenerative agents include antidepressants, antipsychotics, anti-pain agents, anti-Alzheimer's agents, and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, nortriptyline, protriptyline, amoxapine, desipramine and maprotiline. Examples of suitable SSRIs include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable SNRIs of use in the present invention include venlafaxine. Examples of suitable atypical anti-depressants include bupropion, lithium, trazodone and viloxazine. Examples of anti-Alzheimer's agents include NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A receptor (5-HT1A) agonists, and CRF antagonists. Suitable benzodiazepines include alprazolam, chlordiazepoxide, clonazepam, chlorazepate, diazepam, lorazepam, oxazepam, and prazepam. Suitable 5-HT1A receptor agonists include buspirone and ipsapirone. Suitable CRF antagonists include verucerfont. Suitable atypical antipsychotics include paliperidone, ziprasidone, risperidone, aripiprazole, olanzapine, and quetiapine. Suitable nicotine acetylcholine agonists include CP-601927 and varenicline. Anti-pain agents include pregabalin, gabapentin, clonidine, neostigmine, baclofen, midazolam, ketamine and ziconotide.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The present invention further comprises intermediate compounds useful in the synthesis of the compounds of the invention, including salts and/or tautomers thereof.

General Synthetic Schemes

The compounds of Formula Ia may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula Ia, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. Additionally, one skilled in the art will recognize that in many cases, these compounds will be mixtures of stereoisomers that may be separated at various stages of the synthetic schemes using conventional techniques, such as, but not limited to, crystallization, normal-phase chromatography, reversed phase chromatography and chiral chromatography, to afford single enantiomers. The schemes are representative of methods useful in synthesizing the compounds of the present invention. They are not to constrain the scope of the invention in any way.

Methods to prepare compounds of the invention are similar to those described in PCT/IB2015/052251, filed on Mar. 26, 2015, and its corresponding U.S. patent application Ser. No. 14/678,114, filed on Apr. 3, 2015. These methods are hereby incorporated in their entirety as methods of preparation for the compounds of this this invention.

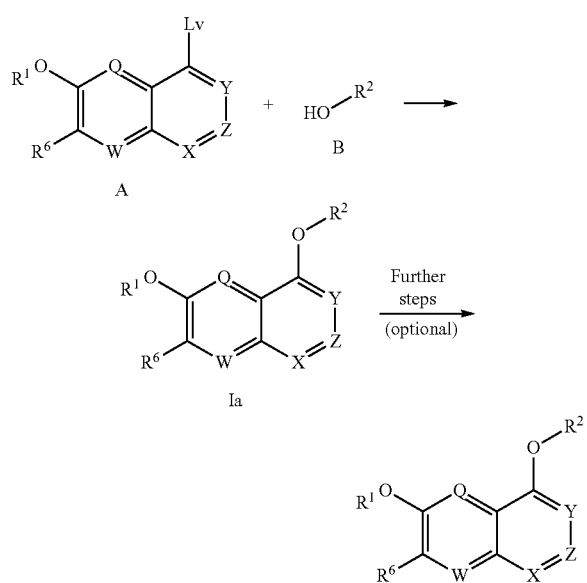

Scheme 1 illustrates a method for preparing compounds of Formula Ia. A compound of Formula A, in which Lv is a displaceable leaving group (such as chloro or fluoro, for example), is treated with a compound of Formula B (as described in PCT/IB2015/052251) to furnish a product of Formula Ia. The reaction is typically carried out in the presence of a suitable base such as cesium carbonate, potassium tert-butoxide, sodium hydride or potassium hexamethyldisilazide in a suitable solvent or solvent mixture, such as THF or dimethylformamide. The compounds of Formula A may be prepared as described in the subsequent schemes. The compounds of Formula B ($R^2$—OH) may be obtained from commercial vendors, or prepared by methods reported in the chemical literature, or may be prepared as described in the subsequent schemes.

If desired, further transformations may be effected upon compounds of Formula Ia. For example, a compound of Formula Ia wherein $R^6$=CN may be subjected to a nitrile hydrolysis reaction to provide a compound of Formula Ia in which $R^6$=CONH$_2$. The reaction may be carried out in a variety of ways known to one skilled in the art, for example by the use of acids or bases, optionally in the presence of an oxidant such as hydrogen peroxide, or by using chemical or enzymatic catalysts. In other cases, the compound of Formula Ia may be further treated with reagents, such as acids, to cleave protecting groups, such as t-butoxycarbonyl groups, and/or with other reagents to derivatize functional groups such as carboxyl, amino, or hydroxyl groups.

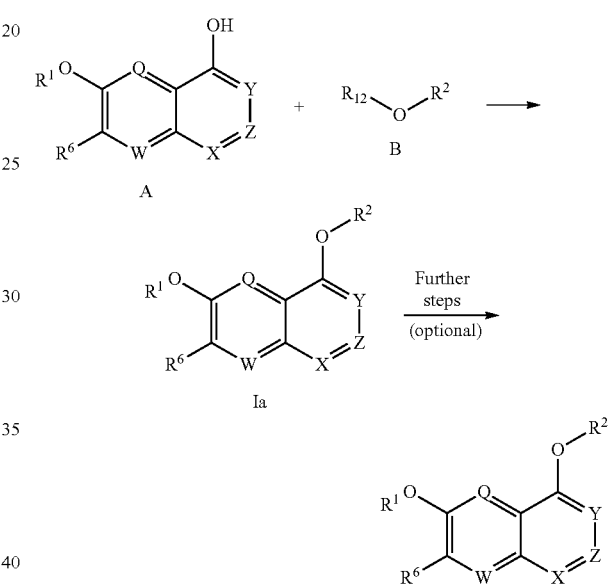

Scheme 2 illustrates another method for the preparation of compounds of Formula Ia, particularly suited to those instances in which X and Y in the compound of Formula A are both carbon. This method provides for the alkylation of a compound of Formula A with a compound of Formula B (wherein the $R^{12}$O— group is either hydroxyl or a sulfonate ester such as p-toluenesulfonate or methanesulfonate; for example, as described in PCT/IB2015/052251, or as commercially available), using methods known to those skilled in the art, to furnish a product of Formula Ia. For example, this reaction may be carried out by treating a compound of Formula A with a compound of Formula B ($R^{12}$=H) in the presence of triphenylphosphine and an azodicarboxylate ester ("Mitsunobu reaction") in a suitable solvent such as THF. Alternatively, the alkylation of a compound of Formula A may be effected using a compound of Formula B ($R^{12}$O=TsO or other sulfonate ester) in the presence of a base such as cesium carbonate, in a suitable solvent such as THF or dimethylformamide.

If desired, further transformations may be effected upon the compound of Formula Ia. For example, the compound of Formula Ia wherein $R^6$=CN may be subjected to a nitrile hydrolysis reaction to provide a compound of Formula Ia in which $R^6$=CONH$_2$. The reaction may be carried out in a variety of ways known to one skilled in the art, for example by the use of acids or bases, optionally in the presence of an oxidant such as hydrogen peroxide, or by using chemical or enzymatic catalysts. In other cases, the compound of Formula Ia may be further treated with reagents, such as acids, to cleave protecting groups, such as t-butoxycarbonyl groups, and/or with other reagents to derivatize functional groups such as carboxyl, amino, or hydroxyl groups.

Scheme 3

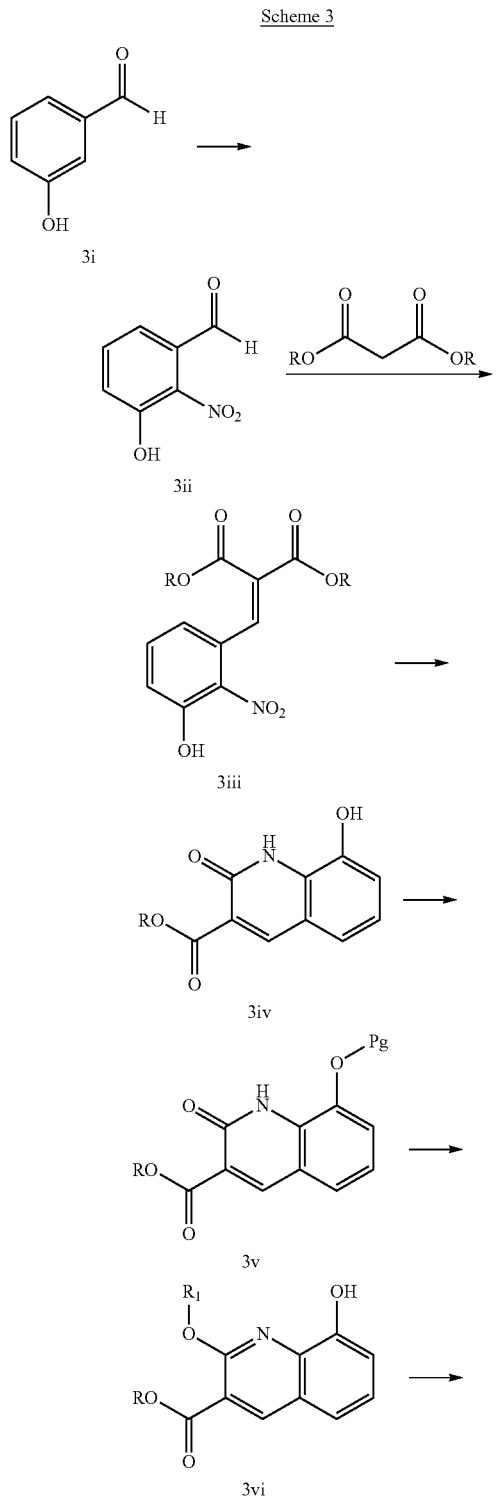

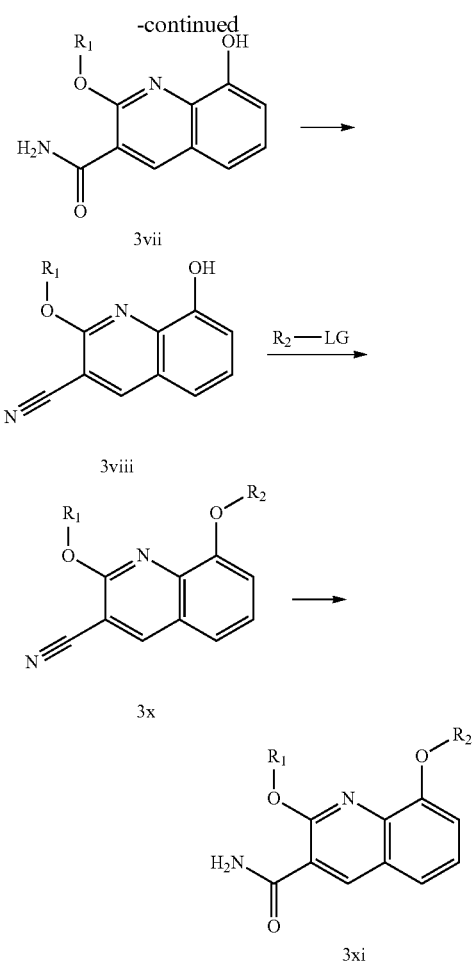

A route to compounds of Formula Ia where Q=N and W, X, Z and Y are CH are illustrated in Scheme 3. An aldehyde such 3i can be nitrated, for example, with a nitrate such as isopropyl nitrate in the presence of acid, to give a nitro compound such as 3ii. Condensation of compound 3ii with a malonate may afford an intermediate such as 3iii which can be reduced, for example, by using sodium hydrosulfite, leading to cyclization to a pyridine such 3iv. The phenol moiety can be protected with an appropriate protecting group such as a benzyl group as described in the literature [see, for example, Wuts, P. G. M. and Greene, T. W., Greene's Protective Groups in Organic Synthesis, Wiley (2007)] to give a compound such as 3v, where Pg is a suitable protecting group. A compound such 3v can activated, for example, with phosphorus oxychloride to form an iminochloride, which can be subsequently treated with an alkoxide such as sodium methoxide to give a product such as compound 3vi wherein the protecting group has concurrently been removed. A compound such as ester 3vi can be converted to the amide by treatment, for example, with ammonia in methanol, to give an amide 3vii. Amide 3vii can be dehydrated with reagents such as pyridine TFAA to give nitriles such as 3viii. Alkylation of phenol 3viii using an alkylating agent such as a mesylate or halide derivative in the presence of a base may afford compounds represented by 3x. Exemplary bases include but are not limited to cesium carbonate. Nitrile 3x can be hydrolyzed, for example, by using hydrogen peroxide and potassium carbonate in DMSO, to afford amides such as 3xi.

Scheme 4

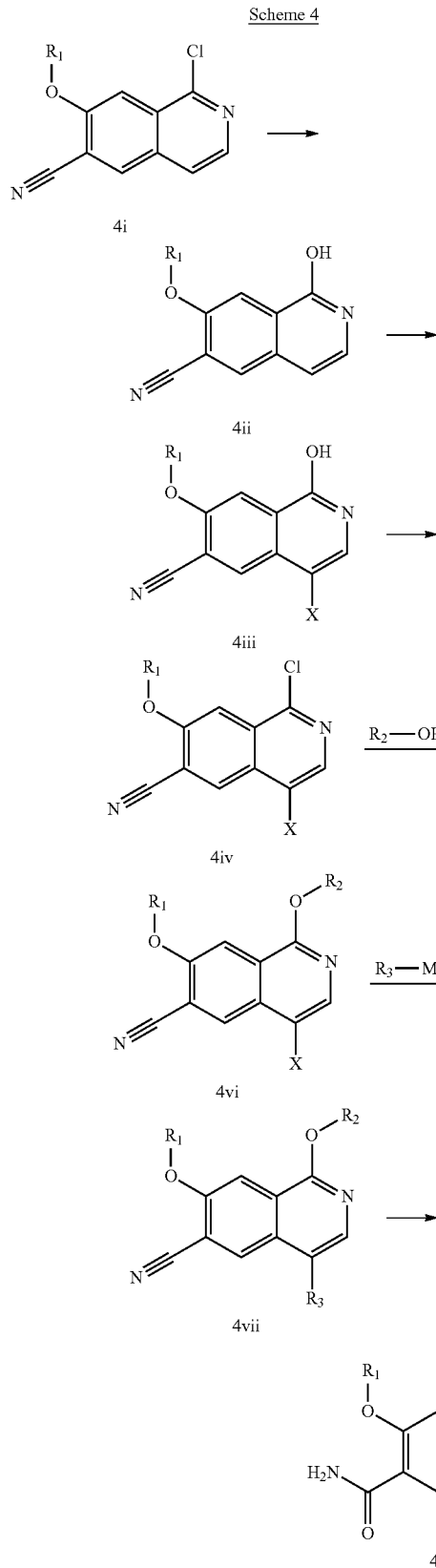

halides 4vi in Scheme 4. The preparation of compounds such as 4vi may be accomplished as follows. Compounds such as 4i can be treated with aqueous acid to give compounds such as 4ii which can be converted to halides such as 4iii, for example, by bromination using NBS. Activation of compounds such as 4iii with reagents such as phosphorus oxychloride may afford compounds such as chloride 4iv. Treatment of compound 4iv with an alcohol and an appropriate base such as NaHMDS can effect conversion to compounds such as 4vi. Treatment of compounds such as 4vi with, for example, heterocyclic stannanes or boronates or metalloids and an appropriate catalyst, for instance a palladium catalyst may afford cross-coupled products such as compound 4vii. Hydration of nitrile 4vii, for example, with hydrogen peroxide and potassium carbonate, may afford carboxamides such as compound 4viii.

Scheme 5

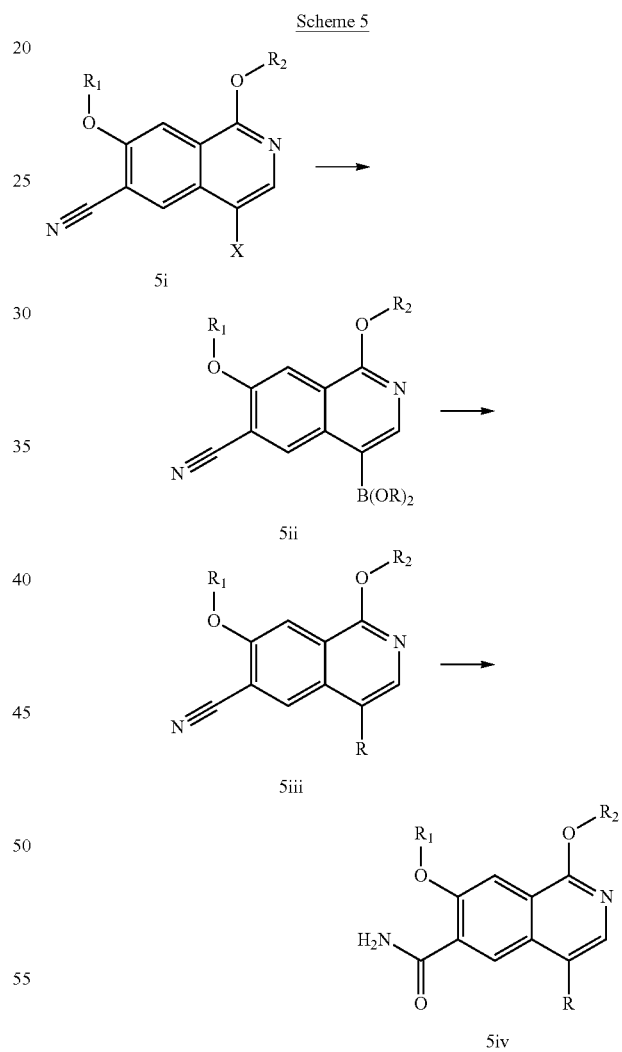

Compounds of the invention may be prepared by metal catalyzed cross-coupling reactions of compounds such as Alternatively compounds of this type may be prepared from Suzuki coupling reactions as depicted in Scheme 5. For example, compounds such as 5i, where X is a halogen, may be treated with a boron reagent such as bis(pinacolato)diboron, base, and an appropriate palladium catalyst to afford a boronate ester intermediate such as 5ii. Treatment of 5ii with a heterocyclic halide, base, and an appropriate palladium catalyst gives compounds such 5iii, where R is a heterocycle. Compounds such as 5iii can be hydrated using, for example, hydrogen peroxide and potassium carbonate, to give compounds such as 5iv. In some cases the heterocycle will bear a protecting group, and standard methods to remove the protecting groups known to those skilled in the art may be utilized.

Scheme 6

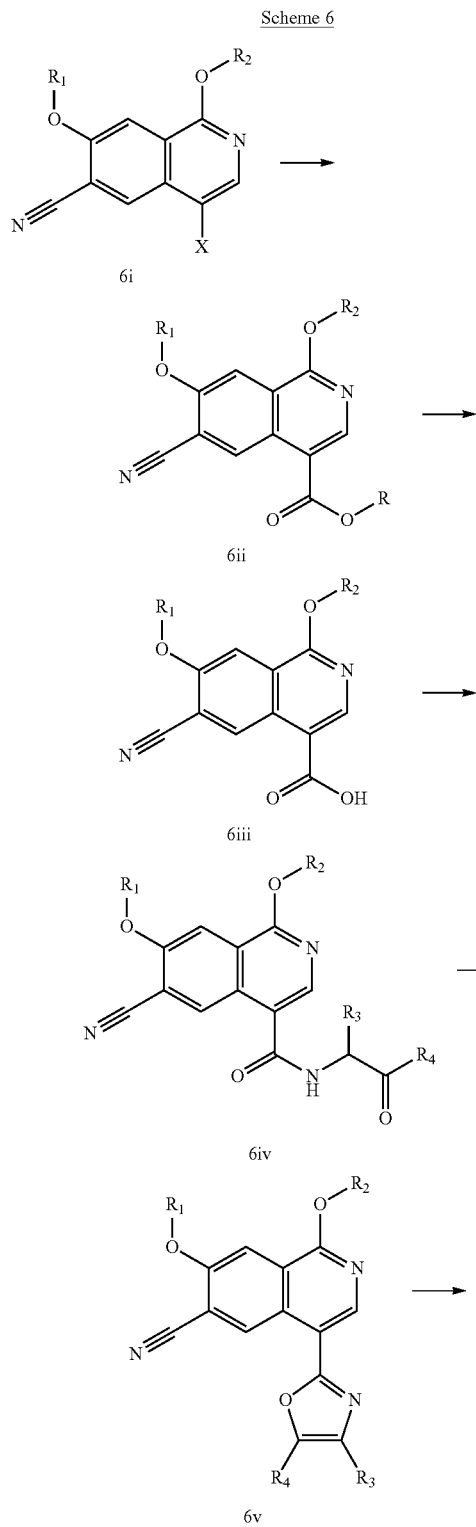

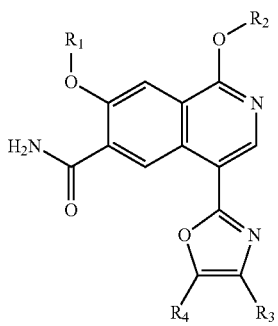

Carbonylation of a compound such as 6i, where X=halogen, such as Br, using an appropriate palladium catalyst under carbon monoxide, base, and an appropriate alcohol can provide compounds such as carboxylic ester 6ii, which in turn can be hydrolyzed, for example, in the presence of lithium hydroxide in a mixture of aqueous THF/alcohol, to carboxylic acids such as 6iii. Carboxylic acids such as 6iii can be converted to amides such as 6iv, for example, by treatment with an amine, base, and a coupling reagent such as HATU. Oxazole compounds such as 6v may be formed by ring closure of amide 6iv under suitable reaction conditions, such as TFAA and an amine base. Nitrile hydrolysis may be effected using, for example, hydrogen peroxide and potassium carbonate in DMSO, to provide carboxamides such as 6vi.

Scheme 7

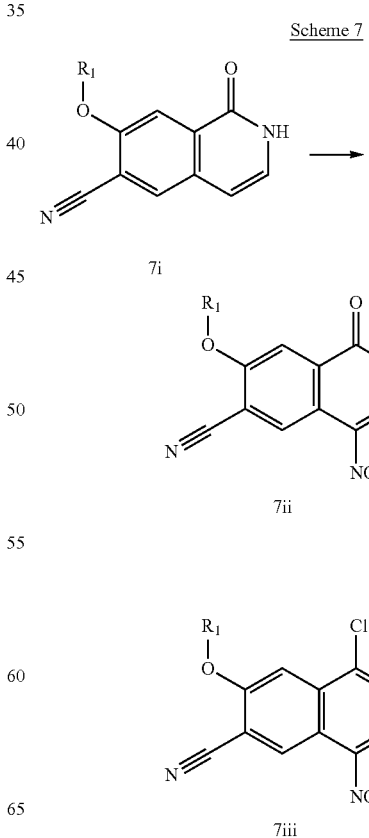

-continued

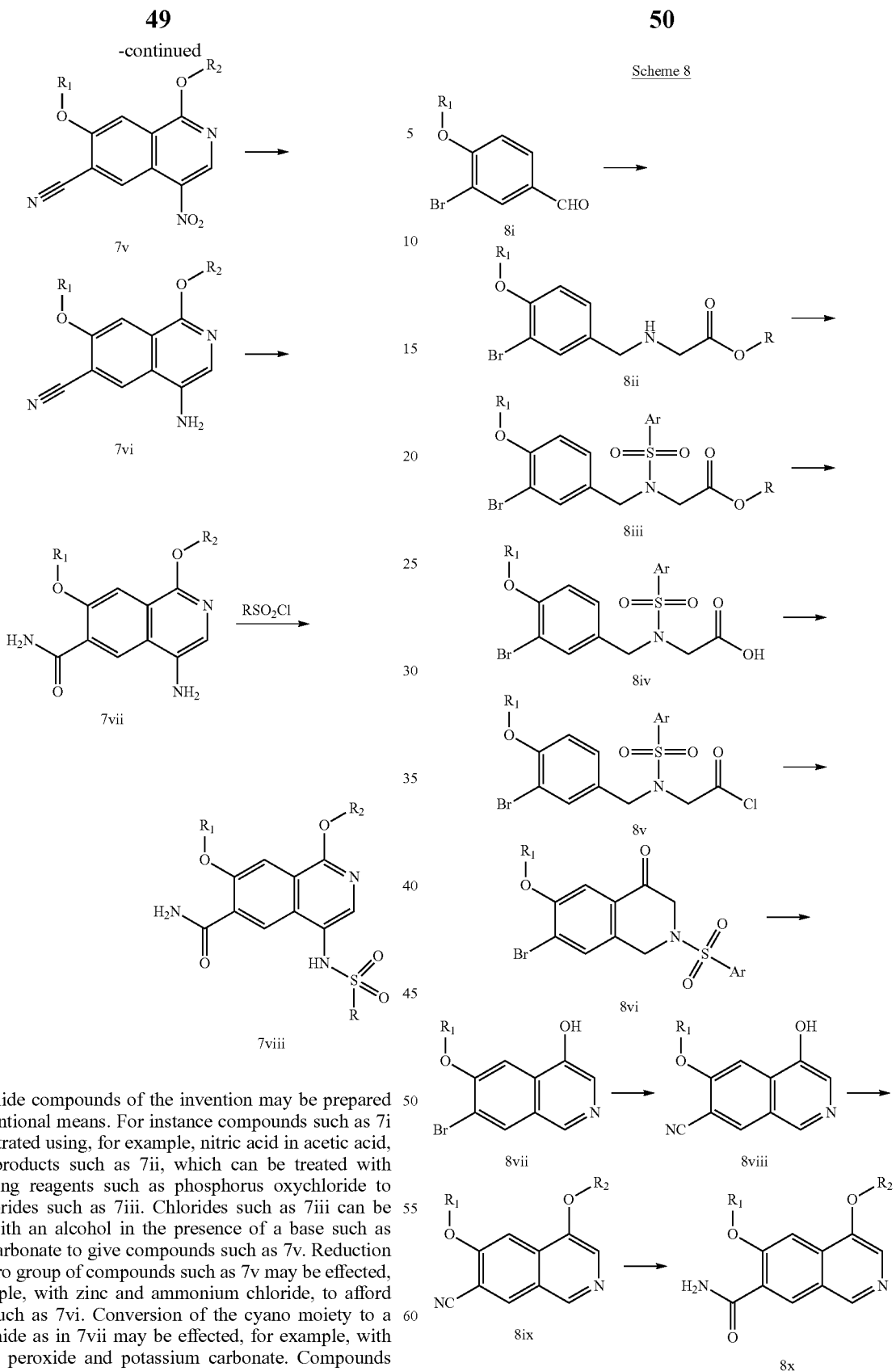

Sulfonamide compounds of the invention may be prepared by conventional means. For instance compounds such as 7i can be nitrated using, for example, nitric acid in acetic acid, to give products such as 7ii, which can be treated with chlorinating reagents such as phosphorus oxychloride to give chlorides such as 7iii. Chlorides such as 7iii can be treated with an alcohol in the presence of a base such as cesium carbonate to give compounds such as 7v. Reduction of the nitro group of compounds such as 7v may be effected, for example, with zinc and ammonium chloride, to afford amines such as 7vi. Conversion of the cyano moiety to a carboxamide as in 7vii may be effected, for example, with hydrogen peroxide and potassium carbonate. Compounds such as 7vii can be converted to sulfonamides such as 7viii by reaction with sulfonyl chlorides and an appropriate base such as pyridine. The nitrile hydration step may be accomplished before or after sulfonylation to give a compound such as 7viii.

Scheme 8 illustrates a sequence to prepare compounds where Z=N. Reductive amination of an aldehyde such as 8i with a glycinate ester provides an amine derivative 8ii which can be sulfonylated, for instance, with an aryl sulfonyl chloride such as p-toluenesulfonyl chloride in the presence of base such as pyridine to afford moieties such as 8iii. Ester hydrolysis, for example, using lithium hydroxide in a mixture of aqueous THF/alcohol, gives carboxylic acids such as 8iv which may be converted into an acid chlorides such as 8v using reagents such as thionyl chloride. Friedel-Crafts acylation of compounds such as 8v may be effected using Lewis Acids such as aluminum trichloride to provide products such as 8vi. Treatment of compounds such as 8vi with base, such as carbonate or bicarbonate salts in an alcohol such as ethanol, at reflux temperature effects the conversion to phenol compounds such as 8vii, which may be converted to cyano derivatives such as 8viii by, for example, the action of copper or zinc cyanide and a palladium catalyst in a solvent such as DMF. Mitsunobu reaction or an O-alkylation reaction may be employed as described in Scheme 2 to generate an ether compound such as 8ix, and treatment of the nitrile with basic hydrogen peroxide as described in Scheme 1 may provide compounds such as 8x.

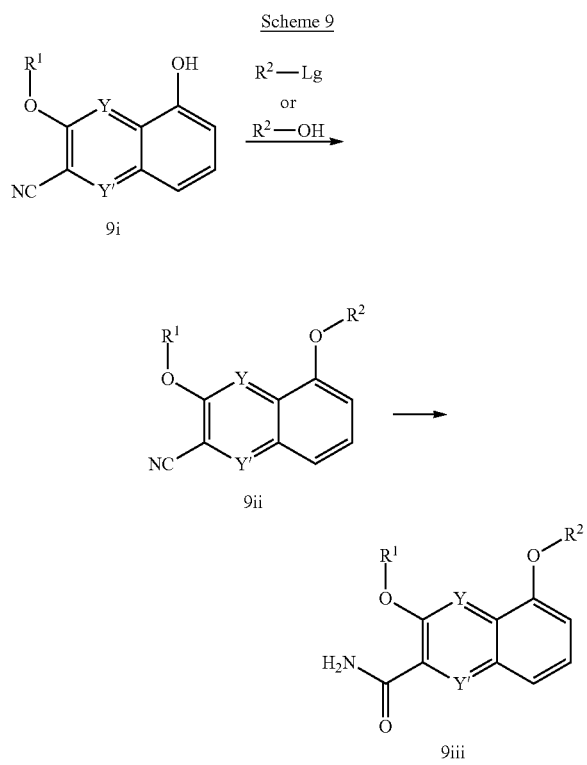

Scheme 9 outlines the transformation of a compound 9i (for example, a naphthol, if Y=Y'=CH) to an ether such as 9ii. For example, the alkylation of 9i may be effected using a compound such as $R^2$-Lg (for example, in which the leaving group Lg=MsO or other sulfonate esters) in the presence of a base such as cesium carbonate, in a suitable solvent such as THF or dimethylformamide. Alternatively, this reaction may be carried out by treating a compound such as 9i with an alcohol $R^2$—OH in the presence of triphenylphosphine and an azodicarboxylate ester ("Mitsunobu reaction") in a suitable solvent such as THF. The nitrile 9ii may then be converted to the amide compound 9iii as described before with base and hydrogen peroxide in DMSO.

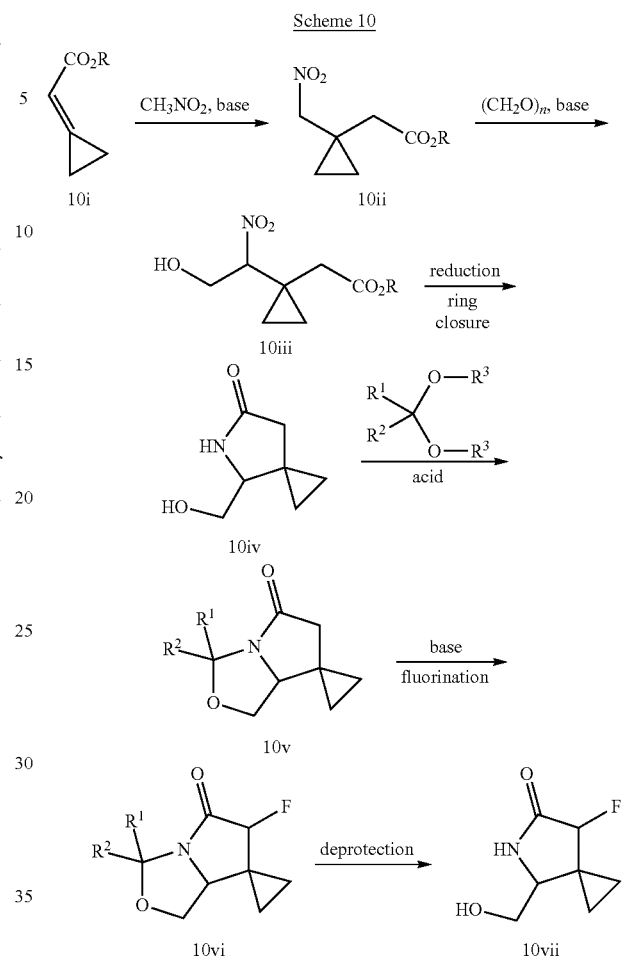

An alcohol compound that might be used, for example, as $R^2OH$ (as in Scheme 1) or converted to $R^2OR^{12}$ (as in Scheme 2) may be obtained by a sequence outlined in Scheme 10. An ester such as 10i (R=Et) (*Organic Letters*, 2014, 16, 4352.) may be converted to the nitromethane derivative 10ii in the presence of a suitable base such as DBU and nitromethane. The nitroalkane derivative may be alkylated with paraformaldehyde and a base such as potassium fluoride to the product 10iii. The nitro group of 10iii may be reduced to the corresponding amine using a suitable reducing agent such as Raney Nickel and hydrogen gas in an alcohol solvent such as ethanol. This crude solution may be warmed and made to cyclize to the indicated lactam compound 10iv. Aminal formation with ketals such as acetone dimethylketal ($R^1$=$R^2$=$R^3$=Me) under acid catalysis such as with tosic acid may provide a compound 10v. This compound 10v can be deprotected, or optionally further functionalized, for example, by deprotonation with a strong base such as lithium diisopropyl amide or lithium hexamethyldisilazide in a solvent such as THF and then treated with standard fluorinating agents such as N-fluorobenzenesulfonimide (NFSI) to afford a compound mixture of diastereomers such as 10vi. Aqueous acid, for example, a mixture of TFA in water and MeCN, may be used to deprotect the aminal and afford a mixture of diastereomeric alcohol compounds 10vii which may be used as such in various preparations.

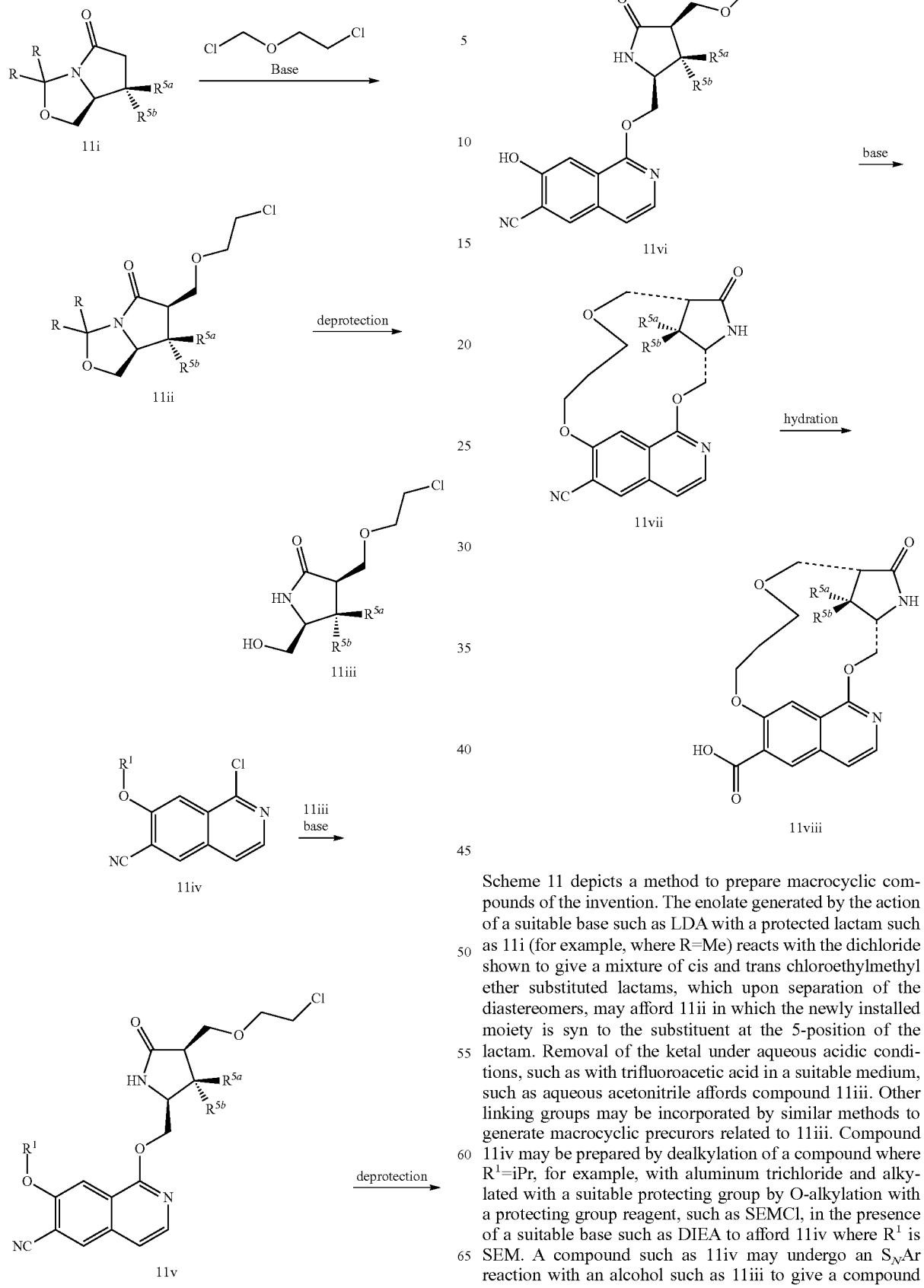

Scheme 11 depicts a method to prepare macrocyclic compounds of the invention. The enolate generated by the action of a suitable base such as LDA with a protected lactam such as 11i (for example, where R=Me) reacts with the dichloride shown to give a mixture of cis and trans chloroethylmethyl ether substituted lactams, which upon separation of the diastereomers, may afford 11ii in which the newly installed moiety is syn to the substituent at the 5-position of the lactam. Removal of the ketal under aqueous acidic conditions, such as with trifluoroacetic acid in a suitable medium, such as aqueous acetonitrile affords compound 11iii. Other linking groups may be incorporated by similar methods to generate macrocyclic precursors related to 11iii. Compound 11iv may be prepared by dealkylation of a compound where $R^1$=iPr, for example, with aluminum trichloride and alkylated with a suitable protecting group by O-alkylation with a protecting group reagent, such as SEMCl, in the presence of a suitable base such as DIEA to afford 11iv where $R^1$ is SEM. A compound such as 11iv may undergo an $S_NAr$ reaction with an alcohol such as 11iii to give a compound such as 11v. The protecting group from compound 11v may be removed under acidic conditions, for example in the case of the SEM group, with HCl in MeOH. An intramolecular cyclization may be induced in dilute solution using base catalysis, for instance, with potassium tert butoxide in the presence of NaI give compound 11vii. Conversion of cyanide 11vii to amide 11viii may be effected, for example, with hydrogen peroxide in DMSO with potassium carbonate.

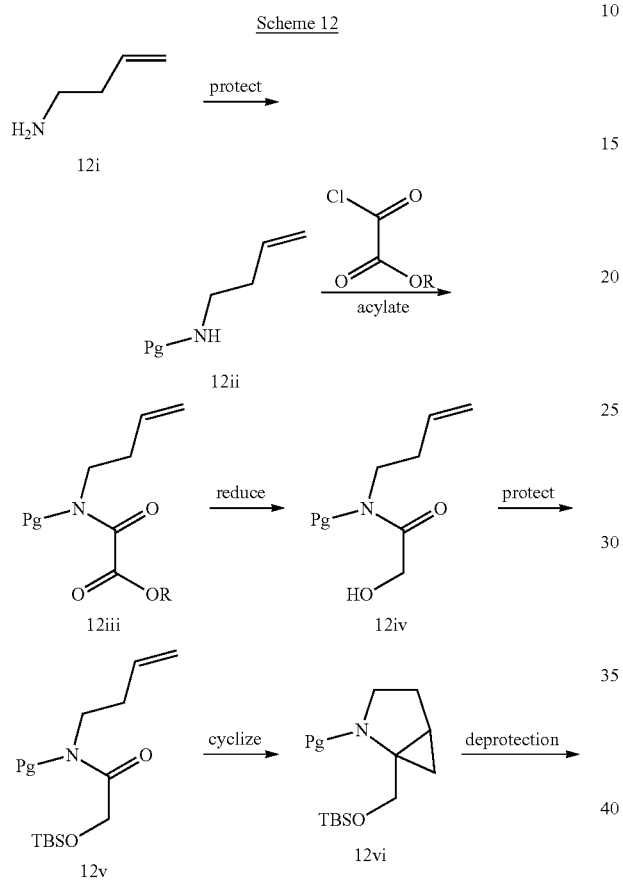

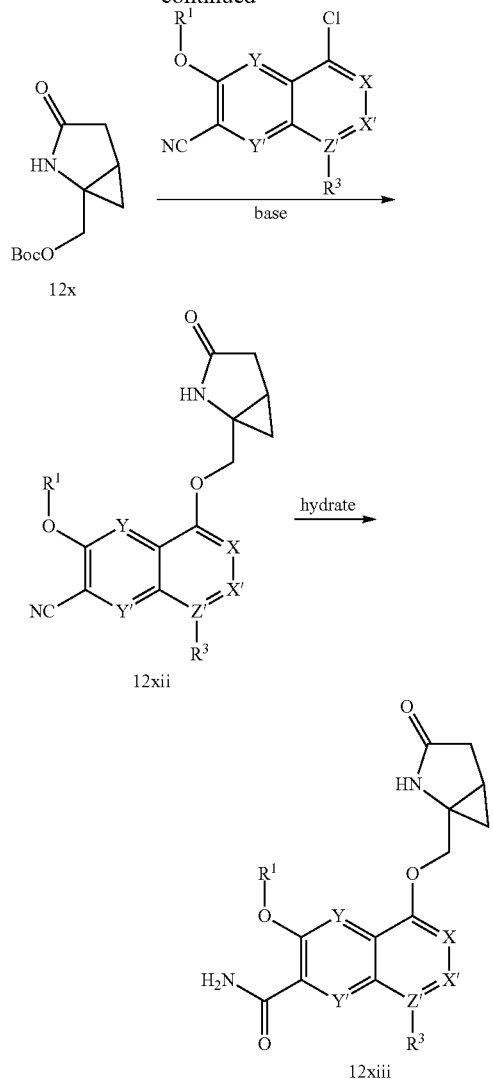

Lactams bearing a fused cyclopropane, e.g., compounds such as 12x, may be prepared as in Scheme 12. Homoallylamine 12i can be protected with a suitable protecting group such as PMB, for example, by reaction with 4-methoxybenzaldehyde in the presence of a reducing agent, typically sodium cyanoborohydride, in a protic solvent, typically ethanol, to generate secondary amines such 12ii via reductive amination. Compounds such as 12ii can be N-acylated, for example by treatment with a base and an acid chloride of general formula ClC(O)CO$_2$R, where R is an alkyl group such as methyl, to generate an amide compound 12iii. Exemplary bases include but are not limited to sodium bicarbonate. Compounds such as 12iii can be reduced to the primary alcohol 12iv upon treatment with a reducing agent such as sodium borohydride in a protic solvent such as methanol. Compounds such as 12iv can be protected as a trialkylsilyl ether, for example, TBS ether, by treatment with a base and the corresponding trialkylsilyl chloride, such as TBSCl. Exemplary bases include but are not limited to imidazole. The resulting compound 12v can undergo a Kulinkovich-de Meijere cyclization reaction to give a bicyclic compound 12vi by treatment with a titanium alkoxide and a Grignard reagent. Examplary titanium alkoxides include but are not limited to titanium isopropoxide and exemplary Grignard reagents include but are not limited to cyclopentylmagnesium bromide. Global deprotection can be achieved by treatment of 12vi with ACE-Cl in a chlorinated solvent, typically 1,2-dichloroethane, followed by warming of the intermediate in methanol to provide the HCl salt of compound 12vii. Temperature can range from room temperature up to reflux in methanol for this conversion. Compound 12vii can be nitrogen protected for example as a tert-butyl carbamate by treatment with di-tert-butyl dicarbonate, a base and 4-dimethylaminopyridine. Exemplary bases include but are not limited to tertiary amines such as triethylamine. In situ addition of TBSCl and a base, typically imidazole, can lead to fully protected amino alcohol compound 12viii. Compound 12viii can be oxidized to lactam 12ix by treatment with a metal oxide, typically ruthenium dioxide hydrate and sodium periodate in a biphasic environment such as an equivolume mixture of ethyl acetate and water to perform this oxidation. Alternative methods to generate lactams such as 12ix have appeared and may be applicable to such syntheses (e.g. DOI: 10.1002/anie.201505916). Treatment of lactam 12ix with a fluoride anion source in an ethereal solvent, typically THF, can lead to compound 12x. Exemplary fluoride anion sources include but are not limited to tetrabutylammonium fluoride. (Migration of the protecting group has been shown to occur in related examples: see Org. Lett., 2001, 3 (3), pp 433-435.) Compounds 12x can be converted to 12xii by $S_NAr$ reaction with an activated heterocyclic moiety such as a chloride represented by 12xi (for example, where X and/or Z is N and where $R^1$ may be any alkyl substituent; exemplary $R^1$ substituents include but are not limited to methyl and iso-propyl) with an excess of base at low temperature in a polar solvent. Exemplary bases and solvents include but are not limited to KHMDS in DMF respectively. The temperature can range from −78° C. to room temperature and the reaction is typically performed at −10° C. Conversion of compound 12xii to compound 12xiii can be achieved by treatment with a base, a peroxide in a polar solvent. Exemplary bases, peroxides and solvents include but are not limited to potassium carbonate, hydrogen peroxide and DMSO respectively. Enantiomers of compound 12xiii can be separated by chiral chromatography.

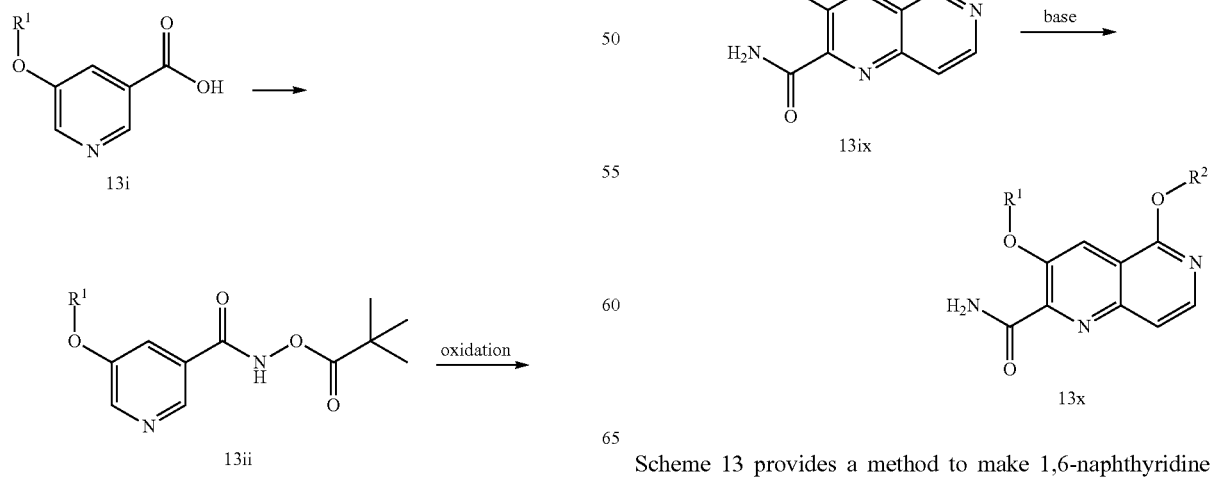

Scheme 13 provides a method to make 1,6-naphthyridine derivatives of the invention. A nicotinic acid derivative such as 13i may be converted to the corresponding acid chloride by those skilled in the art. Exemplary conditions include, but are not limited to, the use of oxalyl chloride in the presence of DMF. The acid chloride intermediate may then react with 1-(aminooxy)-2,2-dimethylpropan-1-one triflate in the presence of a base to provide compounds such as 13ii. Exemplary bases include but are not limited to pyridine. Pyridine compounds such as 13ii may be oxidized to the corresponding N-oxide derivatives 13iii. Exemplary oxidative conditions include but are not limited to the use of a catalytic amount of methyl(trioxo)rhenium in the presence of an aqueous hydrogen peroxide solution under heterogeneous solvent system. Rh-catalyzed C—H activation in the presence of a base and an alkene in a protic solvent may lead to compounds such as 13v (J. Am. Chem. Soc. 2013, 135, 14492). Exemplary bases and alkenes include, but are not limited to sodium acetate and norbornadiene 13iv. Upon heating, a retro Diels-Alder reaction may occur to generate compounds such as 13vi. The latter may be cyanated, for example, by treatment with dimethylcarbamic chloride in the presence of a cyanide source, typically trimethylsilanecarbonitrile, to furnish compounds such as 13vii. Chlorination, for example, by treatment with phosphoryl chloride at high temperature, typically between 70° C. and 110° C., can deliver elaborated 1,6-naphthyridines represented by 13viii. Conversion of the cyano group of 13viii to a carboxamide as in 13ix can be achieved by treatment potassium carbonate, hydrogen peroxide and DMSO as described for other compounds herein. $S_NAr$ reaction of alcohols $R^2$—OH with activated heterocycles such as 13ix can be accomplished in the presence of an excess of base in a polar solvent while heating to furnish compounds such as 13x. Exemplary bases and solvents include but are not limited to KHMDS and DMF respectively.

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

It will be understood that the intermediate compounds of the invention depicted above are not limited to the particular enantiomer shown, but also include all stereoisomers and mixtures thereof. It will also be understood that compounds of Formula Ia can include intermediates of compounds of Formula Ia.

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography and/or liquid chromatography-mass spectrometry, and subjected to work-up when appropriate. It will be recognized by one skilled in the art that purifications may vary between experiments: in general, sorbents, solvents and the solvent ratios used for eluants/gradients were chosen to provide appropriate $R_f$s or retention times. It will also be recognized by one skilled in the art that HPLC purifications may be effected in a variety of ways, including the use of normal stationary phases, reverse stationary phases, chiral stationary phases, and supercritical eluants. The appropriate choices of conditions for chromatographic and HPLC purifications will be discerned by one skilled in the art.

The following Preparations describe the preparation of certain intermediates used in the Methods and Examples that follow. The following Preparations, Methods and Examples are intended to illustrate particular embodiments of the invention and preparations thereto and are not intended to limit the specification, including the claims, in any manner. Unless noted otherwise, all reactants were obtained commercially.

In the non-limiting Examples and Preparations that are set out later in the description and in the aforementioned Schemes, the following abbreviations, definitions and analytical procedures may be referred to:

Abbreviations

ACE-Cl: 1-chloroethyl chloroformate
Boc: tert-butoxy carbonyl
CO: carbon monoxide
DBU: 1,8-diazabicyclo[5.4.0]undec-7-ene
DCE: dichloroethane
DCM: dichloromethane
DIEA: diisopropylethylamine
DMAP: 4-dimethylaminopyridine
DMF: dimethylformamide
DMSO: dimethylsulfoxide
EDCI: 1-ethyl-3-(3-dimethylaminopropyl)carbodiimide
EtOAc: ethyl acetate
EtOH: ethyl alcohol
FA: formic acid
h: hour
HATU: O-(7-azabenzotriazol-1-yl)-N,N,N',N'-tetramethyluronium hexafluorophosphate
HCl: hydrochloric acid
$HNO_3$: nitric acid
$H_2O$: water
$H_2O_2$: hydrogen peroxide
HOAc: acetic acid
HOBT: hydroxybenzotriazole
$H_2SO_4$: sulfuric acid
$K_2CO_3$: potassium carbonate
KHMDS: potassium bis(trimethylsilyl)amide
LiOH.$H_2O$: lithium hydroxide monohydrate
PMB: para-methoxybenzyl
MeCN: acetonitrile
MeOH: methanol
$MgSO_4$: magnesium sulfate
min: minutes
MS: mass spectrometry
Na: sodium
$Na_2S_2O_3$: sodium hydrosulfite
$Na_2SO_4$: sodium sulfate
$NH_4Cl$: ammonium chloride
$NaHCO_3$: sodium bicarbonate NaHMDS: sodium bis(trimethylsilyl)amide
N-BuLi: n-butyllithium
NBS: N-bromosuccinimide
Pd(PPh$_3$)$_4$: tetrakis(triphenylphosphine)palladium (0)
PdCl$_2$(dppf): [1,1'-Bis(diphenylphosphino)ferrocene]dichloropalladium(II),
POCl$_3$: phosphorus oxychloride
S$_N$Ar: substitution nucleophilic aromatic
TBAF: tetrabutylammonium fluoride
TBA-HSO$_4$ tetrabutylammonium hydrogensulfate
TBS: tert-butylsilyl
TBSCl: tert-butyldimethylsilyl chloride
TEA: triethylamine
TFA: trifluoroacetic acid
TFAA: trifluoroacetic anhydride
THF: tetrahydrofuran
TLC: thin layer chromatography
Zn: zinc $^1$H Nuclear magnetic resonance (NMR) spectra were in all cases consistent with the proposed structures. Characteristic chemical shifts (δ) are given in ppm downfield from tetramethylsilane (for $^1$H-NMR) using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol.

Mass spectra, MS (m/z), were recorded using either electrospray ionization (ESI) or atmospheric pressure chemical ionization (APCI). Where relevant and unless otherwise stated the m/z data provided are for isotopes $^{19}$F, $^{35}$Cl, $^{79}$Br and $^{127}$I.

Assignment of enantiomer stereochemistry was based upon the consistent SAR pattern observed for this series of IRAK4 inhibitors and assumptions in light of the stereochemistry ascertained in previous series, as detailed in co-pending U.S. patent application Ser. No. 14/678,114, filed by Pfizer Inc on Apr. 3, 2015, and U.S. Provisional Application 62/204,521, filed on Aug. 13, 2015.

EXAMPLES

Example 1

8-{[(2S,3S,4S)-3-Ethyl-4-fluoro-5-oxopyrrolidin-2-yl]methoxy}-2-methoxyquinoline-3-carboxamide

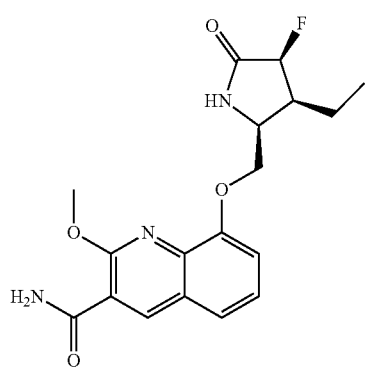 [SMILES: CC[C@@H]1[C@H](F)C(=O)N[C@@H]1COc1cccc2cc(C(N)=O)c(OC)nc12]

Step 1: Preparation of 3-Hydroxy-2-nitrobenzaldehyde

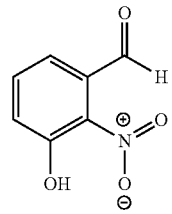

To 3-hydroxybenzaldehyde (5.00 g, 40.9 mmol) in anhydrous DCM (100 mL) at room temperature was added isopropyl nitrate (10.8 g, 102 mmol) followed by TBA-HSO$_4$ (139 mg, 0.409 mmol). Sulfuric acid (5 mL) was added dropwise. The mixture was stirred at 15° C. for 30 min. The mixture was washed with brine, and the organic layer was collected and dried over anhydrous MgSO$_4$, filtered and concentrated. The residue was purified via flash chromatography using 0-99% EtOAc in petroleum ether to give the title compound as a solid (3.1 g, 45% yield). $^1$H NMR (400 MHz, CDCl$_3$) δ 10.43 (s, 1H), 10.32 (s, 1H), 7.64-7.81 (m, 1H), 7.36-7.43 (m, 1H), 7.30-7.35 (m, 1H). HPLC: Ultimate XB-C18, 3 um, 3.0×50 mm, SN:111201514 Mobile phase: 1% MeCN in water (0.1% TFA) to 5% MeCN in water (0.1% TFA) in 1 min then from 5% MeCN in water (0.1% TFA) to 100% MeCN (0.1% TFA) in 5 min hold at 100% MeCN (0.1% TFA) for 2 min then back to 1% MeCN in water (0.1% TFA) at 8.01 min, and hold 2 min. Flow rate: 1.2 ml/min. Retention time 3.19 min.

Step 2: Preparation of Dimethyl 2-(3-hydroxy-2-nitrobenzylidene)malonate

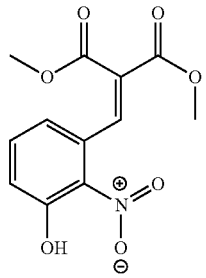 [SMILES: COC(=O)C(=Cc1cccc(O)c1[N+](=O)[O-])C(=O)OC]

To 3-hydroxy-2-nitrobenzaldehyde (200 mg, 1.20 mmol) in MeOH (5 mL) was added piperidine (118 uL, 1.20 mmol) followed by dimethyl malonate (190 mg, 1.20 mmol) and HOAc (87.9 uL, 1.20 mmol). The resulting brown mixture was stirred at 80° C. for 20 h. The mixture was concentrated to dryness. The residue was diluted with EtOAc (100 mL), washed with 0.1 N HCl followed by brine, and the organic layer was dried over anhydrous MgSO$_4$, filtered and concentrated. The crude product was purified by flash chromatography on silica gel using 0-40% EtOAc in petroleum ether to give the title compound as a yellow solid (150 mg, 45% yield). $^1$H NMR (400 MHz, CDCl$_3$) δ 10.79 (s, 1H), 8.16 (s, 1H), 7.52 (t, 1H), 7.22 (d, 1H), 6.86 (d, 1H), 3.90 (s, 3H), 3.62 (s, 3H). HPLC: Ultimate XB-C18, 3 um, 3.0×50 mm, SN:111201514 Mobile phase: 1.0% MeCN in water (0.1% TFA) to 5% MeCN in water (0.1% TFA) in 1 min then from 5% MeCN in water (0.1% TFA) to 100% MeCN (0.1% TFA) in 5 min hold at 100% MeCN (0.1% TFA) for 2 min then back to 1% MeCN in water (0.1% TFA) at 8.01 min, and hold 2 min. Flow rate: 1.2 ml/min. Retention time 3.92 min.

Step 3: Preparation of Methyl 8-hydroxy-2-oxo-1,2-dihydroquinoline-3-carboxylate

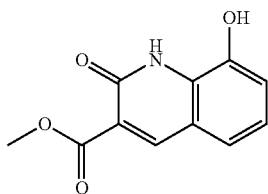 [SMILES: COC(=O)c1cc2cccc(O)c2[nH]c1=O]

To a solution of dimethyl 2-(3-hydroxy-2-nitrobenzylidene)malonate (5.0 g, 18 mmol) in MeOH (240 mL) was added $Na_2S_2O_4$ (12.4 g, 71.1 mmol). The clear solution was stirred for 5 h at 80° C. The mixture was filtered and the filtrates concentrated under reduced pressure. The residue was combined with another batch prepared using dimethyl [(E)-2-(3-hydroxy-2-nitrophenyl)ethenyl]propanedioate (3.0 g, 11 mmol) in MeOH (240 mL) and $Na_2S_2O_4$ (7.43 g, 42.7 mmol). The combined batches were purified via flash chromatography using 0-10% MeOH in DCM to give the title compound as a yellow solid (2.5 g, 40%). $^1$H NMR (400 MHz, METHANOL-d4) δ 8.62 (s, 1H), 7.26 (d, 1H), 7.06-7.16 (m, 2H), 3.90 (s, 3H). MS m/z 220 [M+H]$^+$.

Step 4: Preparation of Methyl 8-(benzyloxy)-2-oxo-1,2-dihydroquinoline-3-carboxylate

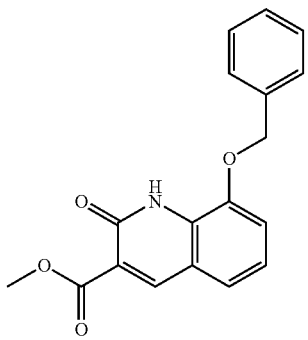 [SMILES: COC(=O)c1cc2cccc(OCc3ccccc3)c2[nH]c1=O]

To a mixture of methyl 8-hydroxy-2-oxo-1,2-dihydroquinoline-3-carboxylate (2000 mg, 9.12 mmol) in DMF (3.0 mL) was added DBU (1390 mg, 9.12 mmol). The mixture was stirred for 5 min at which time N-benzyl bromide (1560 mg, 9.12 mmol) was added and the mixture heated to 70° C. for 16 h. N-benzyl bromide (700 mg, 4 mmol) was added and the mixture was heated for 4 h. The mixture was cooled to ambient temperature. The mixture was partitioned between brine and EtOAc. Solids were collected via vacuum filtration. The aqueous phase was extracted with EtOAc. The combined organic extracts were washed with brine, dried over anhydrous $Na_2SO_4$ and concentrated under reduced pressure. The resulting residue was combined with the solid filtrate from above and was triturated with 75% EtOAc in hexanes, and filtered and dried to give the title compound as an off-white solid (1.15 g, 41% yield). $^1$H NMR (400 MHz, DMSO-d6) δ 11.16 (br s, 1H), 8.50 (s, 1H), 7.60 (d, 2H), 7.36-7.44 (m, 3H), 7.27-7.36 (m, 2H), 7.14 (t, 1H), 5.32 (s, 2H), 3.82 (s, 3H). MS m/z 310 [M+H]$^+$.

Step 5: Preparation of Methyl 8-hydroxy-2-methoxyquinoline-3-carboxylate

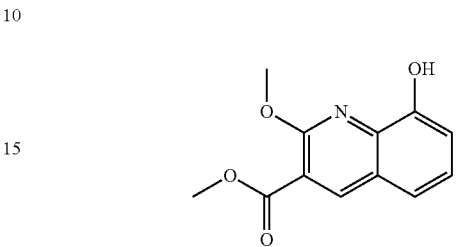

To a round bottom flask containing methyl 8-(benzyloxy)-2-oxo-1,2-dihydroquinoline-3-carboxylate (1000 mg, 3.23 mmol) was added $POCl_3$ (8.0 mL) and DMF (3 drops). The mixture was heated to 95° C. for 2 h and was then concentrated under reduced pressure. Toluene (3 mL) was added and removed under reduced pressure. To this was added a solution previously made and kept under nitrogen of sodium (850 mg of sodium in kerosene, 37 mmol, washed with hexanes to remove kerosene) in MeOH (20 mL). The mixture was heated to 65° C. overnight. The mixture was cooled to ambient temperature, and partitioned between EtOAc and 1 N HCl. The layers were separated and the aqueous phase extracted 3 times with EtOAc. The combined organic layers were dried over anhydrous $Na_2SO_4$ and concentrated under reduced pressure. The residue was purified via flash chromatography on silica gel using 0-20% EtOAc in hexanes over 5 column volumes, holding at 20% EtOAc for 4 column volumes then 20-60% EtOAc in hexanes over 2 column volumes to give a mixture of the title compound and methyl 8-(benzyloxy)-2-methoxyquinoline-3-carboxylate (0.512 g). This mixture was carried forward without further purification. $^1$H NMR (400 MHz, CDCl$_3$) δ 8.66 (s, 1H), 8.63 (s, 1H), 7.58 (d, 2H), 7.37-7.46 (m, 3H), 7.29-7.36 (m, 3H), 7.21 (d, 1H), 5.38 (s, 2H), 4.23 (s, 3H), 4.19 (s, 2H), 3.98 (s, 4H). Waters Acquity HSS T3, 2.1×50 mm, C18, 1.7 μm; Column temperature 60° C., 0.1% formic acid in water (v/v); Mobile phase B: 0.1% formic acid in MeCN (v/v) Flow-1.25 ml/min Initial conditions: A-95%: B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min. Retention time 0.81 min. MS m/z 234 [M+H]$^+$.

Step 6: Preparation of 8-Hydroxy-2-methoxyquinoline-3-carboxamide

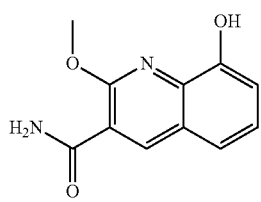 [SMILES: COc1nc2c(O)cccc2cc1C(N)=O]

To a mixture of methyl 8-hydroxy-2-methoxyquinoline-3-carboxylate (463.2 mg, 1.433 mmol) in a pressure vessel was added 7N ammonia in MeOH (2000 mg, 100 mmol, 20 mL). The vessel was sealed and the mixture heated to 70° C. overnight. The solids were collected via vacuum filtration and dried. The filtrates were concentrated under reduced pressure and purified via flash chromatography using 0-100% EtOAc in hexanes as eluent to give a mixture of the title compound and 8-(benzyloxy)-2-methoxyquinoline-3-carboxamide (164 mg, 22% yield). This mixture was carried forward without further purification. $^1$H NMR (400 MHz, CDCl$_3$) δ 8.99 (s, 1H), 8.94 (s, 1H), 7.85 (br s, 1H), 7.72 (br s, 1H), 7.50 (d, 1H), 7.43 (d, 1H), 7.22-7.38 (m, 6H), 7.10-7.17 (m, 1H), 5.81 (br s, 2H), 5.30 (s, 1H), 4.21 (s, 2H), 4.18 (s, 3H). Waters Acquity HSS T3, 2.1×50 mm, C18, 1.7 μm; Column temperature 60° C., 0.1% formic acid in water (v/v); Mobile phase B: 0.1% formic acid in MeCN (v/v) Flow-1.25 ml/min Initial conditions: A-95%:B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min. Retention time 0.74 min. MS m/z 219 [M+H]$^+$.

Step 7: Preparation of
8-Hydroxy-2-methoxyquinoline-3-carbonitrile

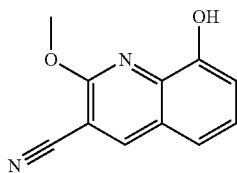

A flask containing 8-hydroxy-2-methoxyquinoline-3-carboxamide (164 mg, 0.752 mmol) was sealed with a rubber stopper, placed briefly under vacuum then purged with nitrogen. 1,4-dioxane (2 mL) and pyridine (0.49 mL, 6.01 mmol) were added. The mixture was stirred at ambient temperature for 10 min and then TFAA (631 mg, 3.01 mmol) was added dropwise, producing a slightly exothermic reaction. The mixture was stirred at ambient temperature for 3 h. The mixture was partitioned between brine and EtOAc. The layers were separated and the aqueous phase extracted with EtOAc. The combined organic extracts were washed with brine, dried over Na$_2$SO$_4$ and concentrated under reduced pressure to give a mixture of the crude title compound and 8-(benzyloxy)-2-methoxyquinoline-3-carbonitrile (169.7 mg, >100% yield). This mixture was carried forward without further purification. $^1$H NMR (400 MHz, CDCl$_3$) δ 8.48 (s, 1H), 8.43 (s, 1H), 7.58 (d, 2H), 7.38-7.49 (m, 4H), 7.31-7.38 (m, 3H), 5.39 (s, 1H), 4.25 (s, 2H), 4.23 (s, 3H). Waters Acquity HSS T3, 2.1×50 mm, C18, 1.7 μm; Column temperature 60° C., 0.1% formic acid in water (v/v); Mobile phase B: 0.1% formic acid in acetonitrile (v/v) Flow-1.25 ml/min Initial conditions: A-95%:B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min. Retention time 0.89 min. MS m/z 201 [M+H]$^+$.

Step 8: Preparation of 8-{[(2S,3S,4S)-3-Ethyl-4-fluoro-5-oxopyrrolidin-2-yl]methoxy}-2-methoxy-quinoline-3-carbonitrile

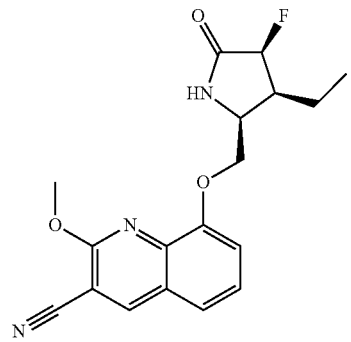 [SMILES: CC[C@@H]1[C@H](F)C(=O)N[C@@H]1COc1cccc2cc(C#N)c(OC)nc12]

To a mixture of (3S,4S,5S)-4-ethyl-3-fluoro-5-(hydroxymethyl)pyrrolidin-2-one (167 mg, 0.834 mmol) in DCM (2.0 mL) was added DIEA and methanesulfonyl chloride (197 mg, 1.71 mmol). The mixture was placed under nitrogen and stirred at ambient temperature for 2 h. The mixture was evaporated by allowing a stream of nitrogen to evaporate the DCM. To the residue was added a solution of 8-hydroxy-2-methoxyquinoline-3-carbonitrile (269 mg, 1.67 mmol) in DMF (3.0 mL) followed by K$_2$CO$_3$ (346 mg, 2.50 mmol). The mixture was heated to 50° C. overnight. K$_2$CO$_3$ (200 mg, 1.45 mmol) was added and the mixture was heated at 50° C. overnight. The reaction was incomplete and so additional mesylate was generated to complete the reaction. To a round bottom flask was added (3S,4S,5S)-4-ethyl-3-fluoro-5-(hydroxymethyl)pyrrolidin-2-one (269 mg, 1.67 mmol) in DCM, and the mixture was cooled to 0° C. DIEA and methanesulfonyl chloride (191 mg, 1.67 mmol) were added. The mixture was stirred at 0° C. for 2 h then a stream of nitrogen was passed into the flask to evaporate the DCM. The residue was dissolved in DMF and this was added to the heated reaction mixture above with additional K$_2$CO$_3$ (346 mg, 2.50 mmol). The mixture was heated at 50° C. overnight until complete by LCMS analysis. The mixture was partitioned between brine and EtOAc. The layers were separated and the aqueous phase extracted with EtOAc. The combined EtOAc extracts were washed four times with brine, dried over anhydrous Na$_2$SO$_4$ and concentrated under reduced pressure. The residue was purified via flash chromatography on silica gel using 0-100% EtOAc in hexanes as eluent to give the title compound as an off-white solid (36 mg, 12% yield). $^1$H NMR (400 MHz, CDCl$_3$) δ 8.44 (s, 1H), 7.39-7.51 (m, 2H), 7.28 (dd, 1H), 6.86 (br s, 1H), 4.95 (d, 0.5 H), 4.82 (d, 0.5H), 4.40 (d, 1H), 4.17-4.27 (m, 5H), 2.46-2.67 (m, 1H), 1.57-1.87 (m, 2H), 1.15 (t, 3H). MS m/z 344 [M+H]$^+$.

Step 9: Preparation of 8-{[(2S,3S,4S)-3-Ethyl-4-fluoro-5-oxopyrrolidin-2-yl]methoxy}-2-methoxy-quinoline-3-carboxamide To a mixture of 8-{[(2S,3S,4S)-3-ethyl-4-fluoro-5-oxopyrrolidin-2-yl]methoxy}-2-methoxyquinoline-3-carbonitrile (36 mg, 0.10 mmol) in DMSO was added K$_2$CO$_3$ (72 mg, 0.52 mmol). 30% hydrogen peroxide (83 mg, 0.73 mmol) was added. The mixture was stirred at ambient temperature for 4.5 h. The mixture was partitioned between brine and EtOAc. The layers were separated and the aqueous phase extracted with EtOAc. The combined organic extracts were washed five times with brine, dried over anhydrous Na$_2$SO$_4$ and concentrated under reduced pressure. The residue was purified via flash chromatography using 0-5% MeOH in DCM as eluent to give the title compound as an off-white solid (11 mg, 30%). $^1$H NMR (500 MHz, CDCl$_3$) δ 9.00 (s, 1H), 7.88 (br s, 1H), 7.54 (d, 1H), 7.36 (t, 1H), 7.22 (d, 1H), 7.08 (br s, 1H), 6.06 (br s, 1H), 4.92 (d, 0.5 H), 4.81 (d, 0.5 H), 4.37 (dd, 1H), 4.26 (s, 3H), 4.15-4.24 (m, 2H), 2.42-2.62 (m, 1H), 1.54-1.81 (m, 2H), 1.12 (t, 3H). MS m/z 362 [M+H]$^+$.

Example 2

4-(1,3-Oxazol-2-yl)-1-{[(2S)-5-oxopyrrolidin-2-yl]methoxy}-7-(propan-2-yloxy)isoquinoline-6-carboxamide

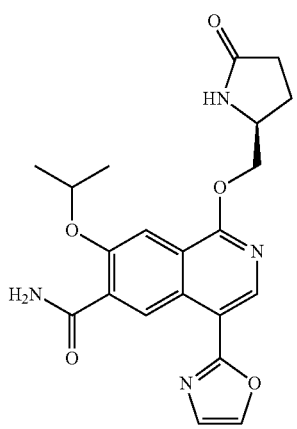 [SMILES: CC(C)Oc1cc2c(OC[C@@H]3CCC(=O)N3)ncc(-c3ncco3)c2cc1C(N)=O]

Step 1: Preparation of 1-Hydroxy-7-(propan-2-yloxy)isoquinoline-6-carbonitrile

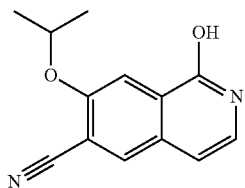 [SMILES: CC(C)Oc1cc2c(O)nccc2cc1C#N]

To 1-chloro-7-(propan-2-yloxy)isoquinoline-6-carbonitrile (500 mg, 2.03 mmol) in a sealable tube was added 1,4-dioxane (6.7 mL), followed by concentrated HCl (3.3 mL) and H$_2$O (10 mL). The mixture changed from a clear yellow solution to a thick slurry and the addition was exothermic. The tube was sealed and heated to 120° C. for 3 h. The slurry was diluted with H$_2$O and the solids collected via filtration and washed with H$_2$O to give the title compound as a yellow solid (410 mg, 88.6%). $^1$H NMR (400 MHz, DMSO-d6) δ 11.51 (br s, 1H), 8.22 (s, 1H), 7.78 (s, 1H), 7.16 (dd, 1H), 6.56 (d, 1H), 4.90 (spt, 1H), 1.37 (d, 6H). MS m/z 229 [M+H]$^+$.

Step 2: Preparation of 4-Bromo-1-hydroxy-7-(propan-2-yloxy)isoquinoline-6-carbonitrile

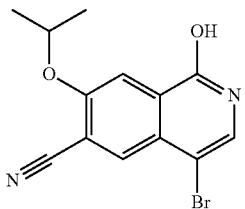 [SMILES: CC(C)Oc1cc2c(O)ncc(Br)c2cc1C#N]

A suspension of 1-hydroxy-7-(propan-2-yloxy)isoquinoline-6-carbonitrile (7.69 g, 34 mmol) in MeCN (673 mL) treated portionwise with NBS (7.26 g, 41 mmol) over a period of 5 min and the reaction mixture was stirred at 15° C. for 16 h. The reaction mixture was filtered and the solids were washed with MeCN and dried under vacuum to give the title compound as a pale green solid (2.7 g, 26%). $^1$H NMR (400 MHz, DMSO-d6) δ 11.82 (d, 1H), 8.06 (s, 1H), 7.82 (s, 1H), 7.52 (d, 1H), 4.94 (td, 1H), 1.37 (d, 6H). MS m/z 307 [M+H]$^+$.

Step 3: Preparation of 4-Bromo-1-chloro-7-(propan-2-yloxy)isoquinoline-6-carbonitrile

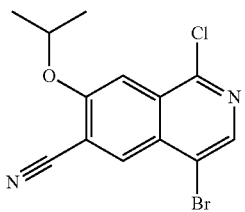 [SMILES: CC(C)Oc1cc2c(Cl)ncc(Br)c2cc1C#N]

A suspension of 4-bromo-1-hydroxy-7-(propan-2-yloxy)isoquinoline-6-carbonitrile (5800 mg, 18.9 mmol) in POCl$_3$ (180 mL) was heated to reflux for 1.5 hours. The mixture was then cooled to room temperature and the excess POCl$_3$ was removed under reduced pressure. The residue was poured onto ice and quenched by the addition of K$_2$CO$_3$. The aqueous solution was then diluted with DCM and the layers were separated. The aqueous phase was extracted with DCM and the combined organic phase was dried over Na$_2$SO$_4$, filtered and concentrated to give the title compound as an off-white solid (5.8 g, 94% yield). $^1$H NMR (400 MHz, CDCl$_3$) δ 8.50 (s, 1H), 8.43 (s, 1H), 7.66 (s, 1H), 4.91 (td, 1H), 1.54 (d, 6H). MS m/z 326 [M+H]$^+$.

Step 4: Preparation of 4-Bromo-1-{[(2S)-5-oxopyrrolidin-2-yl]methoxy}-7-(propan-2-yloxy)isoquinoline-6-carbonitrile

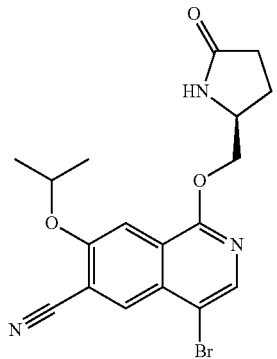 [SMILES: CC(C)Oc1cc2c(OC[C@@H]3CCC(=O)N3)ncc(Br)c2cc1C#N]

To a solution of 4-bromo-1-chloro-7-(propan-2-yloxy)isoquinoline-6-carbonitrile (2.5 g, 7.68 mmol) and (S)-5-(hydroxymethyl)pyrrolidin-2-one (1.06 g, 9.21 mmol) in THF (80 mL) at −15° C. was added 1N NaHMDS (19.2 mL, 19.2 mmol). The reaction mixture was stirred at −15° C. for 3 h then warmed to 25° C. and stirred for 16 h. The mixture was quenched with saturated NH$_4$Cl and the mixture was extracted with EtOAc. The combined organic extracts were washed with brine, dried (Na$_2$SO$_4$), filtered and concentrated. The residue was purified by flash chromatography using 0/100 to 7/93 MeOH/DCM to give the title compound as a yellow solid (1.24 g, 40% yield). $^1$H NMR (400 MHz, CDCl$_3$) δ 8.30-8.45 (m, 1H), 8.07 (s, 1H), 7.56 (s, 1H), 6.47 (br s, 1H), 4.76-4.94 (m, 1H), 4.63 (dd, 1H), 4.29-4.43 (m, 1H), 4.22 (br s, 1H), 2.29-2.56 (m, 3H), 1.87-2.13 (m, 1H), 1.34-1.56 (m, 6H). MS m/z 404 [M+H]$^+$.

Step 5: Preparation of 2-(Tributylstannanyl)-1,3-oxazole

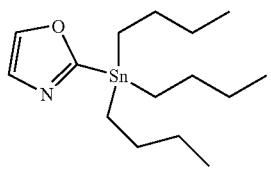 [SMILES: CCC[CH2][Sn]([CH2]CCC)([CH2]CCC)[c]1ncco1]

A solution of oxazole (1.00 g, 14.5 mmol) in THF (25 mL) at −78° C. was treated with n-BuLi (5.79 ml, 14.5 mmol, 2.5M butyllithium in hexane). After stirring for 30 min, tributyltin chloride (3.93 mL, 14.5 mmol) was added and the solution was allowed to warm to room temperature. After 1 h, the mixture was concentrated under reduced pressure. The resulting residue was treated with hexane (50 mL), and the resulting precipitate was separated by filtration through filtercel. The filtrates were concentrated under reduced pressure to give the title compound as an oil (4 g, 80%, 50% purity by NMR). This material was used without further purification.

Step 6: Preparation of 4-(1,3-Oxazol-2-yl)-1-{[(2S)-5-oxopyrrolidin-2-yl]methoxy}-7-(propan-2-yloxy)isoquinoline-6-carbonitrile A solution of 4-bromo-1-{[(2S)-5-oxopyrrolidin-2-yl]methoxy}-7-(propan-2-yloxy)isoquinoline-6-carbonitrile (404 mg, 1.0 mmol), 2-(tributylstannanyl)-1,3-oxazole (1.43 g, 2.0 mmol) and Pd(PPh$_3$)$_2$Cl$_2$ (35 mg, 0.05 mmol) in MeCN (50 mL) was stirred at 80° C. for 4 h. The solvent was evaporated and the residue was purified by flash chromatography (MeOH/DCM from 1/100 to 3.8/96.2) to give the title compound as a yellow solid (0.12 g, 31% yield). $^1$H NMR (400 MHz, CDCl$_3$) δ 9.68 (s, 1H), 8.63 (s, 1H), 7.81 (s, 1H), 7.60 (s, 1H), 7.37 (s, 1H), 6.46 (br s, 1H), 4.78-4.97 (m, 1H), 4.72 (dd, 1H), 4.47 (dd, 1H), 4.25 (br s, 1H), 2.37-2.55 (m, 3H), 2.03 (t, 1H), 1.50 (d, 6H). MS m/z 393 [M+H]$^+$.

Step 7: Preparation of 4-(1,3-Oxazol-2-yl)-1-{[(2S)-5-oxopyrrolidin-2-yl]methoxy}-7-(propan-2-yloxy)isoquinoline-6-carboxamide A mixture of 4-(1,3-oxazol-2-yl)-1-{[(2S)-5-oxopyrrolidin-2-yl]methoxy}-7-(propan-2-yloxy)isoquinoline-6-carbonitrile (60 mg, 0.15 mmol) and K$_2$CO$_3$ (106 mg, 0.76 mmol) in DMSO (4 mL) was stirred at 25° C. for 5 min. H$_2$O$_2$ (121 mg, 1.07 mmol) was added and the mixture was stirred at 25° C. for 2 h. The mixture quenched with dimethyl sulfide (95 mg, 1.53 mmol) and stirred at 25° C. for 30 min. The mixture was filtered and washed with DCM and EtOAc. The filtrate was concentrated and the residue was purified by preparative HPLC (Column: Ultimate XB-C18, 3 um, 3.0×50 mm Retention Time: 3.46 min Mobile phase: from 1% MeCN in water (0.05% TFA) to 100% MeCN in water (0.05% TFA). Flow rate: 1.2 mL/min Wavelength: 220 nm) to give crude product (30 mg, 90% purity). The crude product was stirred in MeOH (1.5 mL) for 2 min and filtered to give the title compound as a white solid (20 mg, 32% yield). $^1$H NMR (400 MHz, DMSO-d6) δ 9.43 (s, 1H), 8.57 (s, 1H), 8.32 (s, 1H), 8.17 (s, 1H), 7.78 (br s, 2H), 7.75 (s, 1H), 7.53 (s, 1H), 4.96 (td, 1H), 4.56 (dd, 1H), 4.40 (dd, 1H), 4.06 (br s, 1H), 2.17-2.38 (m, 3H), 1.94 (d, 1H), 1.41 (dd, 6H). MS m/z 433 [M+Na]$^+$.

Example 3

4-(4-Methyl-1H-imidazol-2-yl)-1-{[(2S)-5-oxopyrrolidin-2-yl]methoxy}-7-(propan-2-yloxy)isoquinoline-6-carboxamide

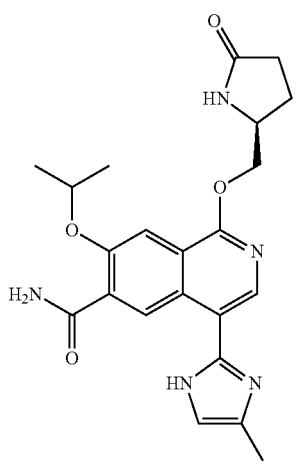

Step 1: Preparation of Tert-butyl 2-bromo-4-methyl-1H-imidazole-1-carboxylate

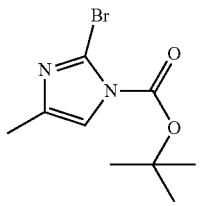

To a stirred solution of 2-bromo-4-methyl-1H-imidazole (300 mg, 1.86 mmol) and DMAP (341 mg, 2.79 mmol) in dry THF (12 mL) was added BOC$_2$O (0.43 mL, 1.86 mmol) and was stirred at room temperature for 16 h. The mixture was evaporated to dryness and diluted with EtOAc. The organic phase was washed with saturated solution of NaHCO$_3$, and then brine, dried over Na$_2$SO$_4$ and concentrated under reduced pressure. The crude was purified by flash chromatography using 8-15% EtOAc in hexane the give the title compound as an off-white solid (190 mg, 59% yield). $^1$H NMR (400 MHz, CDCl$_3$) δ 7.14 (s, 1H), 2.33 (s, 3H), 1.63 (s, 9H). MS m/z 261 [M+H]$^+$.

Step 2: Preparation of 1-{[(2S)-5-Oxopyrrolidin-2-yl]methoxy}-7-(propan-2-yloxy)-4-(4,4,5,5-tetramethyl-1,3,2-dioxaborolan-2-yl)isoquinoline-6-carbonitrile

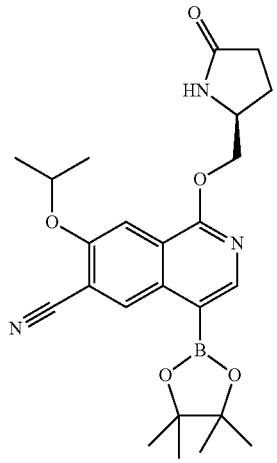 [SMILES: CC(C)Oc1cc2c(OC[C@@H]3CCC(=O)N3)ncc(B3OC(C)(C)C(C)(C)O3)c2cc1C#N]

To a stirred solution of 4-bromo-1-{[(2S)-5-oxopyrrolidin-2-yl]methoxy}-7-(propan-2-yloxy)isoquinoline-6-carboxamide (4 g, 9.9 mmol) in 1,4-dioxane (100 mL) was added freshly dried potassium acetate (2.91 g, 29.7 mmol) and bis(pinacolatodiboron) (3.52 g, 13.9 mmol). The mixture was degassed with argon for 20 min at which time tetrakis triphenylphosphine palladium (0) (572 mg, 0.49 mmol) was added and the mixture heated to 100° C. for 16 h. The mixture was cooled to room temperature and filtered through Celite. The filtrate was evaporated to dryness and purified by flash chromatography (10-20% acetone in DCM) to give 3 g of boronate ester which also contained triphenylphosphine oxide. This was further purified by trituration with 20% EtOAc in hexane (3 times) to give the title compound as a light brown solid (2.3 g, 52% yield). $^1$H NMR (400 MHz, DMSO-d6) δ 8.70-8.89 (m, 1H), 8.30 (s, 1H), 8.17 (s, 1H), 7.78 (s, 1H), 5.00 (td, 1H), 4.54 (dd, 1H), 4.32 (dd, 1H), 4.03 (br s, 1H), 2.10-2.37 (m, 3H), 1.81-1.95 (m, 1H), 1.25-1.47 (m, 18H). MS m/z 452 [M+H]$^+$.

Step 3: Preparation of 4-(4-methyl-1H-imidazol-2-yl)-1-{[(2S)-5-oxopyrrolidin-2-yl]methoxy}-7-(propan-2-yloxy)isoquinoline-6-carbonitrile

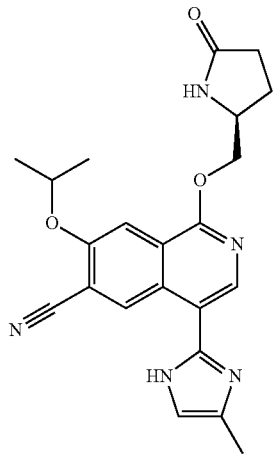 [SMILES: Cc1c[nH]c(-c2cnc(OC[C@@H]3CCC(=O)N3)c3cc(OC(C)C)c(C#N)cc23)n1]

1-{[(2S)-5-Oxopyrrolidin-2-yl]methoxy}-7-(propan-2-yloxy)-4-(4,4,5,5-tetramethyl-1,3,2-dioxaborolan-2-yl)isoquinoline-6-carbonitrile (150 mg, 0.33 mmol), tert-butyl 2-bromo-4-methyl-1H-imidazole-1-carboxylate (104.17 mg, 0.39 mmol) and K$_2$CO$_3$ (114.74 mg, 0.83 mmol) were dissolved in dioxane/H$_2$O (3 mL of a 4:1 mixture) and was degassed with argon for 10 min. Pd(dppf)Cl$_2$.DCM (13.57 mg, 0.017 mmol) was added and the mixture was again degassed for 5 min. The mixture was heated to 100° C. for 16 h. The mixture was diluted with EtOAc and was washed with water, brine, dried over Na$_2$SO$_4$ and concentrated. The crude material was purified by preparative TLC (5% MeOH/DCM) to give the title compound as a solid (42 mg, 31% yield). $^1$H NMR (400 MHz, DMSO-d6) δ 12.7 (d, 1H), 9.78 (d, 1H), 8.32 (s, 1H), 8.17 (s, 1H), 7.78 (s, 1H), 7.05 (s, 0.5H), 6.88 (s, 0.5H), 5.02 (td, 1H), 4.53 (dd, 1H), 4.32 (dd, 1H), 4.05 (br s, 1H), 2.20-2.32 (m, 6H), 1.91 (m, 1H), 1.40-1.44 (m, 6H). MS m/z 406 [M+H]$^+$.

Step 4: Preparation of 4-(4-Methyl-1H-imidazol-2-yl)-1-{[(2S)-5-oxopyrrolidin-2-yl]methoxy}-7-(propan-2-yloxy)isoquinoline-6-carboxamide A stirred solution of 4-(4-methyl-1H-imidazol-2-yl)-1-{[(2S)-5-oxopyrrolidin-2-yl]methoxy}-7-(propan-2-yloxy)isoquinoline-6-carbonitrile (60 mg, 0.15 mmol) in DMSO (1.0 mL) was treated with finely powdered K$_2$CO$_3$ (81.8 mg, 0.59 mmol) and the resulting mixture was heated to 45° C. To this solution was slowly added 30% H$_2$O$_2$ (0.19 mL, 1.93 mmol) dropwise. After 45 min the reaction mixture was diluted with MeOH, filtered and washed with MeOH. The filtrate was evaporated under reduced pressure. The crude material was purified by preparative HPLC to give the title compound as a yellow solid (8 mg, 13% yield). $^1$H NMR (400 MHz, DMSO-d6) δ 12.28 (br s, 1H), 9.19-9.42 (m, 2H), 8.15 (d, 2H), 7.72 (br s, 2H), 7.68 (s, 1H), 6.81-7.03 (m, 1H), 4.93 (td, 1H), 4.51 (dd, 1H), 4.36 (dd, 1H), 4.05 (br s, 1H), 2.18-2.31 (m, 5H), 1.89-1.99 (m, 1H), 1.40 (dd, 6H). MS m/z 424 [M+H]$^+$.

Example 4

4-(1-Methyl-1H-pyrazol-3-yl)-1-{[(2S)-5-oxopyrrolidin-2-yl]methoxy}-7-(propan-2-yloxy)isoquinoline-6-carboxamide

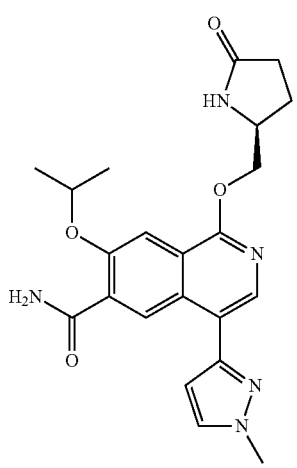 [SMILES: CC(C)Oc1cc2c(OC[C@@H]3CCC(=O)N3)ncc(-c3ccn(C)n3)c2cc1C(N)=O]

Step 1: Preparation of 4-(1-Methyl-1H-pyrazol-3-yl)-1-{[(2S)-5-oxopyrrolidin-2-yl]methoxy}-7-(propan-2-yloxy)isoquinoline-6-carbonitrile

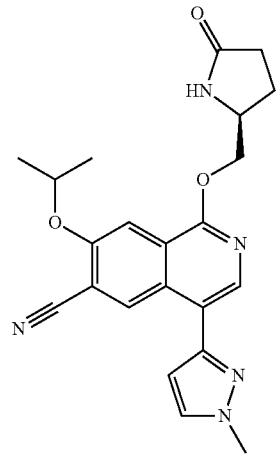 [SMILES: CC(C)Oc1cc2c(OC[C@@H]3CCC(=O)N3)ncc(-c3ccn(C)n3)c2cc1C#N]

1-{[(2S)-5-Oxopyrrolidin-2-yl]methoxy}-7-(propan-2-yloxy)-4-(4,4,5,5-tetramethyl-1,3,2-dioxaborolan-2-yl)isoquinoline-6-carbonitrile (100 mg, 0.22 mmol), 3-iodo-1-methyl-1H-pyrazole (55.34 mg, 0.26 mmol) and K$_2$CO$_3$ (76.5 mg, 0.54 mmol) were dissolved in dioxane/H$_2$O (2 mL, 4:1) and degassed with argon for 10 min. Pd(dppf)Cl$_2$.DCM (9.04 mg, 0.012 mmol) was added and the reaction mixture and was again degassed for 5 min. The mixture was heated to 100° C. for 16 h. The mixture was diluted with EtOAc and was washed with water, brine, dried over Na$_2$SO$_4$ and concentrated. The crude was purified by silica gel column chromatography (4% MeOH/DCM) to obtain the title compound as a brown solid (90 mg, ~100% yield) which was contaminated with an impurity. This material was used in next step without further purification. MS m/z 406 [M+H]$^+$.

Step 2: Preparation of 4-(1-Methyl-1H-pyrazol-3-yl)-1-{[(2S)-5-oxopyrrolidin-2-yl]methoxy}-7-(propan-2-yloxy)isoquinoline-6-carboxamide A stirred solution of 4-(1-methyl-1H-pyrazol-3-yl)-1-{[(2S)-5-oxopyrrolidin-2-yl]methoxy}-7-(propan-2-yloxy)isoquinoline-6-carbonitrile (90.0 mg, 0.22 mmol) in DMSO (1.0 mL) was treated with finely powdered K$_2$CO$_3$ (122.66 mg, 0.88 mmol) and the mixture was heated to 45° C. A 30% H$_2$O$_2$ (0.29 ml, 2.88 mmol) solution was added slowly dropwise to the reaction mixture. After 45 min the reaction mixture was diluted with MeOH, filtered and washed with MeOH. The filtrate was evaporated under reduced pressure. The crude was purified by preparative HPLC to give the title compound as an off white solid (12 mg, 13% yield). $^1$H NMR (400 MHz, DMSO-d6) δ 8.88 (s, 1H), 8.11 (s, 1H), 8.07 (s, 1H), 7.85 (s, 1H), 7.64-7.76 (m, 3H), 6.61 (s, 1H), 4.94 (td, 1H), 4.50 (dd, 1H), 4.36 (dd, 1H), 4.05 (br s, 1H), 3.96 (s, 3H), 2.14-2.36 (m, 3H), 1.88-1.97 (m, 1H), 1.41 (t, 6H). MS m/z 424 [M+H]$^+$.

Example 5

4-(1-methyl-1H-pyrazol-4-yl)-1-{[(2S)-5-oxopyrrolidin-2-yl]methoxy}-7-(propan-2-yloxy)isoquinoline-6-carboxamide

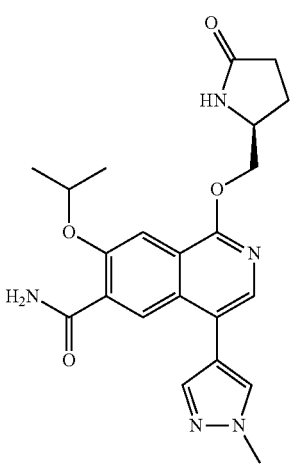 [SMILES: CC(C)Oc1cc2c(OC[C@@H]3CCC(=O)N3)ncc(-c3cnn(C)c3)c2cc1C(N)=O]

Step 1: Preparation of 4-(1-Methyl-1H-pyrazol-4-yl)-1-{[(2S)-5-oxopyrrolidin-2-yl]methoxy}-7-(propan-2-yloxy)isoquinoline-6-carbonitrile

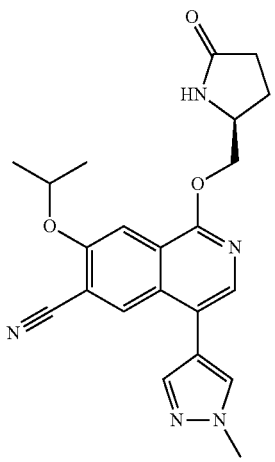 [SMILES: CC(C)Oc1cc2c(OC[C@@H]3CCC(=O)N3)ncc(-c3cnn(C)c3)c2cc1C#N]

1-{[(2S)-5-Oxopyrrolidin-2-yl]methoxy}-7-(propan-2-yloxy)-4-(4,4,5,5-tetramethyl-1,3,2-dioxaborolan-2-yl)isoquinoline-6-carbonitrile (100 mg, 0.22 mmol), 4-bromo-1-methyl-1H-pyrazole (42.57 mg, 0.26 mmol) and $K_2CO_3$ (76.49 mg, 0.55 mmol) were dissolved in dioxane/$H_2O$ (2 mL, 4:1) and the mixture was was degassed with argon for 10 min. Pd(dppf)$Cl_2$.DCM (9.05 mg, 0.01 mmol) was added, and the mixtures was degassed for 5 min. The reaction mixture was heated to 100° C. for 16 h. The mixture was cooled to room temperature, diluted with EtOAc and was washed with water, brine, dried over $Na_2SO_4$ and concentrated. The crude material was purified by silica gel column chromatography (0-4% MeOH/DCM) to give the title compound as an off white solid (75 mg, ~84% yield) which contained an impurity and was used in next step without further purification. MS m/z 406 [M+H]$^+$.

Step 2: Preparation of 4-(1-methyl-1H-pyrazol-4-yl)-1-{[(2S)-5-oxopyrrolidin-2-yl]methoxy}-7-(propan-2-yloxy)isoquinoline-6-carboxamide A stirred solution of 4-(1-methyl-1H-pyrazol-4-yl)-1-{[(2S)-5-oxopyrrolidin-2-yl]methoxy}-7-(propan-2-yloxy)isoquinoline-6-carbonitrile (75.0 mg, 0.18 mmol) in DMSO (1.0 ml) was treated with finely powdered $K_2CO_3$ (102 mg, 0.74 mmol) and was heated to 45° C. This solution was slowly treated with 30% $H_2O_2$ (0.24 ml, 2.41 mmol) solution drop wise. After 45 min the reaction mixture was diluted with methanol and filtered and washed with methanol. The filtrate was evaporated under reduced pressure. The crude was purified by preparative HPLC to give the title compound as an off white solid (14 mg, 18% yield). $^1$H NMR (400 MHz, DMSO-d6) δ 8.30 (s, 1H), 8.11 (s, 1H), 8.02 (s, 1H), 7.85 (s, 1H), 7.74 (br s, 2H), 7.72 (s, 1H), 7.68 (s, 1H), 4.95 (td, 1H), 4.49 (dd, 1H), 4.34 (dd, 1H), 3.95 (s, 3H), 2.18-2.36 (m, 3H), 1.93 (d, 1H), 1.38-1.44 (m, 6H). MS m/z 424 [M+H]$^+$.

Example 6

4-(4-Methyl-1,3-oxazol-2-yl)-1-{[(2S)-5-oxopyrrolidin-2-yl]methoxy}-7-(propan-2-yloxy)isoquinoline-6-carboxamide

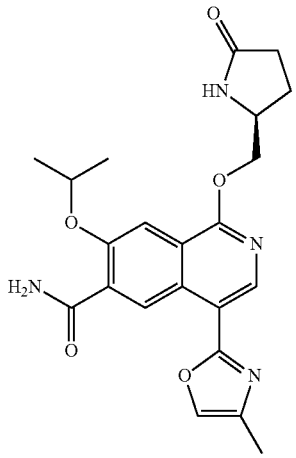 [SMILES: Cc1coc(-c2cnc(OC[C@@H]3CCC(=O)N3)c3cc(OC(C)C)c(C(N)=O)cc23)n1]

Step 1: Preparation of 4-Methyl-2-(tributylstannanyl)-1,3-oxazole

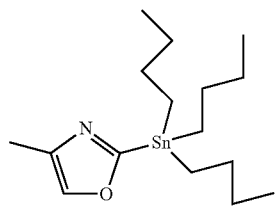 [SMILES: CCC[CH2][Sn]([CH2]CCC)([CH2]CCC)[c]1nc(C)co1]

A solution of 4-methyloxazole (1.00 g, 12 mmol) in THF (30 mL) at −78° C. was treated with n-BuLi (4.81 mL, 12 mmol, 2.5M in hexane). After 30 min, an addition of tributyltin chloride (3.92 g, 12 mmol) was made and the solution was allowed to warm to room temperature. Stirring was continued for another hour, after which most of the solvents were evaporated in vacuo. The resulting residue was taken up in hexane (50 mL) and the resulting precipitate was collected by filtration. The filtrate was evaporated to give the title compound as an oil (4 g, 89%, 60% purity by NMR). This material was used without further purification. $^1$H NMR (400 MHz, CDCl$_3$) δ 7.53 (s, 1H), 2.21 (s, 3H), 1.68-1.58 (m, 10H), 1.36-1.32 (m, 9H). 1.21-1.71 (m, 8H), 0.92-0.88 (m, 14H). NMR indicates the presence of tributyltin chloride.

Step 2: Preparation of 4-(4-Methyl-1,3-oxazol-2-yl)-1-{[(2S)-5-oxopyrrolidin-2-yl]methoxy}-7-(propan-2-yloxy)isoquinoline-6-carbonitrile

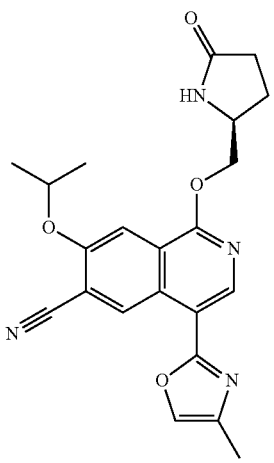 [SMILES: Cc1coc(-c2cnc(OC[C@@H]3CCC(=O)N3)c3cc(OC(C)C)c(C#N)cc23)n1]

A solution of 4-bromo-1-{[(2S)-5-oxopyrrolidin-2-yl]methoxy}-7-(propan-2-yloxy)isoquinoline-6-carbonitrile (300 mg, 0.742 mmol), 4-methyl-2-(tributylstannanyl)-1,3-oxazole (1.7 g, 2.7 mmol) and trans-dichlorobis(triphenylphosphine)palladium(II) (52 mg, 0.10 mmol) in MeCN (50 mL) was stirred at 80° C. for 16 hours. The solvent was evaporated and the residue was purified by flash chromatography over silica gel (MeOH/DCM from 0/100 to 4/96) to give the title compound as a yellow solid (140 mg, 46% yield). $^1$H NMR (400 MHz, CDCl$_3$) δ 9.67 (s, 1H), 8.57 (s, 1H), 7.61 (s, 1H), 7.50 (s, 1H), 6.77 (br s, 1H), 4.88 (td, 1H), 4.69 (dd, 1H), 4.44 (dd, 1H), 4.24 (br s, 1H), 2.37-2.55 (m, 3H), 2.32 (s, 3H), 1.92-2.13 (m, 1H), 1.44-1.57 (m, 6H). MS m/z 429 [M+Na]$^+$.

Step 3: Preparation of 4-(4-Methyl-1,3-oxazol-2-yl)-1-{[(2S)-5-oxopyrrolidin-2-yl]methoxy}-7-(propan-2-yloxy)isoquinoline-6-carboxamide A mixture of 4-(4-methyl-1,3-oxazol-2-yl)-1-{[(2S)-5-oxopyrrolidin-2-yl]methoxy}-7-(propan-2-yloxy)isoquinoline-6-carboxamide (80 mg, 0.20 mmol) and K$_2$CO$_3$ (136 mg, 0.98 mmol) in DMSO (4 mL) was stirred at 25° C. for 5 min. H$_2$O$_2$ (156 mg, 1.38 mmol) was added. The reaction mixture was stirred at 25° C. for 2 h. The mixture was quenched with dimethyl sulfide (122 mg, 1.97 mmol) and stirred at 25° C. for 30 min. The mixture was filtered and washed with DCM and EtOAc. The filter cake was suspended in MeOH (2 mL) and stirred for 2 h. The mixture was filtered and the filter cake was suspended in MeOH/DCM (1/10, 5 mL) and stirred for 5 min. The mixture was filtered and the filtrate was concentrated to give the title compound as an off-white solid (23 mg, 28%). $^1$H NMR (400 MHz, DMSO-d6) δ 9.34 (s, 1H), 8.53 (s, 1H), 8.16 (s, 1H), 8.00 (s, 1H), 7.79 (br s, 1H), 7.74 (s, 2H), 4.86-5.02 (m, 1H), 4.55 (d, 1H), 4.39 (dd, 1H), 4.06 (br s, 1H), 2.13-2.40 (m, 6H), 1.93 (br s, 1H), 1.40 (dd, 6H). MS m/z 425 [M+H]$^+$.

Example 7

4-(4,5-Dimethyl-1,3-oxazol-2-yl)-1-{[(2S)-5-oxopyrrolidin-2-yl]methoxy}-7-(propan-2-yloxy)isoquinoline-6-carboxamide

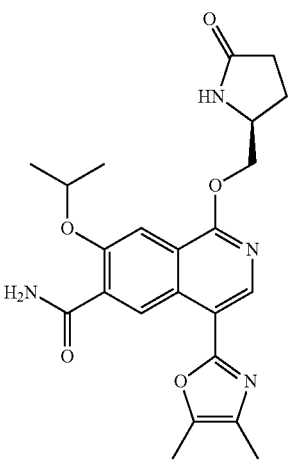 [SMILES: Cc1nc(-c2cnc(OC[C@@H]3CCC(=O)N3)c3cc(OC(C)C)c(C(N)=O)cc23)oc1C]

Step 1: Preparation of Methyl 6-cyano-1-{[(2S)-5-oxopyrrolidin-2-yl]methoxy}-7-(propan-2-yloxy)isoquinoline-4-carboxylate

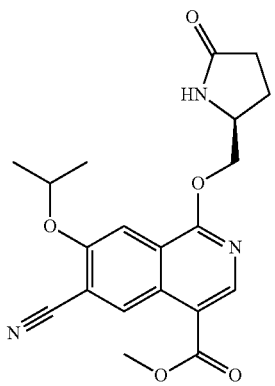 [SMILES: COC(=O)c1cnc(OC[C@@H]2CCC(=O)N2)c2cc(OC(C)C)c(C#N)cc12]

A mixture of 4-bromo-1-{[(2S)-5-oxopyrrolidin-2-yl]methoxy}-7-(propan-2-yloxy)isoquinoline-6-carbonitrile (6.5 g, 16.08 mmol), TEA (4.88 g, 48.2 mmol) and Pd(dppf)$_2$Cl$_2$ (1.18 g, 1.61 mmol) in MeOH (500 mL) was stirred under CO (50 psi) at 80° C. for 16 h. The mixture was filtered and the solvent was evaporated. The residue was purified by flash chromatography over silica gel (MeOH/DCM from 0/100 to 5/95) to give the title compound as a yellow solid (5.3 g, 86% yield). $^1$H NMR (400 MHz, CDCl$_3$) δ 9.36 (s, 1H), 8.70 (s, 1H), 7.58 (s, 1H), 6.29 (br s, 1H), 4.85

(td, 1H), 4.72 (dd, 1H), 4.48 (dd, 1H), 4.23 (br s, 1H), 4.00 (s, 3H), 2.31-2.53 (m, 3H), 1.93-2.15 (m, 1H), 1.49 (d, 6H). MS m/z 406 [M+Na]$^+$.

Step 2: Preparation of 6-Cyano-1-{[(2S)-5-oxopyrrolidin-2-yl]methoxy}-7-(propan-2-yloxy)isoquinoline-4-carboxylic acid

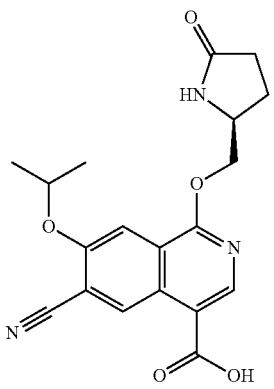 [SMILES: CC(C)Oc1cc2c(OC[C@@H]3CCC(=O)N3)ncc(C(=O)O)c2cc1C#N]

A mixture of methyl 6-cyano-1-{[(2S)-5-oxopyrrolidin-2-yl]methoxy}-7-(propan-2-yloxy)isoquinoline-4-carboxylate (5.2 g, 13.56 mmol) and LiOH.H$_2$O (1.71 g, 40.7 mmol) in H$_2$O (20 mL), EtOH (20 mL) and THF (80 mL) was stirred at 20° C. for 3 h. The mixture was acidified with 1N HCl to pH 7 and the solvent was evaporated. To the residue was added NaHCO$_3$ (2 g) in H$_2$O (100 mL) and the mixture stirred for 15 min. The mixture was washed with DCM and the water phase was acidified with 1N HCl to pH 6. The mixture was filtered to give the title compound as an off-white solid (3.4 g, 68% yield). $^1$H NMR (400 MHz, DMSO-d6) δ 9.35 (s, 1H), 8.65 (s, 1H), 8.20 (s, 1H), 7.80 (s, 1H), 4.91-5.14 (m, 1H), 4.52-4.74 (m, 1H), 4.37 (dd, 1H), 3.89-4.18 (m, 1H), 2.12-2.36 (m, 3H), 1.91 (br s, 1H), 1.41 (dd, 6H). MS m/z 370 [M+H]$^+$.

Step 3: Preparation of 6-Cyano-N-(3-oxobutan-2-yl)-1-{[(2S)-5-oxopyrrolidin-2-yl]methoxy}-7-(propan-2-yloxy)isoquinoline-4-carboxamide

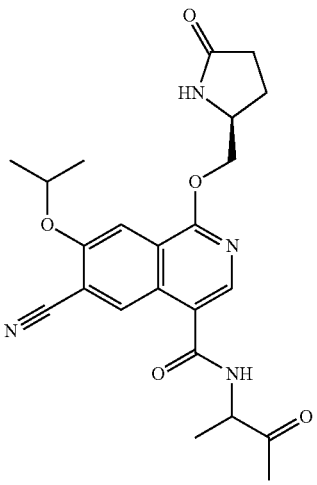 [SMILES: CC(=O)C(C)NC(=O)c1cnc(OC[C@@H]2CCC(=O)N2)c2cc(OC(C)C)c(C#N)cc12]

To a solution of 6-cyano-1-{[(2S)-5-oxopyrrolidin-2-yl]methoxy}-7-(propan-2-yloxy)isoquinoline-4-carboxylic acid (300 mg, 0.81 mmol) and DIEA (315 mg, 2.4 mmol) in DMF (0.5 mL) and DCM (30 mL) was added 3-aminobutan-2-one (100 mg, 0.81 mmol) and HATU (463 mg, 1.2 mmol). The reaction mixture was stirred at 20° C. for 3 h. The solvent was evaporated and the residue was purified by flash chromatography over silica gel (MeOH/DCM from 0/100 to 4/96) to give the title compound as an off-white solid (200 mg, 56% yield). MS m/z 370 [M+H]$^+$.

Step 4: Preparation of 4-(4,5-Dimethyl-1,3-oxazol-2-yl)-1-{[(2S)-5-oxopyrrolidin-2-yl]methoxy}-7-(propan-2-yloxy)isoquinoline-6-carbonitrile

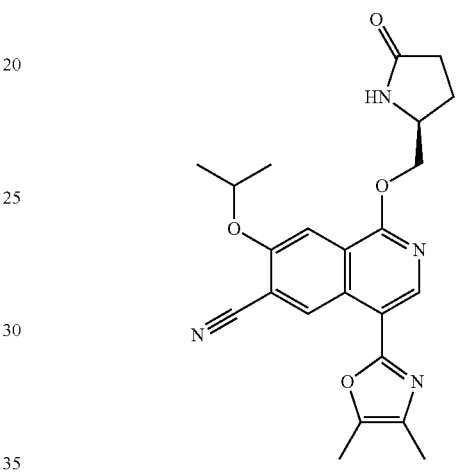

To a mixture of 6-cyano-N-(3-oxobutan-2-yl)-1-{[(2S)-5-oxopyrrolidin-2-yl]methoxy}-7-(propan-2-yloxy)isoquinoline-4-carboxamide (130 mg, 0.30 mmol) in 1,2-dichloroethane (30 mL) at 0° C. was added DIEA (1 mL) and TFAA (1 mL). The reaction mixture was allowed to warm to 20° C. and stirred for 2 h. The solvent was evaporated and the residue was purified by flash chromatography over silica gel (MeOH/DCM from 0/100 to 4/96) to give the title compound as a yellow solid (110 mg, 88% yield). $^1$H NMR (400 MHz, CDCl$_3$) δ 9.65 (s, 1H), 8.54 (s, 1H), 7.59 (s, 1H), 7.04 (br s, 1H), 4.87 (td, 1H), 4.75 (dd, 1H), 4.45 (dd, 1H), 4.21-4.35 (m, 1H), 2.40-2.58 (m, 3H), 2.38 (s, 3H), 2.23 (s, 3H), 1.97-2.09 (m, 1H), 1.50 (dd, 6H). MS m/z 443 [M+Na]$^+$.

Step 5: Preparation of 4-(4,5-Dimethyl-1,3-oxazol-2-yl)-1-{[(2S)-5-oxopyrrolidin-2-yl]methoxy}-7-(propan-2-yloxy)isoquinoline-6-carboxamide A mixture of 4-(4,5-dimethyl-1,3-oxazol-2-yl)-1-{[(2S)-5-oxopyrrolidin-2-yl]methoxy}-7-(propan-2-yloxy)isoquinoline-6-carbonitrile (100 mg, 0.238 mmol) and K$_2$CO$_3$ (164 mg, 1.19 mmol) in DMSO (4 mL) was stirred at 25° C. for 5 min. H$_2$O$_2$ (189 mg, 1.66 mmol) was added and the reaction mixture was stirred at 25° C. for 2 h. The mixture was quenched with dimethyl sulfide (148 mg, 2.38 mmol) and stirred at 25° C. for 30 min. The mixture was filtered and washed with DCM and EtOAc. The filtrate was concentrated and the residue was purified by preparative HPLC (Column: DIKMA Diamonsil(2) C18 200*20 mm*5 um Mobile phase: from 24% MeCN in water (0.225% FA) to 44%

MeCN in water (0.225% FA) Flow rate: 30 mL/min Wavelength: 220 nm) to give the title compound as a yellow solid (23 mg, 22% yield) as a yellow solid. $^1$H NMR (400 MHz, DMSO-d6) δ 9.36 (s, 1H), 8.47 (s, 1H), 8.15 (s, 1H), 7.77 (br s, 1H), 7.72 (s, 1H), 4.90-4.97 (m, 1H), 4.54 (d, 1H), 4.38 (dd, 1H), 4.05 (br s, 1H), 2.36 (s, 3H), 2.19-2.34 (m, 3H), 2.17 (s, 3H), 1.94 (d, 1H), 1.40 (dd, 6H). One NH obscured. MS m/z 439 [M+H]$^+$.

Example 8

4-[4-(Hydroxymethyl)-1H-imidazol-2-yl]-1-{[(2S)-5-oxopyrrolidin-2-yl]methoxy}-7-(propan-2-yloxy)isoquinoline-6-carboxamide

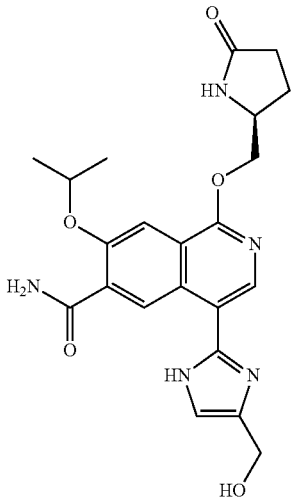 [SMILES: CC(C)Oc1cc2c(OC[C@@H]3CCC(=O)N3)ncc(-c3nc(CO)c[nH]3)c2cc1C(N)=O]

Step 1: Preparation of 2-Iodo-4-({[tri(propan-2-yl)silyl]oxy}methyl)-1H-imidazole

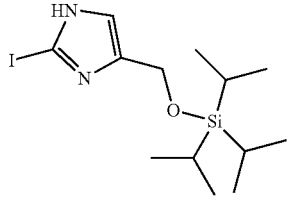 [SMILES: CC(C)[Si](OCc1c[nH]c(I)n1)(C(C)C)C(C)C]

To a stirred solution of (2-iodo-1H-imidazol-4-yl)methanol (250 mg, 1.14 mmol) and imidazole (155 mg, 2.28 mmol) in DMF (5 mL) was added triisopropylsilyl chloride (0.29 mL, 1.37 mmol). The mixture was stirred at room temperature for 16 h. The mixture was diluted with EtOAc and was washed with water, brine, dried over Na$_2$SO$_4$ and concentrated under reduced pressure. The crude was purified by column chromatography (10-30% EtOAc in hexane) to give the title compound as an off white solid (400 mg, 92% yield). $^1$H NMR (400 MHz, DMSO-d6) δ 12.62-12.45 (m, 1H), 7.02-6.75 (m, 1H), 4.64-4.53 (m, 2H), 1.17-1.07 (m, 3H), 1.06-0.95 (m, 18H). MS m/z 382 [M+H]$^+$.

Step 2: Preparation of Tert-butyl 2-iodo-4-({[tri(propan-2-yl)silyl]oxy}methyl)-1H-imidazole-1-carboxylate

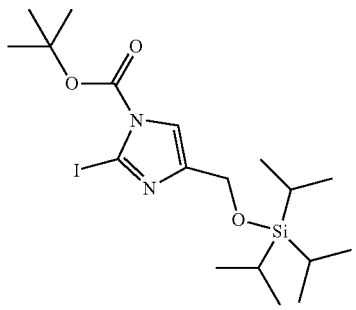 [SMILES: CC(C)[Si](OCc1cn(C(=O)OC(C)(C)C)c(I)n1)(C(C)C)C(C)C]

To a stirred solution of 2-iodo-4-({[tri(propan-2-yl)silyl]oxy}methyl)-1H-imidazole (400 mg, 1.05 mmol) and DMAP (193 mg, 1.58 mmol) in dry THF (20 mL) was added BOC$_2$O (0.242 mL, 1.05 mmol) and the mixture was stirred at room temperature for 16 h. The mixture was evaporated to dryness and diluted with EtOAc. The organic phase was washed with 0.5N HCl solution, saturated aqueous solution of NaHCO$_3$, water, brine, dried over Na$_2$SO$_4$ and concentrated to give the title compound as a light yellow semisolid (500 mg, 99% yield). $^1$H NMR (400 MHz, DMSO-d6) δ 7.43 (s, 1H), 4.55 (s, 2H), 1.58 (s, 9H), 1.02-0.94 (m, 18H).

Step 3: Preparation of 1-{[(2S)-5-Oxopyrrolidin-2-yl]methoxy}-7-(propan-2-yloxy)-4-[4-({[tri(propan-2-yl)silyl]oxy}methyl)-1H-imidazol-2-yl]isoquinoline-6-carbonitrile

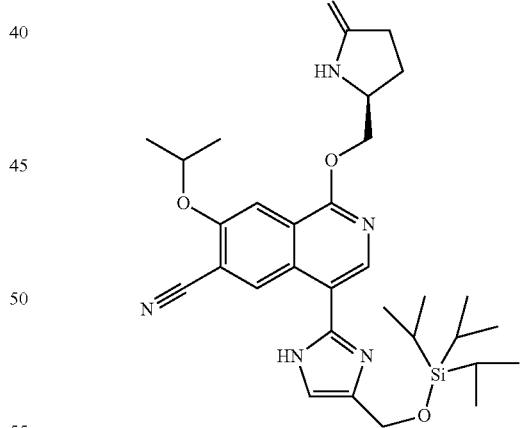

1-{[(2S)-5-Oxopyrrolidin-2-yl]methoxy}-7-(propan-2-yloxy)-4-(4,4,5,5-tetramethyl-1,3,2-dioxaborolan-2-yl)isoquinoline-6-carbonitrile (200 mg, 0.44 mmol), tert-butyl 2-iodo-4-({[tri(propan-2-yl)silyl]oxy}methyl)-1H-imidazole-1-carboxylate (255 mg, 0.53 mmol) and K$_2$CO$_3$ (153 mg, 1.11 mmol) were dissolved in dioxane/H$_2$O (3.0 mL, 4:1) and was degassed with argon for 10 min. Pd(dppf)Cl$_2$.DCM (18 mg, 0.02 mmol) was added, and the reaction mixture was degassed for 5 min. The reaction mixture was heated to 100° C. for 16 h. The reaction mixture was cooled to room temperature and diluted with EtOAc, washed with water, brine, dried over Na₂SO₄ and was concentrated. The crude was purified by column chromatography (2% MeOH/DCM) to give the title compound (150 mg, ~59% yield). This material also contained some impurity along with desired compound and was used in next step without further purification. MS m/z 578 [M+H]⁺.

Step 4: Preparation of 4-[4-(Hydroxymethyl)-1H-imidazol-2-yl]-1-{[(2S)-5-oxopyrrolidin-2-yl]methoxy}-7-(propan-2-yloxy)isoquinoline-6-carbonitrile

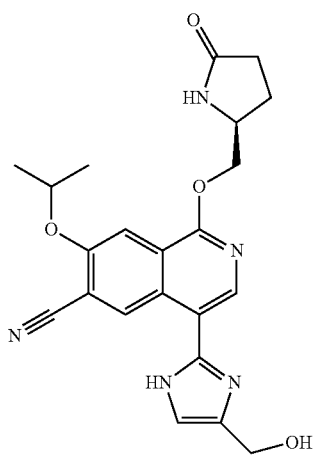 [SMILES: CC(C)Oc1cc2c(OC[C@@H]3CCC(=O)N3)ncc(-c3nc(CO)c[nH]3)c2cc1C#N]

To a stirred solution of 1-{[(2S)-5-Oxopyrrolidin-2-yl]methoxy}-7-(propan-2-yloxy)-4-[4-({[tri(propan-2-yl)silyl]oxy}methyl)-1H-imidazol-2-yl]isoquinoline-6-carbonitrile (147 mg, 0.25 mmol) in THF (2 mL) was added TBAF [1M in THF] (0.38 mL, 0.38 mmol) at 0° C. and the mixture was stirred at room temperature for 1 h. The mixture was diluted with EtOAc and washed with water, brine, dried over Na₂SO₄ and concentrated under reduced pressure. The crude was purified by silica gel column chromatography (5-10% MeOH/DCM) to give the title compound as a brown solid (95 mg, 88% yield). MS m/z 422 [M+H]⁺.

Step 5: Preparation of 4-[4-(Hydroxymethyl)-1H-imidazol-2-yl]-1-{[(2S)-5-oxopyrrolidin-2-yl]methoxy}-7-(propan-2-yloxy)isoquinoline-6-carboxamide A stirred solution of 4-[4-(hydroxymethyl)-1H-imidazol-2-yl]-1-{[(2S)-5-oxopyrrolidin-2-yl]methoxy}-7-(propan-2-yloxy)isoquinoline-6-carbonitrile (95 mg, 0.23 mmol) in DMSO (2 mL) was treated with finely powdered K₂CO₃ (125 mg, 0.90 mmol) and was heated to 45° C. 30% H₂O₂ (0.30 mL, 2.93 mmol) solution was added slowly dropwise. After 45 min the mixture was diluted with MeOH and filtered and washed with MeOH. The filtrate was evaporated under reduced pressure. The crude material was purified by preparative HPLC to give the title compound as a yellow solid (7 mg, 7% yield). ¹H NMR (400 MHz, METHANOL-d4) δ 8.83 (s, 1H), 8.09 (s, 1H), 7.79 (s, 1H), 7.20 (br s, 1H), 4.99 (td, 1H), 4.67 (s, 1H), 4.52-4.66 (m, 2H), 4.24 (br s, 1H), 2.37-2.60 (m, 3H), 2.06-2.18 (m, 1H), 1.50 (t, 6H). One proton obscured by a solvent peak. MS m/z 440 [M+H]⁺.

Example 9

4-(5-Methyl-1,3-oxazol-2-yl)-1-{[(2S)-5-oxopyrrolidin-2-yl]methoxy}-7-(propan-2-yloxy)isoquinoline-6-carboxamide

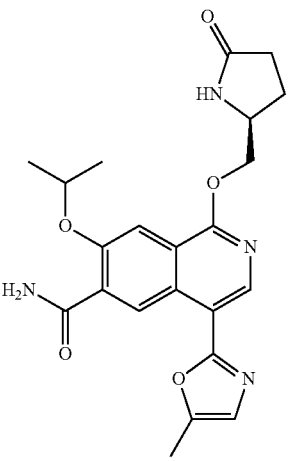 [SMILES: Cc1cnc(-c2cnc(OC[C@@H]3CCC(=O)N3)c3cc(OC(C)C)c(C(N)=O)cc23)o1]

Step 1: Preparation of 6-Cyano-N-(2-oxopropyl)-1-{[(2S)-5-oxopyrrolidin-2-yl]methoxy}-7-(propan-2-yloxy)isoquinoline-4-carboxamide

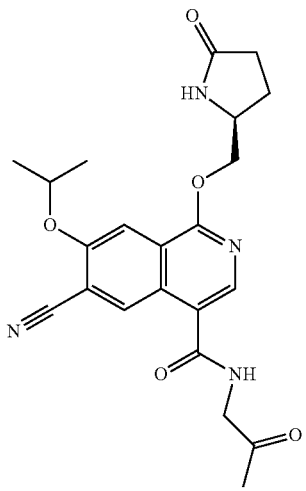 [SMILES: CC(=O)CNC(=O)c1cnc(OC[C@@H]2CCC(=O)N2)c2cc(OC(C)C)c(C#N)cc12]

To a solution of 6-cyano-1-{[(2S)-5-oxopyrrolidin-2-yl]methoxy}-7-(propan-2-yloxy)isoquinoline-4-carboxylic acid (200 mg, 0.541 mmol) and DIEA (210 mg, 1.62 mmol) in DMF (2 mL) and DCM (20 mL) was added 1-aminopropan-2-one (59.3 mg, 0.541 mmol) and HATU (309 mg, 0.812 mmol). The reaction mixture was stirred at 20° C. for 3 h. The solvent was evaporated and the residue was purified by flash chromatography over silica gel (MeOH/DCM from 0/100 to 4/96) to give the title compound as an off-white solid 10 (150 mg, 65% yield). ¹H NMR (400 MHz, CDCl₃) δ 8.81 (s, 1H), 8.20 (s, 1H), 7.55 (s, 1H), 6.85 (br s, 1H), 6.34 (br s, 1H), 4.84 (td, 1H), 4.68 (dd, 1H), 4.38-4.49 (m, 3H), 4.23 (br s, 1H), 2.37-2.54 (m, 3H), 2.33 (s, 3H), 1.95-2.12 (m, 1H), 1.48 (d, 6H). MS m/z 447 [M+Na]⁺.

Step 2: Preparation of 4-(5-Methyl-1,3-oxazol-2-yl)-1-{[(2S)-5-oxopyrrolidin-2-yl]methoxy}-7-(propan-2-yloxy)isoquinoline-6-carbonitrile

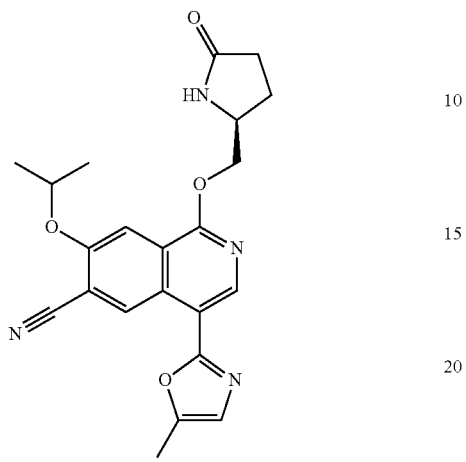

To a mixture of 6-cyano-N-(2-oxopropyl)-1-{[(2S)-5-oxopyrrolidin-2-yl]methoxy}-7-(propan-2-yloxy)isoquinoline-4-carboxamide (130 mg, 0.31 mmol) in 1,2-dichloroethane (20 mL) at 0° C. was added TFAA (1 mL) and DIEA (1 mL). The reaction mixture was stirred at 0° C. for 2 h. The reaction mixture was warmed to 20° C. and stirred for 18 h. TFAA (1 mL) and DIEA (3 mL) were added and the mixture was stirred at 20° C. for 3 h. The mixture was diluted with DCM (30 mL), washed with saturated NaHCO$_3$ (20 mL) and brine (20 mL), dried (Na$_2$SO$_4$), filtered and concentrated. The residue was purified by flash chromatography over silica gel (MeOH/DCM from 0/100 to 4/96) to give the title compound as a yellow solid (60 mg, 48% yield). $^1$H NMR (400 MHz, CDCl$_3$) δ 9.67 (s, 1H), 8.56 (s, 1H), 7.58 (s, 1H), 6.97 (s, 1H), 6.40 (br s, 1H), 4.86 (td, 1H), 4.70 (dd, 1H), 4.46 (dd, 1H), 4.25 (br s, 1H), 2.05 (d, 1H), 1.62 (s, 3H), 1.43-1.54 (m, 6H). Some peaks were obscured by solvent. MS m/z 429 [M+Na]$^+$.

Step 3: Preparation of 4-(5-Methyl-1,3-oxazol-2-yl)-1-{[(2S)-5-oxopyrrolidin-2-yl]methoxy}-7-(propan-2-yloxy)isoquinoline-6-carboxamide A mixture of 4-(5-methyl-1,3-oxazol-2-yl)-1-{[(2S)-5-oxopyrrolidin-2-yl]methoxy}-7-(propan-2-yloxy)isoquinoline-6-carbonitrile (60 mg, 0.15 mmol) and K$_2$CO$_3$ (102 mg, 0.74 mmol) in DMSO (4 mL) was stirred at 25° C. for 5 min. H$_2$O$_2$ (117 mg, 1.03 mmol) was added and the reaction mixture was stirred at 25° C. for 2 h. The mixture was quenched with dimethyl sulfide (91.7 mg, 1.48 mmol) and stirred at 25° C. for 30 min. The mixture was filtered and washed with DCM and EtOAc. The filtrate was concentrated and the residue was purified by preparative HPLC (Column: DIKMA Diamonsil(2) C18 200*20 mm*5 um Mobile phase: from 20% MeCN in water (0.225% FA) to 40% MeCN in water (0.225% FA) Flow rate: 30 mL/min Wavelength: 220 nm) to give the title compound as a yellow solid (13 mg, 21% yield). $^1$H NMR (400 MHz, DMSO-d6) δ 9.44 (s, 1H), 8.50 (s, 1H), 8.15 (s, 1H), 7.77 (br s, 1H), 7.73 (s, 1H), 7.13 (s, 1H), 4.86-5.04 (m, 1H), 4.50-4.62 (m, 1H), 4.33-4.45 (m, 1H), 4.06 (br s, 1H), 2.43 (s, 3H), 2.19-2.36 (m, 3H), 1.94 (br s, 1H), 1.40 (dd, 6H). The NH proton obscured. MS m/z 425 [M+H]$^+$.

Example 10

1-{[(2S,3R)-3-ethyl-5-oxopyrrolidin-2-yl]methoxy}-4-[(phenylsulfonyl)amino]-7-(propan-2-yloxy)isoquinoline-6-carboxamide

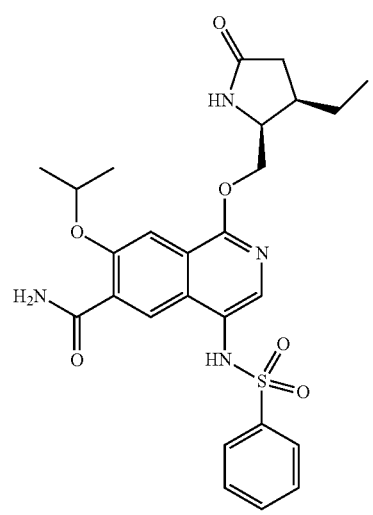 [SMILES: CC[C@@H]1CC(=O)N[C@@H]1COc1ncc(NS(=O)(=O)c2ccccc2)c2cc(C(N)=O)c(OC(C)C)cc12]

Step 1: Preparation of 4-Nitro-1-oxo-7-(propan-2-yloxy)-1,2-dihydroisoquinoline-6-carbonitrile

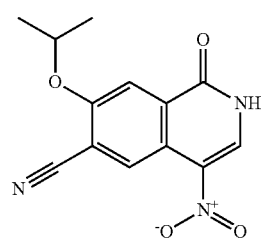

To a mixture of 1-oxo-7-(propan-2-yloxy)-1,2-dihydroisoquinoline-6-carbonitrile (8.3 g, 36.4 mmol) in AcOH (160 mL) and EtOAc (30 mL) at 0° C. was added HNO$_3$ (9.17 g, 145 mmol). The reaction mixture was allowed to warm to room temperature and was then heated at 50° C. for 12 h. The reaction mixture was poured in to ice water. The mixture was filtered to give the title compound as a yellow solid (5.1 g, 51% yield). $^1$H NMR (400 MHz, DMSO-d6) δ 11.52 (br s, 1H), 8.22 (s, 1H), 7.77 (s, 1H), 7.16 (t, 1H), 6.56 (d, 1H), 4.82-5.01 (m, 1H), 1.37 (d, 6H). MS m/z 274 [M+H]$^+$.

Step 2: Preparation of 1-Chloro-4-nitro-7-(propan-2-yloxy)isoquinoline-6-carbonitrile

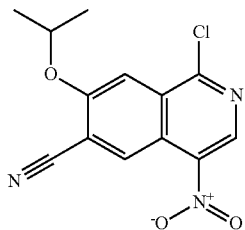

To a stirred solution of 4-nitro-1-oxo-7-(propan-2-yloxy)-1,2-dihydroisoquinoline-6-carbonitrile (6.2 g, 22.7 mmol) in POCl$_3$ (50 mL) was added TEA (2.3 mg, 22.7 mmol) and the reaction mixture was heated to reflux for 2 h. The mixture was cooled to room temperature and excess of POCl$_3$ was evaporated under reduced pressure. The residue was quenched with aq. NaHCO$_3$. The aqueous phase was extracted with DCM. The combined organic phase was washed with saturated sodium bicarbonate solution, water, followed by brine, dried over Na$_2$SO$_4$ and concentrated. The residue was purified by flash chromatography over silica gel (petroleum ether/DCM from 0/100 to 43/57) to give the title compound as a yellow solid (4.8 g, 73% yield). $^1$H NMR (400 MHz, DMSO-d6) δ 12.64 (br s, 1H), 8.84 (s, 1H), 8.60 (s, 1H), 7.85 (s, 1H), 4.97 (td, 1H), 1.38 (d, 6H). MS m/z 292 [M+H]$^+$.

Step 3: Preparation of 1-{[(2S,3R)-3-Ethyl-5-oxopyrrolidin-2-yl]methoxy}-4-nitro-7-(propan-2-yloxy)isoquinoline-6-carbonitrile

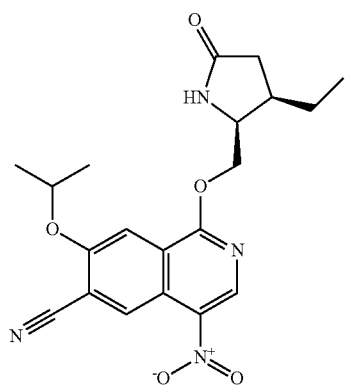

To a solution of 1-chloro-4-nitro-7-(propan-2-yloxy)isoquinoline-6-carbonitrile (3 g, 10.3 mmol) and Cs$_2$CO$_3$ (6.7 g, 20.6 mmol) in 1,4-dioxane (10 mL) was added (4R,5S)-4-ethyl-5-(hydroxymethyl)pyrrolidin-2-one (1.77 g, 12.3 mmol). The mixture was stirred at 20° C. for 16 h. The reaction mixture was filtered through a pad of Celite and the filtrate was evaporated in vacuo. The residue was purified by silica gel chromatography (0% to 30% MeOH in DCM) to give the title compound as a yellow solid (2.4 g, 59% yield). $^1$H NMR (400 MHz, CDCl$_3$) δ 9.12 (s, 1H), 8.91 (s, 1H), 7.61 (s, 1H), 6.51 (s, 1H), 4.91 (td, 1H), 4.56-4.78 (m, 2H), 4.01-4.21 (m, 1H), 2.60-2.78 (m, 1H), 2.51 (dd, 1H), 2.17 (dd, 1H), 1.62-1.75 (m, 2H), 1.50 (dd, 6H), 1.03 (t, 3H).

Step 4: Preparation of 4-Amino-1-{[(2S,3R)-3-ethyl-5-oxopyrrolidin-2-yl]methoxy}-7-(propan-2-yloxy)isoquinoline-6-carbonitrile

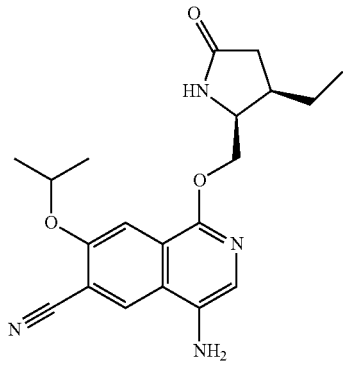 [SMILES: CC[C@@H]1CC(=O)N[C@@H]1COc1ncc(N)c2cc(C#N)c(OC(C)C)cc12]

To a solution of 1-{[(2S,3R)-3-ethyl-5-oxopyrrolidin-2-yl]methoxy}-4-nitro-7-(propan-2-yloxy)isoquinoline-6-carbonitrile (4.1 g, 10.3 mmol) in THF (51 mL), H$_2$O (51 mL) and EtOH (25 mL) was added Zn (6.73 g, 103 mmol) and NH$_4$Cl (5.5 g, 103 mmol). The resulting mixture was stirred at 25° C. for 16 h. The reaction mixture was filtered through a pad of Celite and the filtrate was evaporated in vacuo. The residue was purified by silica gel chromatography (0% to 12% MeOH in EtOAc) to give the title compound as a yellow solid (3.4 g, 90% yield). $^1$H NMR (400 MHz, CDCl$_3$) δ 8.03 (s, 1H), 7.38 (s, 1H), 7.30 (s, 1H), 6.93 (s, 1H), 4.71 (td, 1H), 4.35-4.51 (m, 2H), 4.01-4.08 (m, 1H), 2.56-2.69 (m, 1H), 2.42-2.52 (m, 1H), 2.20 (dd, 1H), 2.05 (s, 1H), 1.44 (dd, 6H), 0.98 (t, 3H). MS m/z 369 [M+H]$^+$.

Step 5: Preparation of 4-Amino-1-{[(2S,3R)-3-ethyl-5-oxopyrrolidin-2-yl]methoxy}-7-(propan-2-yloxy)isoquinoline-6-carboxamide

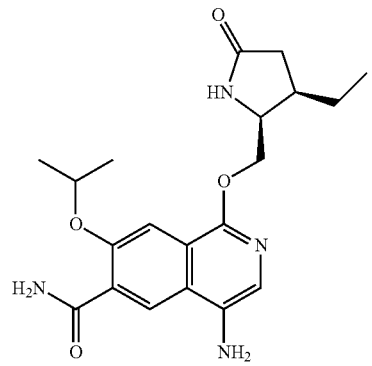 [SMILES: CC[C@@H]1CC(=O)N[C@@H]1COc1ncc(N)c2cc(C(N)=O)c(OC(C)C)cc12]

To a solution of 4-amino-1-{[(2S,3R)-3-ethyl-5-oxopyrrolidin-2-yl]methoxy}-7-(propan-2-yloxy)isoquinoline-6-carbonitrile (1.4 g, 3.8 mmol) and K$_2$CO$_3$ (2.63 g, 19 mmol) in DMSO (5 mL) was added H$_2$O$_2$ (1.29 g, 38 mmol). The resulting orange mixture was stirred at 25° C. for 16 h. H$_2$O$_2$ (517 mg, 15.2 mmol) was added, and the resulting mixture was stirred at 25° C. for 10 h. The reaction mixture was poured into water, and the resulting solids were collected by filtration and washed with water. The solid was dried to give the title compound as a yellow solid (1.1 g, 75% yield). $^1$H NMR (400 MHz, DMSO-d6) δ 8.37 (s, 1H), 7.90 (s, 1H), 7.69 (br s, 2H), 7.45 (s, 1H), 7.25 (s, 1H), 5.23 (s, 2H), 4.83 (td, 1H), 4.17-4.36 (m, 2H), 3.83-3.93 (m, 1H), 3.32 (s, 1H), 2.20-2.31 (m, 1H), 2.06-2.17 (m, 1H), 1.58 (td, 1H), 1.39 (t, 6H), 0.90 (t, 3H). MS m/z 387 [M+H]⁺.

Step 6: Preparation of 1-{[(2S,3R)-3-ethyl-5-oxopyrrolidin-2-yl]methoxy}-4-[(phenylsulfonyl)amino]-7-(propan-2-yloxy)isoquinoline-6-carboxamide To a solution of 4-amino-1-{[(2S,3R)-3-ethyl-5-oxopyrrolidin-2-yl]methoxy}-7-(propan-2-yloxy)isoquinoline-6-carboxamide (100 mg, 0.26 mmol) in pyridine (2 mL) was added benzenesulfonyl chloride (55 mg, 0.31 mmol). The mixture was stirred at 25° C. for 5 h. Water (5 mL) was added, and the mixture was extracted with DCM. The combined organic phase was dried over Na₂SO₄. The residue was purified by preparative HPLC (Column: Ultimate XB-C18 3 um, 3.0*50 mm, Gradient Time: 11 min, Mobile phase: from 1% MeCN in water (0.05% TFA) to 100% MeCN in water (0.05% TFA), Flow rate: 35 mL/min, Wavelength: 220 nm) to give the title compound as a white solid (78 mg, 57% yield). ¹H NMR (400 MHz, CDCl₃) δ 9.30 (br s, 1H), 8.95 (br s, 1H), 8.17 (br s, 1H), 8.00 (s, 1H), 7.69 (d, 3H), 7.28-7.35 (m, 1H), 7.28-7.39 (m, 2H), 7.18-7.24 (m, 2H), 7.09 (br s, 1H), 4.65-4.78 (m, 1H), 4.56 (d, 1H), 4.33 (d, 1H), 4.05 (d, 1H), 2.60 (d, 1H), 2.46 (dd, 1H), 2.19 (dd, 1H), 1.57 (d, 3H), 1.44 (d, 3H), 1.38 (d, 1H), 0.96 (t, 3H). MS m/z 527 [M+H]⁺.

Example 11

1-{[(2S,3R)-3-Ethyl-5-oxopyrrolidin-2-yl]methoxy}-7-(propan-2-yloxy)-4-[(pyridin-3-ylsulfonyl)amino]isoquinoline-6-carboxamide

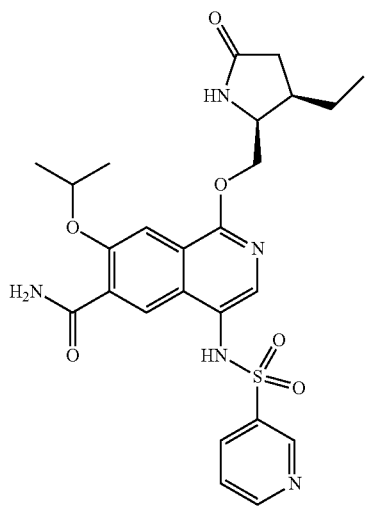 [SMILES: CC[C@@H]1CC(=O)N[C@@H]1COc1ncc(NS(=O)(=O)c2cccnc2)c2cc(C(N)=O)c(OC(C)C)cc12]

To a solution of 4-amino-1-{[(2S,3R)-3-ethyl-5-oxopyrrolidin-2-yl]methoxy}-7-(propan-2-yloxy)isoquinoline-6-carboxamide (80 mg, 0.21 mmol) in pyridine (2 mL) was added pyridine-3-sulfonyl chloride (53 mg, 0.25 mmol). The mixture was stirred at 25° C. for 5 h. Water (5 mL) was added and the mixture was extracted with DCM. The combined organic solvent was dried over Na₂SO₄. The residue was purified by preparative HPLC (Column: Agela durashell C18*21.2 mm*5 μm, Gradient Time: 11 min, Mobile phase: from 30% MeOH in water (0.225% FA) to 50% MeOH in water (0.225% FA), Flow rate: 35 mL/min, Wavelength: 220 nm) to give the title compound as a white solid (67 mg, 61% yield). ¹H NMR (400 MHz, CDCl₃) δ 8.83 (br s, 1H), 8.64 (br s, 1H), 8.51 (d, 1H), 8.26 (br s, 1H), 7.93-8.13 (m, 3H), 7.19 (br s, 1H), 7.06 (br s, 1H), 4.71 (br s, 1H), 4.59 1H), 4.33 (br s, 1H), 4.06 (d, 1H), 2.62 (br s, 1H), 2.47 (dd, 1H), 2.19 (dd, 1H), 1.61 (d, 3H), 1.56 (br s, 2H), 1.45 (d, 3H), 1.40 (br s, 1H), 0.97 (t, 3H). MS m/z 528 [M+H]⁺.

Example 12

1-{[(2S,3R)-3-Ethyl-5-oxopyrrolidin-2-yl]methoxy}-4-[(1H-imidazol-4-ylsulfonyl)amino]-7-(propan-2-yloxy)isoquinoline-6-carboxamide

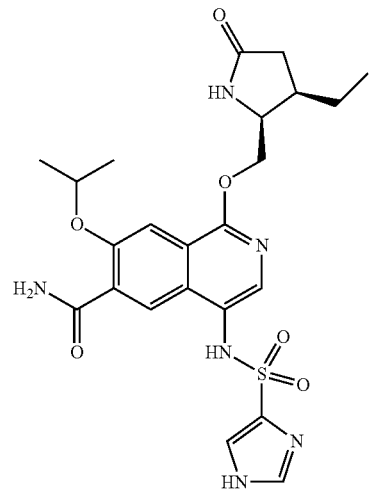 [SMILES: CC[C@@H]1CC(=O)N[C@@H]1COc1ncc(NS(=O)(=O)c2c[nH]cn2)c2cc(C(N)=O)c(OC(C)C)cc12]

To a solution of 4-amino-1-{[(2S,3R)-3-ethyl-5-oxopyrrolidin-2-yl]methoxy}-7-(propan-2-yloxy)isoquinoline-6-carboxamide (80 mg, 0.21 mmol) in pyridine (2 mL) was added 1H-imidazole-4-sulfonyl chloride (138 mg, 0.828 mmol). The mixture was stirred at 25° C. for 5 h. Water (5 mL) was added, the mixture was extracted with DCM. The combined organic phase was dried over Na₂SO₄. The residue was purified by preparative HPLC (Column: Agela durashell C18*21.2 mm*5 μm, Gradient Time: 11 min, Mobile phase: from 20% MeOH in water (0.225% FA) to 40% MeOH in water (0.225% FA), Flow rate: 35 mL/min, Wavelength: 220 nm) to give the title compound as a white solid (46 mg, 43% yield). ¹H NMR (400 MHz, DMSO-d6) δ 9.92 (br s, 1H), 8.35 (s, 1H), 7.96 (s, 1H), 7.84 (s, 1H), 7.73 (br s, 1H), 7.66 (br s, 1H), 7.52 (s, 1H), 7.47 (s, 2H), 4.79-4.88 (m, 1H), 4.38 (d, 2H), 3.90 (br s, 1H), 2.21-2.35 (m, 2H), 2.04-2.15 (m, 1H), 1.51-1.63 (m, 1H), 1.38 (dd, 6H), 0.90 (t, 3H). Peak obscured by solvent. MS m/z 539 [M+Na]⁺.

Example 13

1-{[(2S,3R)-3-Ethyl-5-oxopyrrolidin-2-yl]methoxy}-4-{[(1-methyl-1H-imidazol-4-yl)sulfonyl]amino}-7-(propan-2-yloxy)isoquinoline-6-carboxamide

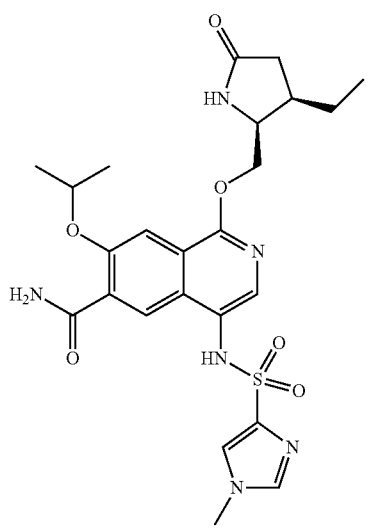 [SMILES: CC[C@@H]1CC(=O)N[C@@H]1COc1ncc(NS(=O)(=O)c2cn(C)cn2)c2cc(C(N)=O)c(OC(C)C)cc12]

To a solution of 4-amino-1-{[(2S,3R)-3-ethyl-5-oxopyrrolidin-2-yl]methoxy}-7-(propan-2-yloxy)isoquinoline-6-carboxamide (80 mg, 0.21 mmol) in pyridine (2 mL) was added 1-methyl-1H-imidazole-4-sulfonyl chloride (45 mg, 0.25 mmol). The mixture was stirred at 25° C. for 5 h. Water (5 mL) was added, and the mixture was extracted with DCM. The combined organic phase was dried over $Na_2SO_4$. The residue was purified by preparative HPLC (Column: Agela durashell C18*21.2 mm*5 μm, Gradient Time: 11 min, Mobile phase: from 25% MeOH in water (0.225% FA) to 45% MeOH in water (0.225% FA), Flow rate: 35 mL/min, Wavelength: 220 nm) to give the title compound as a white solid (81 mg, 74% yield). $^1$H NMR (400 MHz, CDCl$_3$) δ 9.27 (br s, 1H), 8.78 (s, 1H), 7.99 (br s, 1H), 7.89 (s, 1H), 7.46 (br s, 1H), 7.34 (br s, 1H), 7.25 (br s, 1H), 7.20 (br s, 1H), 7.12 (br s, 1H), 4.76 (br s, 1H), 4.52-4.62 (m, 1H), 4.41 (d, 1H), 4.08 (br s, 1H), 3.57 (s, 3H), 2.61 (br s, 1H), 2.47 (dd, 1H), 2.20 (dd, 1H), 1.59 (d, 2H), 1.51 (d, 3H), 1.44 (d, 3H), 0.98 (t, 3H). MS m/z 531 [M+H]$^+$.

Example 14

4-{[(1,2-Dimethyl-1H-imidazol-4-yl)sulfonyl]amino}-1-{[(2S,3R)-3-ethyl-5-oxopyrrolidin-2-yl]methoxy}-7-(propan-2-yloxy)isoquinoline-6-carboxamide

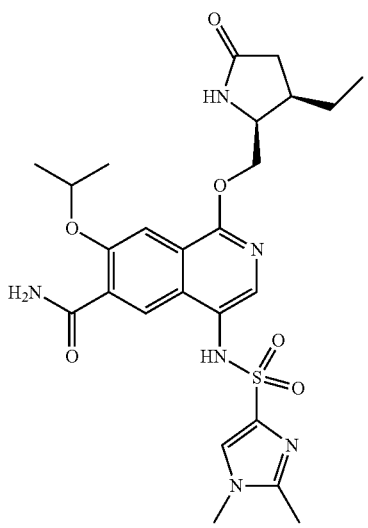 [SMILES: CC[C@@H]1CC(=O)N[C@@H]1COc1ncc(NS(=O)(=O)c2cn(C)c(C)n2)c2cc(C(N)=O)c(OC(C)C)cc12]

To a solution of 4-amino-1-{[(2S,3R)-3-ethyl-5-oxopyrrolidin-2-yl]methoxy}-7-(propan-2-yloxy)isoquinoline-6-carboxamide (80 mg, 0.21 mmol) in pyridine (2 mL) was added 1,2-dimethyl-1H-imidazole-4-sulfonyl chloride (60 mg, 0.31 mmol). The mixture was stirred at 25° C. for 5 h. Water (5 mL) was added, and the mixture was extracted with DCM. The combined organic phase was dried over $Na_2SO_4$. The residue was purified by preparative HPLC (Column: Agela durashell C18*21.2 mm*5 μm, Gradient Time: 11 min, Mobile phase: from 20% MeOH in water (0.225% FA) to 40% MeOH in water (0.225% FA), Flow rate: 35 mL/min, Wavelength: 220 nm) to give the title compound as a white solid (57 mg, 51% yield). $^1$H NMR (400 MHz, DMSO-d6) δ 8.18 (s, 1H), 8.14 (s, 1H), 7.97 (s, 1H), 7.71 (br s, 1H), 7.62 (br s, 1H), 7.60 (s, 1H), 7.46 (s, 1H), 7.41 (s, 1H), 4.83 (td, 1H), 4.39 (d, 2H), 3.89-3.95 (m, 1H), 3.48 (s, 3H), 2.23-2.34 (m, 5H), 2.03-2.16 (m, 2H), 1.51-1.63 (m, 1H), 1.37 (dd, 6H), 0.91 (t, 3H). MS m/z 545 [M+H]$^+$.

Example 15

4-Amino-1-{[(2S,3S,4S)-3-ethyl-4-fluoro-5-oxopyrrolidin-2-yl]methoxy}-7-methoxyisoquinoline-6-carboxamide

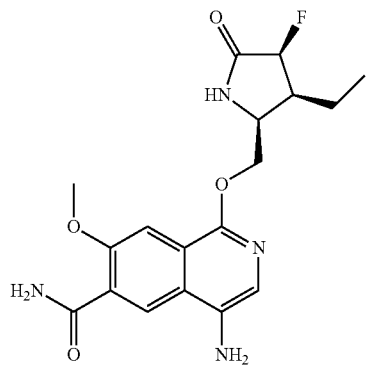 [SMILES: CC[C@@H]1[C@H](F)C(=O)N[C@@H]1COc1ncc(N)c2cc(C(N)=O)c(OC)cc12]

Step 1: Preparation of 1-{[(2S,3S,4S)-3-Ethyl-4-fluoro-5-oxopyrrolidin-2-yl]methoxy}-7-methoxy-4-nitroisoquinoline-6-carbonitrile

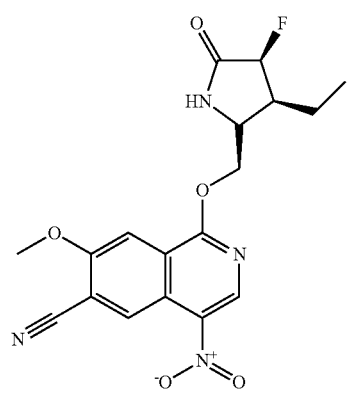

To a vial was added 1-chloro-7-methoxy-4-nitroisoquinoline-6-carbonitrile (0.2 g, 0.76 mmol), (3S,4S,5S)-4-ethyl-3-fluoro-5-(hydroxymethyl)pyrrolidin-2-one (0.12 g, 0.76 mmol), cesium carbonate (1.24 g, 3.8 mmol) and 1,4-dioxane (7.6 mL). The mixture was stirred vigorously overnight. The mixture was filtered through a plug of silica gel and rinsed with EtOAc. The filtrates were purified via silica gel chromatography using 0-20% MeOH/DCM. The residue was further purified on silica gel using 0-100% EtOAc in heptane to give the title compound as a solid (135 mg, 46% yield). $^1$H NMR (400 MHz, CDCl$_3$) δ 9.03-9.20 (m, 1H), 8.92 (s, 1H), 7.84 (s, 1H), 7.41 (br s, 1H), 4.80-5.01 (m, 2H), 4.51 (dd, 1H), 4.16-4.29 (m, 1H), 4.04-4.14 (m, 3H), 2.51-2.75 (m, 1H), 1.74-1.92 (m, 1H), 1.58-1.72 (m, 1H), 1.15 (t, 3H). MS m/z 389 [M+H]$^+$.

Step 2: Preparation of 1-{[(2S,3S,4S)-3-Ethyl-4-fluoro-5-oxopyrrolidin-2-yl]methoxy}-7-methoxy-4-nitroisoquinoline-6-carboxamide

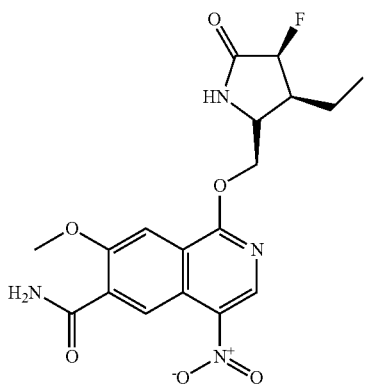

To a round bottom flask was added 1-{[(2S,3S,4S)-3-ethyl-4-fluoro-5-oxopyrrolidin-2-yl]methoxy}-7-methoxy-4-nitroisoquinoline-6-carbonitrile (90 mg, 0.23 mmol) and methanesulfonic acid (1.75 mL, 26.8 mmol). The mixture was heated to 70° C. for 18 h. The mixture was quenched in ice. To this mixture was added EtOAc and the mixture made basic to pH 10 with the addition of ammonium hydroxide. The layers were separated and the aqueous phase extracted five times with EtOAc. The combined EtOAc extracts were dried over anhydrous Na$_2$SO$_4$. The residue was purified via silica gel chromatography using 0-20% methanol in DCM to give the title compound as a solid (63 mg, 67% yield). $^1$H NMR (400 MHz, CDCl$_3$) δ 9.10 (s, 1H), 8.79 (s, 1H), 7.82 (br s, 1H), 7.63 (s, 1H), 7.56 (br s, 1H), 6.62 (br s, 1H), 5.01 (d, 1H), 4.84-4.95 (m, 1H), 4.58 (d, 1H), 4.30 (br s, 1H), 4.03 (s, 2H), 2.56-2.75 (m, 1H), 2.18 (s, 1H), 1.99-2.10 (m, 1H), 1.64-1.90 (m, 1H), 1.16 (t, 3H). MS m/z 407 [M+H]$^+$.

Step 3: Preparation of 4-Amino-1-{[(2S,3S,4S)-3-ethyl-4-fluoro-5-oxopyrrolidin-2-yl]methoxy}-7-methoxyisoquinoline-6-carboxamide To a mixture of zinc (91 mg, 1.39 mmol), ammonium chloride (75 mg, 1.39 mmol) and 1-{[(2S,3S,4S)-3-ethyl-4-fluoro-5-oxopyrrolidin-2-yl]methoxy}-7-methoxy-4-nitroisoquinoline-6-carboxamide (57 mg, 0.14 mmol) was added water (0.7 mL), tetrahydrofuran (0.7 mL) and ethanol (0.35 mL). The mixture was stirred at ambient temperature for 20 min. The mixture was filtered through Celite and the filtrates were purified via silica gel chromatography using 0-20% methanol in DCM to give the title compound as a solid (37 mg, 71% yield). $^1$H NMR (400 MHz, METHANOL-d4) δ 8.54 (s, 1H), 7.81 (s, 1H), 7.40 (s, 1H), 4.96 (dd, 1H), 4.51 (dd, 1H), 4.32 (dd, 1H), 4.17 (sext, 1H). 4.06 (s, 3H), 2.78-2.61 (m, 1H), 1.84-1.65 (m, 2H), 1.11 (t, 3H). MS m/z 377 [M+H]$^+$.

Example 16

1-(((4R,7S)-7-fluoro-6-oxo-5-azaspiro[2.4]heptan-4-yl)methoxy)-7-isopropoxyisoquinoline-6-carboxamide

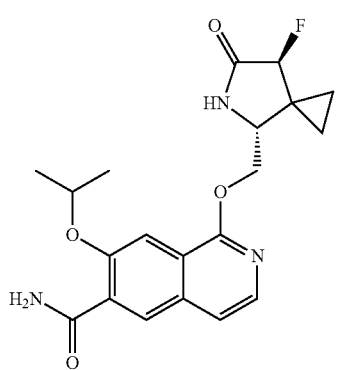 [SMILES: CC(C)Oc1cc2c(OC[C@@H]3NC(=O)[C@@H](F)C34CC4)nccc2cc1C(N)=O]

Step 1: Preparation of ethyl 2-cyclopropylideneacetate

A suspension of (1-ethoxycyclopropoxy)trimethylsilane (68 g, 390 mmol), ethyl 2-(triphenylphosphanylidene)acetate (178 g, 507 mmol) and benzoic acid (6.19 g, 50.7 mmol) in toluene (1020 mL) was stirred at 90° C. overnight. After cooling, the reaction mixture was concentrated to remove toluene. To the residue was added ether (500 mL) and petroleum ether (250 mL) and the mixture was stirred at room temperature for 2 h. The resulting mixture was filtered and the filtrate was concentrated to give the crude product, which was purified by flash column (petroleum ether/EtOAc=10/1) to give ethyl 2-cyclopropylideneacetate as yellow oil (50 g, which was used without further purification). $^1$H NMR (400 MHz, CDCl$_3$) δ=6.40 (s, 1H), 4.38 (m, 2H), 1.40-0.69 (m, 7H).

Step 2: Preparation of ethyl 2-(1-(nitromethyl)cyclopropyl)acetate

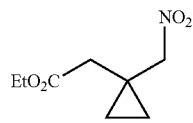

A mixture of ethyl 2-cyclopropylideneacetate (40 g, 317 mmol), nitromethane (96.8 g, 1590 mmol) and DBU (483 g, 317 mmol) in CH$_3$CN (160 mL) was stirred at 60° C. overnight under N$_2$ atmosphere. The reaction mixture was poured into 1N HCl (400 mL) and extracted with EtOAc (600 mL×2). The combined layers were washed with water and brine, then dried over anhydrous Na$_2$SO$_4$. The crude product was purified by flash column (petroleum ether/EtOAc=10/1) to give ethyl 2-(1-(nitromethyl)cyclopropyl)acetate (32.5 g, 55% yield) as colorless oil. $^1$H NMR (400 MHz, CDCl$_3$) δ=4.43 (s, 2H), 4.17 (m, 2H), 2.50 (s, 2H), 1.28 (m, 3H), 0.88-0.69 (m, 4H).

Step 3: Preparation of ethyl 2-(1-(2-hydroxy-1-nitroethyl)cyclopropyl)acetate

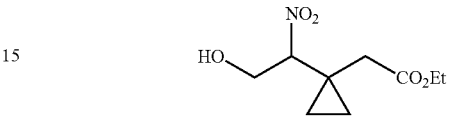

A solution of compound ethyl 2-(1-(nitromethyl)cyclopropyl)acetate (15 g, 80 mmol) in iPrOH (15 mL) was stirred with paraformaldehyde (4.65 g, 160 mmol) and KF (466 mg, 8.01 mmol) at 22° C. for 7 h. The resulting mixture was treated with EtOAc (500 mL×3) and H$_2$O (200 mL). The combined organic layers were washed with brine, dried and concentrated to give the crude product, which was purified by column chromatography (petroleum ether/ethyl acetate=3/1) to give ethyl 2-(1-(2-hydroxy-1-nitroethyl)cyclopropyl)acetate (9 g, 52% yield) as a colorless oil. Starting material (4 g, 27% yield) was recovered as yellow oil. $^1$H NMR (400 MHz, CDCl$_3$) δ 4.16-3.95 (m, 3H), 3.93-3.85 (m, 1H), 3.16 (br s, OH), 2.81 (d, 1H), 2.33 (m, 1H), 2.18 (d, 1H), 1.25-1.16 (m, 3H), 0.97-0.83 (m, 2H), 0.81-0.69 (m, 1H), 0.67-0.53 (m, 1H).

Step 4: Preparation of 4-(hydroxymethyl)-5-azaspiro[2.4]heptan-6-one

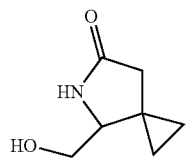

A mixture of ethyl 2-(1-(2-hydroxy-1-nitroethyl)cyclopropyl)acetate (5.50 g, 25.3 mmol) and Raney Ni (2.0 g) in EtOH (100 mL) was stirred at 30-40° C. for 6 h under H$_2$ atmosphere. The resulting mixture was filtered and the filtrate was stirred at 80° C. for 36 h. The reaction mixture was concentrated to give the crude product, which was purified by flash column to give 4-(hydroxymethyl)-5-azaspiro[2.4]heptan-6-one (1.9 g, 53% yield) as an off white solid. $^1$H NMR (400 MHz, DMSO-d6) δ 7.72 (br. s., 1H), 4.67 (t, 1H), 3.31 (m, 2H), 3.13-3.00 (m, 1H), 2.39 (d, 1H), 1.88 (d, 1H), 0.86-0.73 (m, 1H), 0.61-0.41 (m, 3H). MS m/z 142.1 [M+H]$^+$.

Step 5: Preparation of 3',3'-dimethyldihydro-3'H-spiro[cyclopropane-1,7'-pyrrolo[1,2-c]oxazol]-5'(6'H)-one

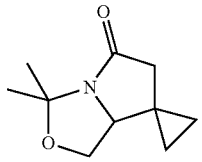

To a stirred solution of 4-(hydroxymethyl)-5-azaspiro[2.4]heptan-6-one (4.50 g, 31.9 mmol) in toluene (100 mL) was added TsOH.H$_2$O (60.6 mg, 0.319 mmol) followed by 2,2-dimethoxypropane (13.3 g, 128 mmol). The reaction mixture was heated to reflux for 2 h. The reaction mixture was cooled to room temperature and evaporated to dryness. The residue was dissolved in MTBE (500 mL), washed with 1N aq NaOH (50 mL) and water (50 mL) then dried over Na$_2$SO$_4$ to give 3',3'-dimethyldihydro-3'H-spiro[cyclopropane-1,7'-pyrrolo[1,2-c]oxazol]-5'(6'H)-one (5.4 g, 93% yield) as colorless oil, which was used in the next step without further purification.

Step 6: Preparation of 6'-fluoro-3',3'-dimethyldihydro-3'H-spiro[cyclopropane-1,7'-pyrrolo[1,2-c]oxazol]-5'(6'H)-one

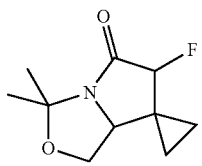

A solution of 3',3'-dimethyldihydro-3'H-spiro[cyclopropane-1,7'-pyrrolo[1,2-c]oxazol]-5'(6'H)-one (5.4 g, 29.8 mmol) in dry THF (130 mL) was briefly placed under a vacuum then purged with nitrogen. The mixture was chilled in a dry ice-acetone bath for 15 min at which time LiHMDS (27 mL, 67.5 mmol) was slowly added via syringe. The resulting mixture was stirred chilled for 45 min at which time the mixture was added via cannula to a mixture of N-fluorodibenzenesulphonimide (NFSI) (12.2 g, 38.7 mmol) in dry THF (130 mL) pre-cooled to −78° C. The mixture was stirred at −78° C. for 15 min. The cooling bath was removed, and the reaction mixture was slowly quenched with water (100 mL). EtOAc (200 mL) was added. The organic phase was stirred with 5% aq NaI (13.4 g NaI in 250 mL H$_2$O) for 15 min. The organic phase was washed with 0.1M sodium thiosulfate (100 mL), 1N NaOH (100 mL), and finally brine. The organic phase was dried over anhydrous Na$_2$SO$_4$ and the residue was purified via flash chromatography using 40% EtOAc: heptanes to give 6'-fluoro-3',3'-dimethyldihydro-3'H-spiro[cyclopropane-1,7'-pyrrolo[1,2-c]oxazol]-5'(6'H)-one (3 g, 50% yield), a white solid, as a mixture of diastereomers. $^1$H NMR (400 MHz, CDCl$_3$) δ 5.19-5.00 (m, 0.5H), 4.58-4.41 (m, 0.5H), 4.38 (m, 0.5H), 4.04 (m, 0.5H), 3.86 (m, 1H), 3.50-3.36 (m, 1H), 1.73 (m, 3H), 1.52 (m, 3H), 1.29-1.10 (m, 1H), 0.99-0.58 (m, 3H). MS m/z 200.1 [M+H]$^+$

Step 7: Preparation of 7-fluoro-4-(hydroxymethyl)-5-azaspiro[2.4]heptan-6-one

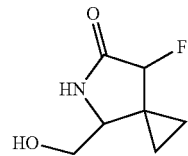 [SMILES: O=C1NC(CO)C2(CC2)C1F]

To a stirred solution of 6'-fluoro-3',3'-dimethyldihydro-3'H-spiro[cyclopropane-1,7'-pyrrolo[1,2-c]oxazol]-5'(6'H)-one (1 g, 5.02 mmol) in acetonitrile-water (10 mL: 0.5 mL) was added TFA (57.2 mg, 0.50 mmol) and mixture was heated to 90° C. for 1 h. The mixture was concentrated to dryness and azeotroped three times with MeCN (3×10 mL), once with MeCN-water (10 mL+0.5 mL) and with toluene (10 mL×3) to give 7-fluoro-4-(hydroxymethyl)-5-azaspiro[2.4]heptan-6-one (0.8 g, ~100%) was obtained as a white solid as a ~1:1 mixture of diastereomers which was used without further purification. $^1$H NMR (400 MHz, DMSO-d6) δ=8.61 (br. s., 0.5H), 8.34 (br. s., 0.5), 4.98-4.69 (m, 0.5H), 4.57-4.33 (m, 0.5H), 3.55-3.17 (m, 4H), 1.07-0.55 (m, 4H).

Step 8: Preparation of 1-((7-fluoro-6-oxo-5-azaspiro[2.4]heptan-4-yl)methoxy)-7-isopropoxyisoquinoline-6-carbonitrile

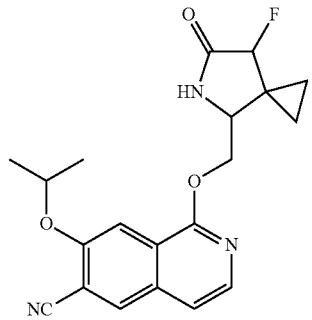 [SMILES: CC(C)Oc1cc2c(OCC3NC(=O)C(F)C34CC4)nccc2cc1C#N]

To the stirred solution of 1-chloro-7-isopropoxyisoquinoline-6-carbonitrile (600 mg, 2.43 mmol) and 7-fluoro-4-(hydroxymethyl)-5-azaspiro[2.4]heptan-6-one (426 mg, 2.68 mmol) in DMF (20 mL) was added dropwise KHMDS (6.1 mL, 6.1 mmol, 1M in THF) under N$_2$ atmosphere at 0° C. The mixture was stirred at 0° C. for 1 h. The mixture was treated with saturated aqueous NH$_4$Cl solution and extracted with EtOAc (100 mL×3), washed with water followed by brine (50 mL), dried over Na$_2$SO$_4$, filtered and concentrated under reduced pressure.

The residue was purified by flash chromatography on silica gel (50% EtOAc-hexane) to give a first eluting isomer as racemic 1-(((anti)-7-fluoro-6-oxo-5-azaspiro[2.4]heptan-4-yl)methoxy)-7-isopropoxyisoquinoline-6-carbonitrile (300 mg, 33% yield) as a yellow solid. $^1$H NMR (400 MHz, DMSO-d6) δ 8.92 (s, 1H), 8.52 (s, 1H), 7.97 (d, 1H), 7.61 (s, 1H), 7.42 (d, 1H), 5.14-4.96 (d, 1H), 4.96-4.87 (m, 1H), 4.45-4.31 (m, 2H), 3.83 (t, 1H), 1.40 (dd, 6H), 1.11-1.00 (m, 2H), 0.89-0.76 (m, 2H). An nOe experiment revealed a spatial interaction between the fluorine containing carbon C—H (5.14-4.96 (d, 1H)), and the isopropyl group, requiring the trans relationship between the fluorine and the CH₂O— group. MS m/z 388.0 [M+H]⁺ and MS m/z 409.9 [M+Na]⁺.

The second eluting isomer was collected as racemic 1-(((syn)-7-fluoro-6-oxo-5-azaspiro[2.4]heptan-4-yl)methoxy)-7-isopropoxyisoquinoline-6-carbonitrile (500 mg, 56% yield) as a white solid. ¹H NMR (400 MHz, DMSO-d6) δ 8.50 (s, 1H), 8.00-7.92 (m, 2H), 7.81 (s, 1H), 7.40 (d, 1H), 4.90 (td, 1H), 4.72-4.52 (m, 1H), 4.48 (dd, 1H), 4.27-4.17 (m, 1H), 3.73 (d, 1H), 1.38 (t, 6H), 1.09-0.96 (m, 4H).

Step 9: Separation of Racemic 1-(((anti)-7-fluoro-6-oxo-5-azaspiro[2.4]heptan-4-yl)methoxy)-7-isopropoxyisoquinoline-6-carboxamide

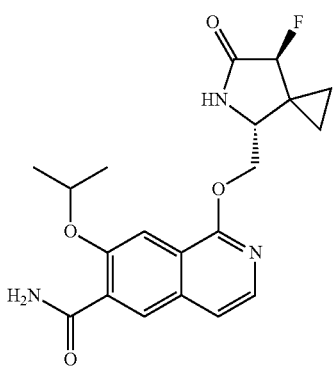 [SMILES: CC(C)Oc1cc2c(OC[C@@H]3NC(=O)[C@@H](F)C34CC4)nccc2cc1C(N)=O]

To a stirred mixture of racemic 1-(((anti)-7-fluoro-6-oxo-5-azaspiro[2.4]heptan-4-yl)methoxy)-7-isopropoxyisoquinoline-6-carbonitrile (300 mg, 0.812 mmol) in DMSO (12 mL) was added K₂CO₃ (561 mg, 4.06 mmol) at 15° C. The reaction mixture was stirred at 15° C. for 5 min. To the reaction mixture was added H₂O₂ (0.36 mL) at 15° C. The reaction mixture was stirred at 15° C. for 2 h. To the resulting mixture was added H₂O (15 mL) at 0-5° C. and and the mixture was stirred for 1 h at 15° C. The mixture was filtered and the filter cake was washed with H₂O (40 mL) and dried under vacuum to give racemic 1-(((anti)-7-fluoro-6-oxo-5-azaspiro[2.4]heptan-4-yl)methoxy)-7-isopropoxyisoquinoline-6-carboxamide (220 mg, 70% yield) as a white solid.

The enantiomers were separated by preparative chiral SFC chromatography. Instrument: SFC-200 Column: Chiralpak AS 300×50 mm I.D., 10 um. Mobile phase: Supercritical CO₂/MeOH (0.1% NH₃H₂O)=55/45 at 200 mL/min Column Temp: 38° C. Nozzle Pressure: 100 Bar. Nozzle Temp: 60° C. Evaporator Temp: 20° C. Trimmer Temp: 25° C.

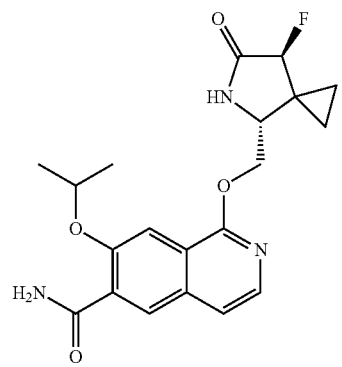 [SMILES: CC(C)Oc1cc2c(OC[C@@H]3NC(=O)[C@@H](F)C34CC4)nccc2cc1C(N)=O]

1-(((4R,7S)-7-fluoro-6-oxo-5-azaspiro[2.4]heptan-4-yl)methoxy)-7-isopropoxyisoquinoline-6-carboxamide. Analytical SFC chromatography Column: Chiralpak AS-H 150× 4.6 mm I.D., 5 μm. Mobile phase: methanol (0.05% DEA) in CO₂ from 5% to 40%. Flow rate: 3 mL/min. Wavelength: 220 nm. Analytical SFC chromatography retention time 4.265 min. ¹H NMR (400 MHz, DMSO-d6) δ 8.85 (s, 1H), 8.20 (s, 1H), 7.89 (d, 1H), 7.72 (br. s., 2H), 7.52 (s, 1H), 7.43 (d, 1H), 5.15-4.94 (m, 1H), 4.90-4.81 (m, 1H), 4.39 (d, 2H), 3.81 (br. s., 1H), 1.40 (dd, 6H), 1.06 (br. s., 2H), 0.83 (d, 2H). MS m/z 388.0 [M+H]⁺ and MS m/z 409.9 [M+Na]⁺.

Example 17

1-(((4S,7R)-7-fluoro-6-oxo-5-azaspiro[2.4]heptan-4-yl)methoxy)-7-isopropoxyisoquinoline-6-carboxamide

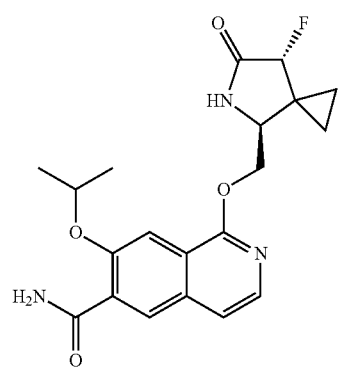 [SMILES: CC(C)Oc1cc2c(OC[C@H]3NC(=O)[C@H](F)C34CC4)nccc2cc1C(N)=O]

Analytical SFC chromatography Column: Chiralpak AS-H 150×4.6 mm I.D., 5 μm. Mobile phase: methanol (0.05% DEA) in CO₂ from 5% to 40%. Flow rate: 3 mL/min. Wavelength: 220 nm. Analytical SFC chromatography retention time 4.678 min. ¹H NMR (400 MHz, DMSO-d6) δ 8.85 (s, 1H), 8.20 (s, 1H), 7.89 (d, 1H), 7.72 (br. s., 2H), 7.52 (s, 1H), 7.43 (d, 1H), 5.15-4.94 (m, 1H), 4.90-4.81 (m, 1H), 4.39 (d, 2H), 3.81 (br. s., 1H), 1.40 (dd, 6H), 1.06 (br. s., 2H), 0.83 (d, 2H). MS m/z 388.1 [M+H]⁺ and MS m/z 410.0 [M+Na]⁺.

Example 18

Racemic 1-(((syn)-7-fluoro-6-oxo-5-azaspiro[2.4]heptan-4-yl)methoxy)-7-isopropoxyisoquinoline-6-carboxamide

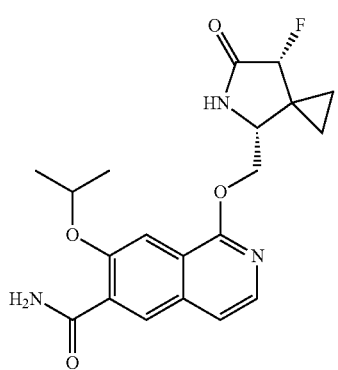 [SMILES: CC(C)Oc1cc2c(OC[C@@H]3NC(=O)[C@H](F)C34CC4)nccc2cc1C(N)=O]

To a stirred mixture of racemic 1-(((syn)-7-fluoro-6-oxo-5-azaspiro[2.4]heptan-4-yl)methoxy)-7-isopropoxyisoquinoline-6-carbonitrile (400 mg, 1.08 mmol) in DMSO (16 mL) was added $K_2CO_3$ (748 mg, 5.41 mmol) at 15° C. The reaction mixture was stirred at 15° C. for 5 min. $H_2O_2$ (0.5 mL) was added at 15° C. The reaction mixture was stirred at 15° C. for 2 h. $H_2O$ (20 mL) was added at 0-5° C. and the mixture was stirred for 1 h at 15° C. The mixture was filtered and the filter cake was washed with $H_2O$ (50 mL) and dried under vacuum to give racemic 1-(((syn)-7-fluoro-6-oxo-5-azaspiro[2.4]heptan-4-yl)methoxy)-7-isopropoxyisoquinoline-6-carboxamide (300 mg, 71% yield) as a white solid.

The enantiomers were separated by preparative chiral SFC chromatography. Instrument: SFC-200 Column: Chiralpak AS 300×50 mm I.D., 10 μm. Mobile phase: Supercritical $CO_2$/MeOH (0.1% $NH_3H_2O$)=55/45 at 200 mL/min Column Temp: 38° C. Nozzle Pressure: 100 Bar. Nozzle Temp: 60° C. Evaporator Temp: 20° C. Trimmer Temp: 25° C.

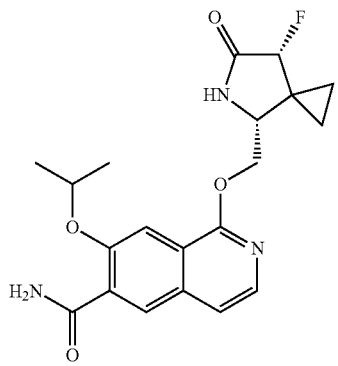 [SMILES: CC(C)Oc1cc2c(OC[C@@H]3NC(=O)[C@H](F)C34CC4)nccc2cc1C(N)=O]

1-(((4R,7R)-7-fluoro-6-oxo-5-azaspiro[2.4]heptan-4-yl)methoxy)-7-isopropoxyisoquinoline-6-carboxamide Analytical SFC chromatography Column: Chiralpak AS-H 150×4.6 mm I.D., 5 μm. Mobile phase: methanol (0.05% DEA) in $CO_2$ from 5% to 40%. Flow rate: 3 mL/min. Wavelength: 220 nm. Analytical SFC chromatography Retention Time: 4.161 min. $^1$H NMR (400 MHz, DMSO-d6) δ 8.96 (s, 1H), 8.18 (s, 1H), 7.88 (d, 1H), 7.77-7.67 (m, 3H), 7.41 (d, 1H), 4.86 (td, 1H), 4.72-4.52 (m, 1H), 4.46 (dd, 1H), 4.22 (dd, 1H), 3.73 (d, 1H), 1.37 (t, 6H), 1.08-0.93 (m, 4H). MS m/z 388.1 [M+H]$^+$ and MS m/z 410.0 [M+Na]$^+$.

Example 19

1-(((4S,7S)-7-fluoro-6-oxo-5-azaspiro[2.4]heptan-4-yl)methoxy)-7-isopropoxyisoquinoline-6-carboxamide

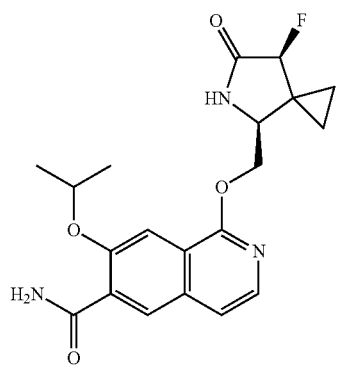 [SMILES: CC(C)Oc1cc2c(OC[C@H]3NC(=O)[C@@H](F)C34CC4)nccc2cc1C(N)=O]

Analytical SFC chromatography Column: Chiralpak AS-H 150×4.6 mm I.D., 5 μm. Mobile phase: methanol (0.05% DEA) in $CO_2$ from 5% to 40%. Flow rate: 3 mL/min. Wavelength: 220 nm. Analytical SFC chromatography Retention Time: 6.239 min. $^1$H NMR (400 MHz, DMSO-d6) δ 8.96 (s, 1H), 8.18 (s, 1H), 7.88 (d, 1H), 7.77-7.67 (m, 3H), 7.41 (d, 1H), 4.86 (td, 1H), 4.72-4.52 (m, 1H), 4.46 (dd, 1H), 4.22 (dd, 1H), 3.73 (d, 1H), 1.37 (t, 6H), 1.08-0.93 (m, 4H). MS m/z [M+H]+ 387.9 and MS m/z [M+Na]+ 409.9.

Example 21

1-(((4S,7R)-7-fluoro-6-oxo-5-azaspiro[2.4]heptan-4-yl)methoxy)-7-methoxyisoquinoline-6-carboxamide

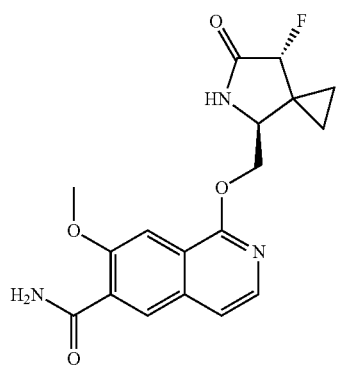 [SMILES: COc1cc2c(OC[C@H]3NC(=O)[C@H](F)C34CC4)nccc2cc1C(N)=O]

Step 1: Preparation of 1-((7-fluoro-6-oxo-5-azaspiro [2.4]heptan-4-yl)methoxy)-7-methoxyisoquinoline-6-carbonitrile

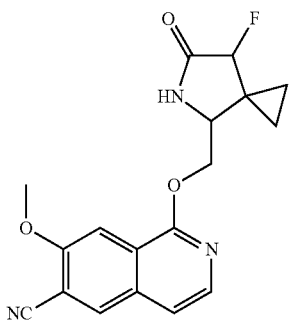 [SMILES: COc1cc2c(OCC3NC(=O)C(F)C34CC4)nccc2cc1C#N]

To a mixture of 1-chloro-7-methoxyisoquinoline-6-carbonitrile (650 mg, 2.97 mmol) and 7-fluoro-4-(hydroxymethyl)-5-azaspiro[2.4]heptan-6-one (530 mg, 3.33 mmol) in DMF (15.0 mL) at 0° C. was added KHMDS (6.54 mL, 1 M in THF) dropwise. The resulting solution was stirred at 0° C. for 1 h. The reaction mixture was allowed to warm to 30° C. and was stirred for 2 h. The reaction mixture was quenched with aq. NH₄Cl (10 mL) and was partitioned between H₂O/EtOAc (100 mL/100 mL). The aqueous layer was extracted with EtOAc (100 mL×2). To the organic layer was added MeOH (100 mL). The organic layer was dried over MgSO₄ then filtered and the solvent was removed under reduced pressure. The filter cake was slurried with 150 mL EtOAc and stirred for 18 hours at 35° C. then filtered and the solvent was evaporated. The filtrates were combined, concentrated and purified by flash column (EtOAc: petroleum ether from 50% to 70%) to give two fractions (140 mg and 657 mg) as yellow solids.

The first fractions (140 mg) were mixed with another batch prepared in the same manner, and purified by flash column (EtOAc: petroleum ether from 40% to 55%) to give 335 mg of an early fraction (23% yield) as a yellow solid. This material was converted to the carboxamide and its enantiomers separated at that stage.

Racemic 1-(((anti)-7-fluoro-6-oxo-5-azaspiro[2.4] heptan-4-yl)methoxy)-7-methoxyisoquinoline-6-carbonitrile

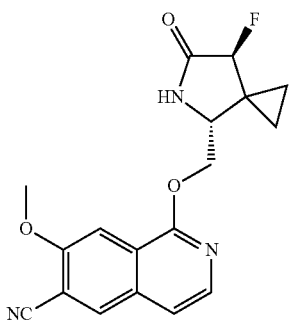 [SMILES: COc1cc2c(OC[C@@H]3NC(=O)[C@@H](F)C34CC4)nccc2cc1C#N]

Early fraction ¹H NMR (400 MHz, DMSO-d6) δ 8.97 (s, 1H), 8.54 (s, 1H), 7.99 (d, 1H), 7.63 (s, 1H), 7.43 (d, 1H), 5.18-4.96 (m, 1H), 4.47-4.38 (m, 1H), 4.37-4.29 (m, 1H), 4.05 (s, 3H), 3.84 (dd, 1H), 1.11-1.01 (m, 2H), 0.89-0.76 (m, 2H). MS m/z 342.0 [M+H]⁺.

Racemic 1-(((syn)-7-fluoro-6-oxo-5-azaspiro[2.4] heptan-4-yl)methoxy)-7-methoxyisoquinoline-6-carbonitrile

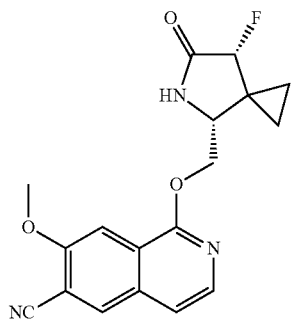 [SMILES: COc1cc2c(OC[C@@H]3NC(=O)[C@H](F)C34CC4)nccc2cc1C#N]

The second fractions (657 mg) were mixed with another batch prepared in the same manner and purified to give a 500 mg late fraction (34% yield) as yellow solid. This material was separately converted to the carboxamide and its enantiomers separated at that stage. Late fraction ¹H NMR (400 MHz, DMSO-d6) δ 9.03 (s, 1H), 8.51 (s, 1H), 7.98 (d, 1H), 7.81 (s, 1H), 7.41 (d, 1H), 4.70-4.52 (m, 1H), 4.49 (dd, 1H), 4.21 (dd, 1H), 4.01 (s, 3H), 3.74 (br. s., 1H), 1.10-0.97 (m, 4H). MS m/z 342.0 [M+H]⁺.

Step 2: Preparation of Racemic 1-(((anti)-7-fluoro-6-oxo-5-azaspiro[2.4]heptan-4-yl)methoxy)-7-methoxyisoquinoline-6-carboxamide

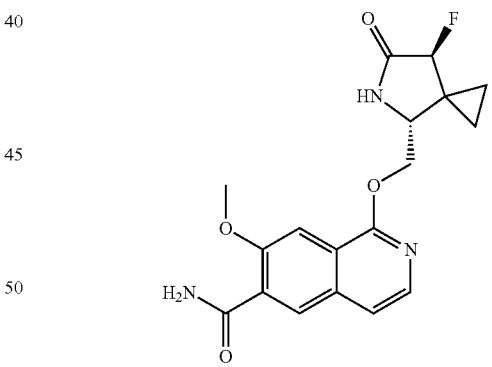

A yellow mixture of racemic 1-(((anti)-7-fluoro-6-oxo-5-azaspiro[2.4]heptan-4-yl)methoxy)-7-methoxyisoquinoline-6-carbonitrile (230 mg, 0.67 mmol) from Step 1 and K₂CO₃ (466 mg, 1.46 mmol) in DMSO (8.0 mL) was stirred at 30° C. for 5 min, and then H₂O₂ (0.46 mL, 15 mmol) was added slowly. The resulting mixture was stirred at 30° C. for 2 h. To the reaction mixture was added H₂O (18 mL) at 0-5° C. and the mixture was stirred for 1 hour. The mixture was filtered and the filter cake was washed with H₂O (20 mL×4). The residue was dried under reduced pressure to give the crude product (202 mg, 84% yield) as an off-white solid. The enantiomers were separated by SFC. MS m/z 382.1 [M+Na]⁺. Enantiomer separation: Chiral SFC Chromatography: Column: AD (250 mm×30 mm, 5 μm) Mobile phase: EtOH:CO$_2$=40:60 (0.1% NH$_4$OH). Flow rate: 50 mL/min. Wavelength: 220 nm 1-(((4S,7R)-7-fluoro-6-oxo-5-azaspiro[2.4]heptan-4-yl)methoxy)-7-methoxyisoquinoline-6-carboxamide

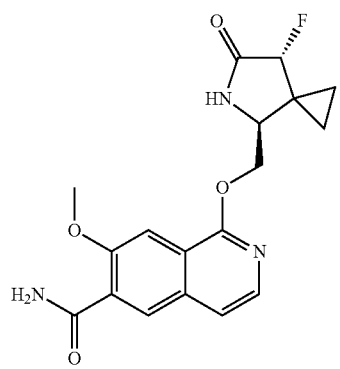 [SMILES: COc1cc2c(OC[C@H]3NC(=O)[C@H](F)C34CC4)nccc2cc1C(N)=O]

Analytical chiral chromatography: Column: AD (250 mm×30 mm, 5 μm) Mobile phase: EtOH:CO$_2$=40:60 (0.1% NH$_4$OH). Flow rate: 50 mL/min. Wavelength: 220 nm. Retention time 6.437 min. $^1$H NMR (400 MHz, DMSO-d6) δ 8.92 (s, 1H), 8.17 (s, 1H), 7.90 (d, 1H), 7.85 (br. s., 1H), 7.72 (br. s., 1H), 7.53 (s, 1H), 7.44 (d, 1H), 5.18-4.97 (m, 1H), 4.44-4.31 (m, 2H), 3.98 (s, 3H), 3.82 (t, 1H), 1.11-1.01 (m, 2H), 0.90-0.75 (m, 2H). MS m/z 382.1 [M+Na]$^+$.

Example 22

1-(((4R,7S)-7-fluoro-6-oxo-5-azaspiro[2.4]heptan-4-yl)methoxy)-7-methoxyisoquinoline-6-carboxamide

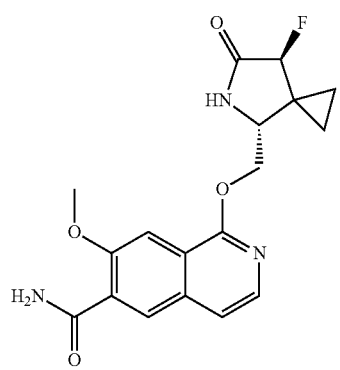 [SMILES: COc1cc2c(OC[C@@H]3NC(=O)[C@@H](F)C34CC4)nccc2cc1C(N)=O]

Analytical chiral chromatography: Column: AD (250 mm×30 mm, 5 μm) Mobile phase: EtOH:CO$_2$=40:60 (0.1% NH$_4$OH). Flow rate: 50 mL/min. Wavelength: 220 nm. Retention time 7.090 min. $^1$H NMR (400 MHz, DMSO-d6) δ 8.90 (s, 1H), 8.17 (s, 1H), 7.90 (d, 1H), 7.84 (br. s., 1H), 7.70 (br. s., 1H), 7.53 (s, 1H), 7.44 (d, 1H), 5.17-4.96 (m, 1H), 4.44-4.33 (m, 2H), 3.98 (s, 3H), 3.85-3.79 (m, 1H), 1.07 (d, 2H), 0.89-0.73 (m, 2H). MS m/z 382.1 [M+Na]$^+$.

Example 23

1-(((4R,7R)-7-fluoro-6-oxo-5-azaspiro[2.4]heptan-4-yl)methoxy)-7-methoxyisoquinoline-6-carboxamide

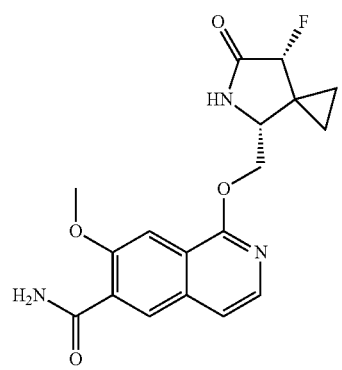 [SMILES: COc1cc2c(OC[C@@H]3NC(=O)[C@H](F)C34CC4)nccc2cc1C(N)=O]

A mixture of racemic 1-(((syn)-7-fluoro-6-oxo-5-azaspiro[2.4]heptan-4-yl)methoxy)-7-methoxyisoquinoline-6-carbonitrile (350 mg, 1.02 mmol) from Example 21, Step 1, and K$_2$CO$_3$ (709 mg, 2.20 mmol) in DMSO (10.4 mL) was stirred at 30° C. for 5 min, and then H$_2$O$_2$ (0.90 mL, 29 mmol) was added slowly. The resulting white slurry was stirred at 30° C. for 2 h. To the reaction mixture was added H$_2$O (30 mL) at 0-5° C., and the mixture was stirred for 1 h. The mixture was filtered and the filter cake was washed with H$_2$O (30 mL×3). The residue was dried under reduced pressure to afford crude product (350 mg, 95% yield) as an off-white solid. The enantiomers were separated by SFC chromatography. MS m/z 360.0 (M+H)$^+$. Enantiomer separation by Chiral SFC Chromatography: Column: AD (250 mm×30 mm, 5 μm) Mobile phase: EtOH:CO$_2$=40:60 (0.1% NH$_4$OH). Flow rate: 50 mL/min. Wavelength: 220 nm.

1-(((4R,7R)-7-fluoro-6-oxo-5-azaspiro[2.4]heptan-4-yl)methoxy)-7-methoxyisoquinoline-6-carboxamide. Analytical Chiral SFC Chromatography: Column: AD (250 mm×30 mm, 5 μm) Mobile phase: EtOH:CO$_2$=30:70 (0.1% NH$_4$OH). Flow rate: 60 mL/min. Wavelength: 220 nm. Retention time 6.687 min. $^1$H NMR (400 MHz, DMSO-d6) δ 9.00 (s, 1H), 8.15 (s, 1H), 7.89 (d, 1H), 7.84 (br. s., 1H), 7.74 (s, 1H), 7.69 (br. s., 1H), 7.42 (d, 1H), 4.70-4.52 (m, 1H), 4.48 (dd, 1H), 4.23 (dd, 1H), 3.95 (s, 3H), 3.74 (br. s., 1H), 1.02 (br. s., 4H). MS m/z 359.9 [M+H]$^+$.

Example 24

1-(((4S,7S)-7-fluoro-6-oxo-5-azaspiro[2.4]heptan-4-yl)methoxy)-7-methoxyisoquinoline-6-carboxamide

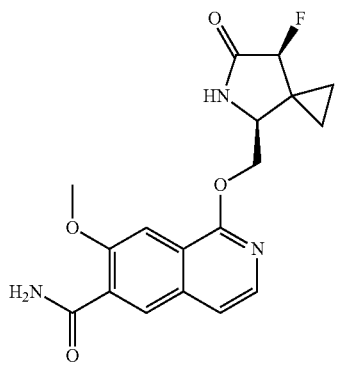 [SMILES: COc1cc2c(OC[C@H]3NC(=O)[C@@H](F)C34CC4)nccc2cc1C(N)=O]

Analytical Chiral SFC Chromatography: Column: AD (250 mm×30 mm, 5 μm) Mobile phase: EtOH:CO$_2$=30:70 (0.1% NH$_4$OH). Flow rate: 60 mL/min. Retention time 6.829 min $^1$H NMR (400 MHz, DMSO-d6) δ 9.00 (s, 1H), 8.15 (s, 1H), 7.89 (d, 1H), 7.84 (br. s., 1H), 7.74 (s, 1H), 7.69 (br. s., 1H), 7.42 (d, 1H), 4.70-4.52 (m, 3H), 4.48 (d, 2H), 4.22 (br. s., 2H), 3.95 (s, 3H), 3.74 (br. s., 1H), 1.02 (br. s., 4H). MS m/z 360.0 [M+H]$^+$.

Example 25

4-(((2S,3R)-3-ethyl-5-oxopyrrolidin-2-yl)methoxy)-6-methoxyisoquinoline-7-carboxamide

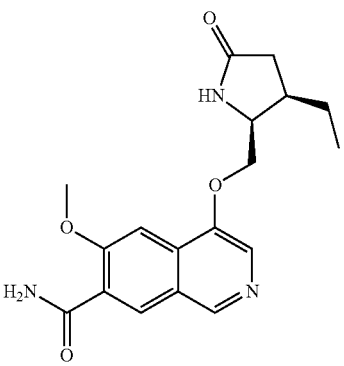 [SMILES: CC[C@@H]1CC(=O)N[C@@H]1COc1cncc2cc(C(N)=O)c(OC)cc12]

Step 1: Preparation of Ethyl N-(3-bromo-4-methoxybenzyl)glycinate

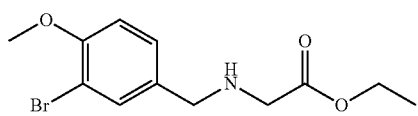 [SMILES: CCOC(=O)CNCc1ccc(OC)c(Br)c1]

The preparation of ethyl N-(3-bromo-4-methoxybenzyl) glycinate was carried out in five parallel batches. To a solution of 3-bromo-4-methoxybenzaldehyde (5.0 g, 20 mmol), and ethyl glycinate (8.12 g, 58.1 mmol, HCl salt) in DCM (120 mL) was added TEA (5.12 g, 50.7 mmol), followed by AcOH (3.07 g, 51.2 mmol) and NaBH(OAc)$_3$ (11.8 g, 55.8 mmol). The mixture was stirred at 15° C. under nitrogen atmosphere overnight. A total of five batches were prepared in this manner and combined for workup and purification. The resulting mixture was poured into saturated aqueous NaHCO$_3$ (500 mL), and extracted with DCM. The combined organic phases were dried over Na$_2$SO$_4$, filtered, and the solvent was removed to give a crude oil, which was subsequently purified by silica gel chromatography using EtOAc/petroleum ether (20% to 100%) to give the title compound as an oil (26 g, 74% yield). $^1$H NMR (400 MHz, DMSO-d6) δ 7.43-7.59 (m, 1H), 7.26 (dd, 1H), 7.03 (d, 1H), 4.08 (q, 2H), 3.82 (s, 3H), 3.63 (s, 2H), 3.26 (s, 2H), 1.18 (t, 3H). MS m/z 304 [M+H]$^+$.

Step 2: Preparation of Ethyl N-(3-bromo-4-methoxybenzyl)-N-[(4-methylphenyl)sulfonyl]glycinate

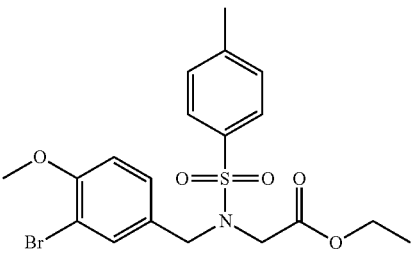 [SMILES: CCOC(=O)CN(Cc1ccc(OC)c(Br)c1)S(=O)(=O)c1ccc(C)cc1]

The preparation of ethyl N-(3-bromo-4-methoxybenzyl)-N-[(4-methylphenyl)sulfonyl]glycinate was carried out in five parallel batches. To a solution of ethyl N-(3-bromo-4-methoxybenzyl)glycinate (5000 mg, 16.5 mmol) and pyridine (6540 mg, 82.7 mmol) in THF (60 mL) was added p-toluenesulfonyl chloride (3150 mg, 16.5 mmol) at 0° C. The mixture was stirred at 15° C. overnight. To the mixture was added DMAP (202 mg, 1.65 mmol) and the mixture was stirred at 15° C. overnight. A total of five batches were prepared in this manner and combined for workup and purification. The mixture was acidified with concentrated HCl to pH 3 and extracted with DCM. The combined organic layers were washed with anhydrous Na$_2$SO$_4$, concentrated in vacuo and purified by silica gel chromatography (EtOAc/petroleum ether from 8% to 20%) to give the title compound as a white solid (21 g, 56% yield) (84% purity by LCMS). $^1$H NMR (400 MHz, CDCl$_3$) δ 7.76 (d, 2H), 7.30-7.36 (m, 3H), 7.19 (dd, 1H), 6.83 (d, 1H), 4.40 (s, 2H), 4.02 (q, 2H), 3.90 (s, 2H), 3.88 (s, 3H), 2.45 (s, 3H), 1.16 (t, 3H). MS m/z 477.8 [M+Na]$^+$.

Step 3: Preparation of N-(3-Bromo-4-methoxybenzyl)-N-[(4-methylphenyl)sulfonyl]glycine

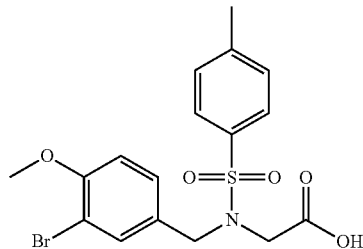 [SMILES: COc1ccc(CN(CC(=O)O)S(=O)(=O)c2ccc(C)cc2)cc1Br]

To a solution of ethyl N-(3-bromo-4-methoxybenzyl)-N-[(4-methylphenyl)sulfonyl]glycinate (10.0 g, 21.9 mmol) in a mixture of THF/MeOH (70 mL/70 mL) was added a solution of LiOH.H$_2$O (1840 mg, 43.8 mmol) in H$_2$O (50 mL) at 15° C. The mixture was stirred at this temperature for 4 h. The mixture was concentrated in vacuo and diluted with H$_2$O (100 mL), then acidified with concentrated HCl to pH 3. The resulting mixture was extracted with DCM, dried over anhydrous Na$_2$SO$_4$, filtered and concentrated in vacuo to give the title compound as a white solid (9 g, 96% yield). $^1$H NMR (400 MHz, CDCl$_3$) δ 7.76 (d, 2H), 7.34 (d, 2H), 7.28 (d, 1H), 7.17 (dd, 1H), 6.84 (d, 1H), 4.39 (s, 2H), 3.94 (s, 2H), 3.89 (s, 3H), 2.44-2.50 (m, 3H). MS m/z 449.7 [M+Na]$^+$.

Step 4: Preparation of N-(3-Bromo-4-methoxybenzyl)-N-[(4-methylphenyl)sulfonyl]glycyl chloride

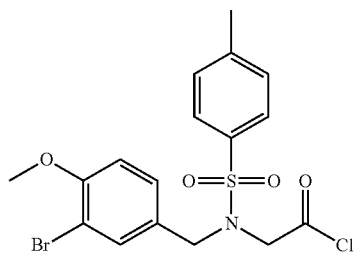 [SMILES: COc1ccc(CN(CC(=O)Cl)S(=O)(=O)c2ccc(C)cc2)cc1Br]

A solution of N-(3-bromo-4-methoxybenzyl)-N-[(4-methylphenyl)sulfonyl]glycine (3000 mg, 7.00 mmol) was co-evaporated with dry toluene (30 mL×3) to remove water and was dissolved in dry DCM (75 mL). To the mixture was added oxalyl chloride (4450 mg, 35.0 mmol) and DMF (3 drops) at 15° C. under nitrogen. The mixture was stirred for 2 h. The solution was evaporated to give crude title compound as a yellow solid (3130 mg, ~100%), which was used directly in the next step. MS m/z 465 [M+Na]$^+$.

Step 5: Preparation of 7-Bromo-6-methoxy-2-[(4-methylphenyl)sulfonyl]-2,3-dihydroisoquinolin-4(1H)-one

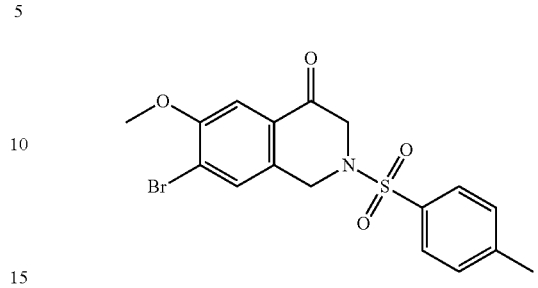

To a solution of N-(3-romo-4-methoxybenzyl)-N-[(4-methylphenyl)sulfonyl]glycyl chloride (3130 mg, 7.01 mmol) in DCM (15 mL) was added AlCl$_3$ (2340 mg, 17.5 mmol) in one portion at −65° C. The reaction mixture was stirred for 1 h at −65° C. then slowly warmed to 0° C. and stirred for 1 h. The reaction mixture was quenched with water (15 mL). The mixture was extracted with DCM and dried over anhydrous Na$_2$SO$_4$. The crude product was purified by silica gel chromatography using petroleum ether: EtOAc (20:1 to 3:1) as eluent to give the title compound as a yellow solid (1.2 g, 41% yield). $^1$H NMR (400 MHz, CDCl$_3$) δ 7.63 (d, 2H), 7.48 (s, 1H), 7.32 (s, 1H), 7.27 (t, 2H), 4.44 (s, 2H), 4.00 (s, 2H), 3.90 (s, 3H), 2.40 (s, 3H).

Step 6: Preparation of 7-Bromo-6-methoxyisoquinolin-4-ol

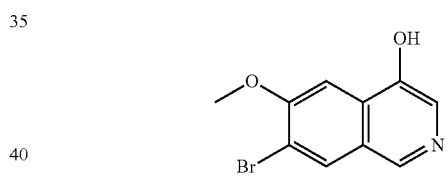

To a solution of 7-bromo-6-methoxy-2-[(4-methylphenyl)sulfonyl]-2,3-dihydroisoquinolin-4(1H)-one (2700 mg, 6.58 mmol) in EtOH (68 mL) was added NaHCO$_3$ (2210 mg, 26.3 mmol). The mixture was heated to reflux for 3 h. The mixture was filtered and the filter cake was washed with acetone. The filtrate was concentrated to give the crude product which was purified by silica gel chromatography using DCM:MeOH (100:1 to 8:1) as eluent to give the title compound as a yellow solid (1400 mg, 83% yield). $^1$H NMR (400 MHz, DMSO-d6) δ 10.46 (br s, 1H), 8.66 (s, 1H), 8.38 (s, 1H), 8.02 (s, 1H), 7.46 (s, 1H), 4.00 (s, 3H).

Step 7: Preparation of 4-Hydroxy-6-methoxyisoquinoline-7-carbonitrile

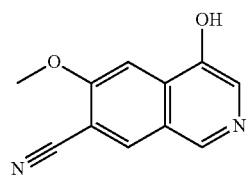

To a solution of 7-bromo-6-methoxyisoquinolin-4-ol (1400 mg, 5.51 mmol, 1 eq.) in DMF (65 mL) was added Zn(CN)$_2$ (3240 mg, 27.6 mmol) and Pd(PPh$_3$)$_4$ (637 mg, 0.551 mmol) at 15° C. The suspension was degassed under vacuum and purged with nitrogen twice. The reaction was stirred for 10 min at 15° C. then for 6 h at 140° C. The DMF was evaporated. The residue was purified by silica gel chromatography using DCM:MeOH (50:1 to 10:1) as eluent to give a crude product which was triturated with DCM and filtered to give the title compound (750 mg, ~68% yield), contaminated with residual DCM. The mother liquor was concentrated to give crude title compound (785 mg, ~71% yield), contaminated with residual DCM. $^1$H NMR (400 MHz, DMSO-d6) δ 10.72 (s, 1H), 8.76 (s, 1H), 8.70 (s, 1H), 8.11 (s, 1H), 7.52 (s, 1H), 4.04 (s, 3H). MS m/z 201 [M+H]$^+$.

Step 8: Preparation of 4-(((2S,3R)-3-ethyl-5-oxopyrrolidin-2-yl)methoxy)-6-methoxyisoquinoline-7-carbonitrile

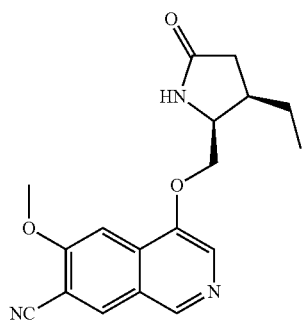 [SMILES: CC[C@@H]1CC(=O)N[C@@H]1COc1cncc2cc(C#N)c(OC)cc12]

A mixture of diisopropylazodicarboxylate (DIAD) (253 mg, 1.25 mmol) and triphenylphosphine (328 mg, 1.25 mmol) in THF (8 mL) was stirred for 10 min under N$_2$ atmosphere. 4-Hydroxy-6-methoxyisoquinoline-7-carbonitrile (100 mg, 0.50 mmol) was added and the mixture was stirred for about 10 min. To this mixture was added (4R,5S)-4-ethyl-5-(hydroxymethyl)pyrrolidin-2-one (93 mg, 0.6t mmol). The mixture was stirred and heated to 65° C. for 16 h under N$_2$. The reaction mixture was concentrated under reduced pressure and purified by silica gel flash chromatography (0% to 15% MeOH in EtOAc) to give the desired product (106 mg, 57% purity by H NMR, ~37% yield) as a pale yellow solid. MS m/e 325.9 [M+H]$^+$.

Step 9: Preparation of 4-(((2S,3R)-3-ethyl-5-oxopyrrolidin-2-yl)methoxy)-6-methoxyisoquinoline-7-carboxamide To a solution of 4-(((2S,3R)-3-ethyl-5-oxopyrrolidin-2-yl)methoxy)-6-methoxyisoquinoline-7-carbonitrile (106 mg, 0.19 mmol) in DMSO (4 mL) were added K$_2$CO$_3$ (128 mg, 0.93 mmol) and H$_2$O$_2$ (147 mg, 30% w/w solution in water, 1.30 mmol) at 20° C. The reaction mixture was stirred at 20° C. for 2 h and was then diluted with water (20 mL) and extracted with 10:1 DCM/MeOH (4×25 mL). The combined organic phase was washed with brine, dried over Na$_2$SO$_4$, filtered and concentrated to give a crude product which was purified by HPLC. Column: Phenomenex Gemini C18 250×21.2 mm×8 um Gradient Time: 10 min. Mobile phase: from 19% MeCN in water (ammonia) to 39% MeCN in water (ammonia). Flow rate: 30 mL/min. Wavelength: 220 nm the desired fractions were concentrated under reduced pressure to give the desired product (20 mg) as a white solid. $^1$H NMR (400 MHz, MeOD) δ 8.86 (s, 1H), 8.59 (s, 1H), 8.08 (s, 1H), 7.54 (s, 1H), 4.46 (dd, 1H), 4.25 (dd, 1H), 4.14-4.07 (m, 2H), 4.11 (s, 3H), 2.78-2.63 (m, 1H), 2.58-2.46 (m, 1H), 2.45-2.33 (m, 1H), 1.80-1.67 (m, 1H), 1.60-1.45 (m, 1H), 1.03 (t, 3H). MS m/e 344.1 [M+H]$^+$.

Example 26

4-(((2S,3S,4S)-3-ethyl-4-fluoro-5-oxopyrrolidin-2-yl)methoxy)-6-methoxyisoquinoline-7-carboxamide

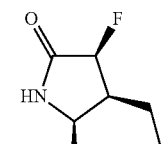
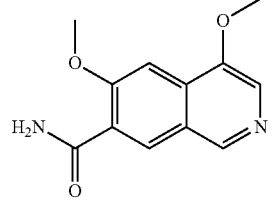

Step 1: Preparation of 4-(((2S,3S,4S)-3-ethyl-4-fluoro-5-oxopyrrolidin-2-yl)methoxy)-6-methoxyisoquinoline-7-carbonitrile

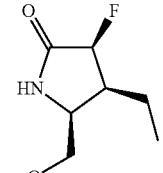
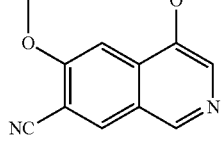

A mixture of diisopropylazodicarboxylate (DIAD) (253 mg, 1.25 mmol) and triphenylphosphine (328 mg, 1.25 mmol) in THF (8 mL) was stirred for 10 min under N$_2$ atmosphere. 4-Hydroxy-6-methoxyisoquinoline-7-carbonitrile (100 mg, 0.50 mmol) was added and the mixture was stirred for about 10 min. (3S,4S,5S)-4-Ethyl-3-fluoro-5-(hydroxymethyl)pyrrolidin-2-one (161 mg, 0.99 mmol) was added, and the mixture was stirred at 65° C. for 16 h under N$_2$ atmosphere. The reaction mixture was concentrated under reduced pressure to give a residue which was purified silica gel flash chromatography (100% EtOAc to 15% MeOH in EtOAc) to give the desired product (25 mg, 4% yield) as a pale yellow oil. MS m/e 343.9 [M+H]$^+$.

Step 2: Preparation of 4-(((2S,3S,4S)-3-ethyl-4-fluoro-5-oxopyrrolidin-2-yl)methoxy)-6-methoxyisoquinoline-7-carboxamide To a solution of 4-(((2S,3S,4S)-3-ethyl-4-fluoro-5-oxopyrrolidin-2-yl)methoxy)-6-methoxyisoquinoline-7-carbonitrile (25 mg, 0.051 mmol) in DMSO (1 mL) were added K$_2$CO$_3$ (35.2 mg, 0.255 mmol) and H$_2$O$_2$ (40.5 mg, 30% w/w solution in water, 0.357 mmol). The reaction mixture was stirred for 2 h. The reaction mixture was diluted with water (15 mL) and was extracted with 10:1 DCM/MeOH (4×20 mL). The combined organic phase was washed with brine, dried over Na$_2$SO$_4$, filtered and concentrated to give a crude product which was purified by HPLC. Column: Phenomenex Gemini C18 250×21.2 mm×8 um. Gradient Time: 11 min. Mobile phase: from 19% MeCN in water (ammonia) to 39% MeCN in water (ammonia). Flow rate: 35 mL/min Wavelength: 220 nm. The desired fractions were concentrated under reduced pressure to give the desired product (15 mg) as a white solid. $^1$H NMR (400 MHz, MeOD) δ 8.85 (s, 1H), 8.59 (s, 1H), 8.04 (s, 1H), 7.80 (s, 1H), 5.07 (d, 0.5H), 4.94 (d, 0.5H), 4.31 (d, 2H), 4.21 (dd, 1H), 2.85-2.67 (m, 1H), 1.88-1.64 (m, 2H), 1.12 (t, 3H). MS m/e 383.9 [M+Na]$^+$.

Example 27

5-(((2S,3S,4S)-3-ethyl-4-fluoro-5-oxopyrrolidin-2-yl)methoxy)-3-methoxy-2-naphthamide

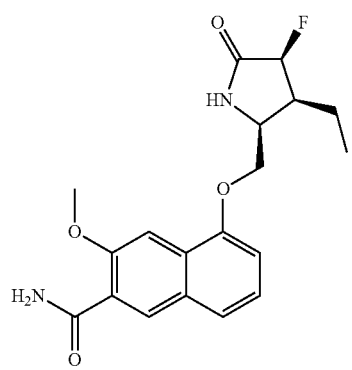 [SMILES: CC[C@@H]1[C@H](F)C(=O)N[C@@H]1COc1cccc2cc(C(N)=O)c(OC)cc12]

Step 1: Preparation of 5-hydroxy-3-methoxy-2-naphthonitrile

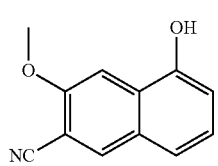

To a stirred suspension of 5-hydroxy-3-methoxy-2-naphthamide (233 mg, 1.07 mmol) in 1,4-dioxane (10 mL) was added dropwise pyridine (679 mg, 8.58 mmol). TFAA (901 mg, 4.29 mmol) was added dropwise over 10 min under N$_2$ atmosphere. The reaction mixture was stirred for 2 h under N$_2$ atmosphere. The reaction mixture was diluted with EtOAc (100 mL), washed with water (2×50 mL), brine (50 mL), dried over Na$_2$SO$_4$, filtered and concentrated to give 5-hydroxy-3-methoxy-2-naphthonitrile (210 mg, 98% yield) as an orange solid. $^1$H NMR (400 MHz, DMSO-d6) δ 10.43 (s, 1H), 8.43 (s, 1H), 7.57 (s, 1H), 7.40 (d, 1H), 7.33-7.23 (m, 1H), 7.01 (d, 1H), 3.99 (s, 3H).

Step 2: Preparation of [(2S,3S,4S)-3-ethyl-4-fluoro-5-oxopyrrolidin-2-yl]methyl methanesulfonate

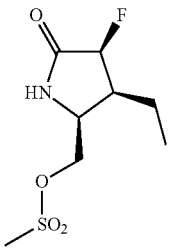

To a solution of (3S,4S,5S)-4-ethyl-3-fluoro-5-(hydroxymethyl)pyrrolidin-2-one (400 mg, 2.48 mmol) in DCM (25 mL) was added methanesulfonyl chloride (398 mg, 3.47 mmol) and TEA (502 mg, 4.96 mmol) at 0° C. under N$_2$ atmosphere. The reaction mixture was stirred under N$_2$ for 1 h at 20° C. The mixture was diluted with DCM (80 mL), washed with saturated NaHCO$_3$ solution (40 mL), brine (40 mL), dried over Na$_2$SO$_4$, filtered and concentrated to give the desired product (580 mg, ~98% yield) as a pale yellow oil which was used without further purification. $^1$H NMR (400 MHz, CDCl$_3$) δ 6.95 (br. s., 1H), 4.87 (d, 0.5H), 4.74 (d, Hz, 0.5H), 4.40 (dd, Hz, 1H), 4.11 (t, 1H), 4.04-3.94 (m, 1H), 2.57-2.48 (m, 1H), 2.48-2.37 (m, 1H), 1.76-1.48 (m, 1H), 1.63 (s, 3H), 1.09 (t, 3H).

Step 3: Preparation of 5-(((2S,3S,4S)-3-ethyl-4-fluoro-5-oxopyrrolidin-2-yl)methoxy)-3-methoxy-2-naphthonitrile

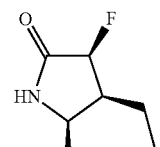

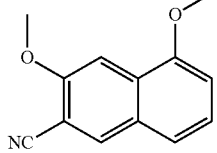

To a solution of 5-hydroxy-3-methoxy-2-naphthonitrile (350 mg, 1.76 mmol) in dry DMF (20 mL) was added [(2S,3S,4S)-3-ethyl-4-fluoro-5-oxopyrrolidin-2-yl]methyl methanesulfonate (580 mg, 2.42 mmol) and K$_2$CO$_3$ (486 mg, 3.51 mmol). The mixture was stirred at 60° C. for 6 h, and then was diluted with EtOAc (160 mL), washed with brine (3×60 mL), water (60 mL) and brine (60 mL), and dried over MgSO$_4$. The crude product was purified by silica gel chromatography using petroleum ether/EtOAc (2:1 to 1:4) to give the desired product (370 mg, 61% yield) as a pale yellow solid. $^1$H NMR (400 MHz, CDCl$_3$) δ 8.02 (s, 1H), 7.57 (s, 1H), 7.49 (br. s., 1H), 7.40-7.34 (m, 1H), 7.32-7.28 (m, 1H), 6.84 (d, 1H), 5.00-4.80 (m, 1H), 4.20 (d, 2H), 4.17-4.08 (m, 1H), 3.98 (s, 3H), 2.71-2.47 (m, 1H), 1.86-1.73 (m, 1H), 1.69-1.54 (m, 1H), 1.11 (t, 3H). MS m/e 342.9 [M+H]$^+$.

Step 4: Preparation of 5-{[(2S,3S,4S)-3-ethyl-4-fluoro-5-oxopyrrolidin-2-yl]methoxy}-3-methoxynaphthalene-2-carboxamide To a solution of 5-{[(2S,3S,4S)-3-ethyl-4-fluoro-5-oxopyrrolidin-2-yl]methoxy}-3-methoxynaphthalene-2-carboxamide (430 mg, 1.26 mmol) in DMSO (5 mL) were added K$_2$CO$_3$ (868 mg, 6.28 mmol) and H$_2$O$_2$ (997 mg, 30% w/w solution in water, 8.79 mmol). After 2 h, the reaction mixture was diluted with DCM (120 mL), and washed with brine (2×40 mL), water (30 mL) and brine (30 mL), and dried over Na$_2$SO$_4$, filtered and concentrated to give a crude product, which was triturated with DCM (10 mL). The mixture was filtered and the cake was washed with water (2×8 mL) and DCM (6 mL). The cake was collected and dried in vacuo to give the desired product (330 mg, 73% yield) as an off-white solid. $^1$H NMR (400 MHz, DMSO-d6) δ 8.83 (s, 1H), 8.26 (s, 1H), 7.78 (br. s., 1H), 7.73 (s, 1H), 7.63 (br. s., 1H), 7.52 (d, 1H), 7.29 (t, 1H), 7.02 (d, 1H), 5.03-4.80 (m, 1H), 4.20-4.00 (m, 3H), 3.96 (s, 3H), 2.72-2.53 (m, 1H), 1.71-1.53 (m, 2), 1.01 (t, 3H). MS m/e 360.9 [M+H]$^+$. MS m/e 382.8 [M+Na]$^+$.

Example 28

(3S,6R)-5-oxo-2,3,4,5,6,7,9,10-octahydro-12,14-(ethanediylidene)-3,6-methanopyrido[2,3-l][1,4,11,8]trioxazacyclopentadecine-19-carboxamide

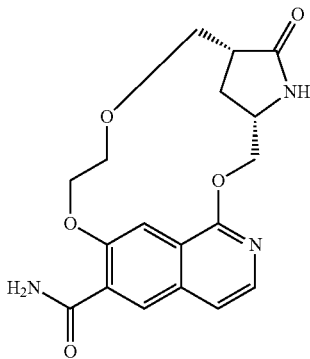 [SMILES: NC(=O)c1cc2ccnc3c2cc1OCCOC[C@H]1C[C@@H](CO3)NC1=O]

Step 1: Preparation of (6R,7aS)-6-((2-chloroethoxy)methyl)-3,3-dimethyltetrahydro-3H,5H-pyrrolo[1,2-c]oxazol-5-one

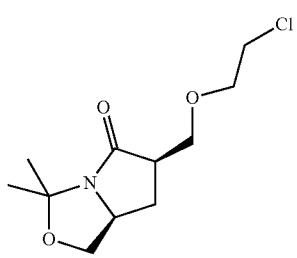 [SMILES: CC1(C)OC[C@@H]2C[C@H](COCCCl)C(=O)N21]

To a stirred solution of (S)-3,3-dimethyltetrahydro-3H,5H-pyrrolo[1,2-c]oxazol-5-one (5 g, 32.2 mmol) in dry THF (100 mL) was added LDA (2 M solution in THF/heptane/ethylbenzene, 20 mL, 40.3 mmol) at −78° C. under nitrogen atmosphere. After 30 min, 1-chloro-2-(chloromethoxy)ethane (3.58 mL, 35.5 mmol) was added dropwise and stirred 10 min at −78° C. The mixture was allowed to warm to room temperature and was stirred for 1 h and was then quenched with EtOAc:water (1:1). The aqueous layer was extracted with EtOAc. The organic phase was washed with brine and dried over Na$_2$SO$_4$. The residue was purified by silica gel column chromatography (0-20% EtOAc-hexane) to afford (6R,7aS)-6-((2-chloroethoxy)methyl)-3,3-dimethyltetrahydro-3H,5H-pyrrolo[1,2-c]oxazol-5-one (1.25 g, 16%) and the isomer (1.1 g, 14%) and a yellow liquid. $^1$H NMR (400 MHz, CDCl3) δ 4.15-4.05 (m, 2H), 3.76-3.65 (m, 4H), 3.60-3.57 (m, 2H), 3.45 (t, 1H), 3.04-2.98 (m, 1H), 2.32-2.25 (m, 1H), 1.87-1.79 (m, 1H), 1.62 (s, 3H), 1.45 (s, 3H). MS m/z 248.2 [M+H]+.

Step 2: Preparation of (3R,5S)-3-((2-chloroethoxy)methyl)-5-(hydroxymethyl)pyrrolidin-2-one

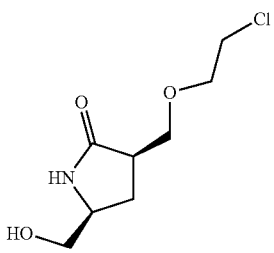 [SMILES: O=C1N[C@H](CO)C[C@@H]1COCCCl]

(6R,7aS)-6-((2-chloroethoxy)methyl)-3,3-dimethyltetrahydro-3H,5H-pyrrolo[1,2-c]oxazol-5-one (734 mg, 2.96 mmol) was dissolved in CH$_3$CN/H$_2$O (9 mL/1 mL). p-TsOH (28 mg, 0.15 mmol) was added and reaction mixture was heated to ~90° C. After 1 h the reaction mixture was cooled to ambient temperature, concentrated, and azeotroped with CH$_3$CN. The residue was purified by silica gel chromatography (5-20% MeOH/DCM) to afford the title compound (581 mg). $^1$H NMR (400 MHz, CDCl$_3$) δ 6.22 (br. s., 1H), 3.87-3.67 (m, 5H), 3.65-3.59 (m, 2H), 3.59-3.49 (m, 1H), 2.77-2.64 (m, 1H), 2.44-2.31 (m, 2H), 2.24 (t, 1H), 1.91-1.77 (m, 1H) MS m/z 207.9 [M+H]+.

Step 3: Preparation of 1-chloro-7-hydroxyisoquinoline-6-carbonitrile

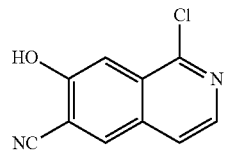 [SMILES: N#Cc1cc2ccnc(Cl)c2cc1O]

To a stirred solution of 1-chloro-7-isopropoxyisoquinoline-6-carbonitrile (2 g, 8.13 mmol) in DCM (25 mL) was added AlCl$_3$ (3.44 g, 25.8 mmol) and the mixture was headed in a 50° C. bath for 16 h. The reaction mixture was evaporated under reduced pressure and was treated with ice water to afford a solid which was filtered, washed with water and dried to afford 1-chloro-7-hydroxyisoquinoline-6-carbonitrile (1.4 g, 84% yield) as light yellow solid. $^1$H NMR (400 MHz, DMSOd-6) δ 11.95 (s, 1H), 8.65 (s, 1H), 8.22 (d, 1H), 7.85 (d, 1H), 7.68 (s, 1H). MS m/z 205.2 [M+H]+.

Step 4: Preparation of 1-chloro-7-((2-(trimethylsilyl)ethoxy)methoxy)isoquinoline-6-carbonitrile

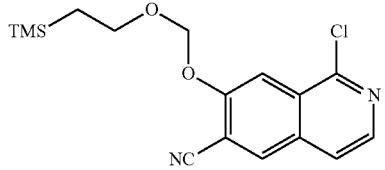 [SMILES: C[Si](C)(C)CCOCOc1cc2c(Cl)nccc2cc1C#N]

A solution of 1-chloro-7-hydroxyisoquinoline-6-carbonitrile (1 g, 4.9 mmol) in DCM (12 mL) was treated with DIEA (1.3 mL, 5.86 mmol). After 10 min, SEM chloride (0.99 mL, 5.38 mmol) was added dropwise. The reaction mixture was quenched with saturated aqueous NaHCO₃ solution then poured into NaHCO₃ and extracted twice with EtOAc. The combined organic phase was dried over MgSO₄. Chromatography on silica gel (10-30% EtOAc/heptane gradient) gave the title compound (1.20 g, % yield). ¹H NMR (400 MHz, CDCl₃) δ 8.30 (d, 1H), 8.20 (s, 1H), 8.05 (s, 1H), 7.58 (d, 1H), 5.52 (s, 2H), 3.92-3.85 (m, 2H), 1.05-0.96 (m, 2H), 0.02 (s, 9H). MS m/z 334.1 [M+H]+.

Step 5: Preparation of 1-(((2S,4R)-4-((2-chloroethoxy)methyl)-5-oxopyrrolidin-2-yl)methoxy)-7-((2-(trimethylsilyl)ethoxy)methoxy)isoquinoline-6-carbonitrile

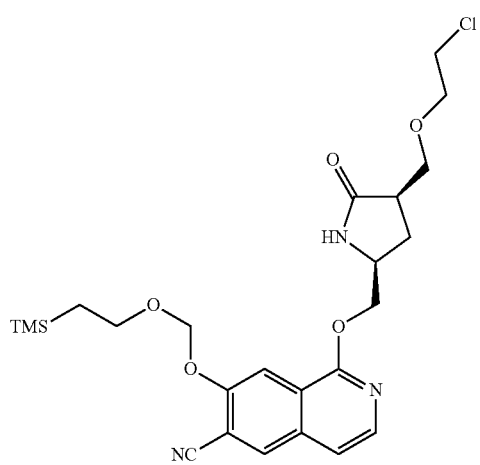 [SMILES: C[Si](C)(C)CCOCOc1cc2c(OC[C@@H]3C[C@H](COCCCl)C(=O)N3)nccc2cc1C#N]

1-Chloro-7-((2-(trimethylsilyl)ethoxy)methoxy)isoquinoline-6-carbonitrile (1.04 g, 3.09 mmol) and (3R,5S)-3-((2-chloroethoxy)methyl)-5-(hydroxymethyl)pyrrolidin-2-one (710 mg, 3.42 mmol) were dissolved in DMF (10 mL) and cooled to 0° C. KHMDS (6.81 mL, 1M toluene solution) was added dropwise. After 15 min the reaction mixture was quenched first with with water (~7 mL) then with 10% aqueous NaH₂PO₄ solution (~4 mL) and extracted twice with EtOAc. The organic phase was concentrated and the residue was purified by silica gel chromatography (50-100% EtOAc/heptane gradient) to afford a yellow solid (689 mg). ¹H NMR (400 MHz, MeOD) δ 8.29 (s, 1H), 8.01 (s, 1H), 7.96 (d, 1H), 7.34 (d, 1H), 5.60-5.49 (m, 2H), 4.63 (dd, 1H), 4.46 (dd, 1H), 4.23-4.14 (m, 1H), 3.91 (t, 2H), 3.82-3.76 (m, 1H), 3.76-3.67 (m, 3H), 3.66-3.61 (m, 2H), 2.83-2.74 (m, 1H), 2.60-2.49 (m, 1H), 2.09-1.98 (m, 1H), 0.99 (t, 2H), −0.01 (s, 9H). MS m/z 528.2 [M+Na]+.

Step 6: Preparation of 1-(((2S,4R)-4-((2-chloroethoxy)methyl)-5-oxopyrrolidin-2-yl)methoxy)-7-hydroxyisoquinoline-6-carbonitrile

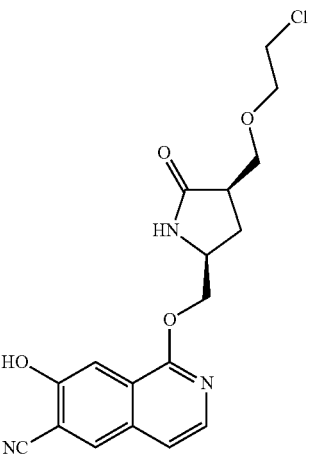 [SMILES: N#Cc1cc2ccnc(OC[C@@H]3C[C@H](COCCCl)C(=O)N3)c2cc1O]

1-(((2S,4R)-4-((2-chloroethoxy)methyl)-5-oxopyrrolidin-2-yl) methoxy)-7-((2-(trimethylsilyl)ethoxy)methoxy) isoquinoline-6-carbonitrile (480 mg, 0.95 mmol) was suspended in MeOH (7 mL) and cooled to 0° C. A solution of conc. HCl (1.5 mL) in MeOH (3 mL) was added. The reaction was warmed to ambient temperature and stirred overnight. The reaction mixture was carefully quenched with saturated aqueous NaHCO₃ solution. The mixture was partially concentrated then poured into water (20 mL) and adjusted to pH to 6-7 with 1 N HCl. This solution was extracted twice with EtOAc and dried over MgSO₄. The residue was purified by chromatography on silica gel eluting with a 0-5% MeOH/CH₂Cl₂ gradient to afford the title compound (323 mg, 91% yield) as an oil. ¹H NMR (400 MHz, CDCl₃) δ=10.03 (br. s., 1H), 8.03 (s, 1H), 7.88 (d, 1H), 7.82 (s, 1H), 7.35 (s, 1H), 7.18 (d, 1H), 4.81 (dd, 1H), 4.27-4.19 (m, 1H), 4.14 (q, 1H), 3.86 (dd, 1H), 3.75-3.65 (m, 3H), 3.61-3.48 (m, 2H), 2.86 (tt, 1H), 2.56-2.44 (m, 1H), 2.01 (td, 1H) MS m/z 373.9 [M−H]+ and 375.9 [M+H]+.

Step 7: Preparation of (3S,6R)-5-oxo-2,3,4,5,6,7,9,10-octahydro-12,14-(ethanediylidene)-3,6-methanopyrido[2,3-l][1,4,11,8]trioxazacyclopentadecine-19-carbonitrile

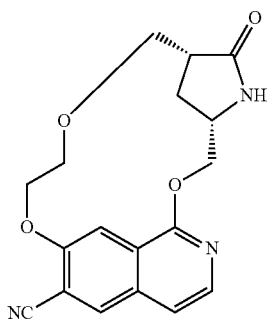 [SMILES: N#Cc1cc2ccnc3c2cc1OCCOC[C@H]1C[C@@H](CO3)NC1=O]

1-(((2S,4R)-4-((2-Chloroethoxy)methyl)-5-oxopyrrolidin-2-yl)methoxy)-7-hydroxyisoquinoline-6-carbonitrile (100 mg, 0.266 mmol) was dissolved in THF (90 mL). NaI (40.2 mg, 0.266 mmol) was added. KOtBu was added (0.56 mL, 0.56 mmol), and after a few min, DMF (10 mL) was added and the mixture was heated to 50-55° C. for 24 h. The reaction mixture was quenched with 10% aqueous NaH$_2$PO$_4$ (~4 mL), then water was added and THF was removed in vacuo. The residue was portioned with water and EtOAc and extracted with EtOAc, and the combined organic phase was dried over MgSO$_4$, filtered, and concentrated. Chromatography on silica gel eluting with 10-60% acetone/CH$_2$Cl$_2$ gradient provided an off-white solid (14.7 mg), which was purified on silica gel eluting with a 0 to 10% EtOAc/MeOH gradient to afford the title compound (5.9 mg, 6.5% yield). $^1$H NMR (400 MHz, DMSO-d6) δ=11.45 (br. s., 1H), 8.71 (s, 1H), 8.43 (s, 1H), 7.97 (d, 1H), 7.65 (s, 1H), 7.39 (d, 1H), 4.84 (d, 1H), 4.71-4.62 (m, 1H), 4.53-4.45 (m, 1H), 4.23 (d, 1H), 3.91 (t, 1H), 3.81 (d, 2H), 3.77 (d, 1H), 3.49 (d, 1H), 2.69-2.57 (m, 1H), 2.19-2.08 (m, 1H). MS m/z 340.2 [M+H]+.

Step 8: Preparation of (3S,6R)-5-oxo-2,3,4,5,6,7,9,10-octahydro-12,14-(ethanediylidene)-3,6-methanopyrido[2,3-l][1,4, 11,8]trioxazacyclopentadecine-19-carboxamide To a solution of (3S,6R)-5-oxo-2,3,4,5,6,7,9,10-octahydro-12,14-(ethanediylidene)-3,6-methanopyrido[2,3-l][1, 4,11,8]trioxazacyclopentadecine-19-carbonitrile (5.9 mg, 0.017 mmol) in DMSO-d6 (1.0 mL) was added K$_2$CO$_3$ (9.6 mg, 0.068 mmol). The suspension was stirred for ~5 min then hydrogen peroxide was added (0.01 mL). An additional 2 drops of H$_2$O$_2$ solution (~0.03 mL) and K$_2$CO$_3$ (~15 mg) added. After 1.5 h, an additional drop of H$_2$O$_2$ solution (0.015 mL) was added. After 1 h, the reaction mixture was quenched with Me$_2$S and stirred for about 15 min. The reaction mixture was filtered and purified by HPLC to give the title compound (1.8 mg, 30% yield). HPLC conditions: The residue was dissolved in DMSO (1 mL) and purified by reversed-phase HPLC Column: Waters XBridge C18 19×100, 5μ; Mobile phase A: 0.03% NH$_4$OH in water (v/v); Mobile phase B: 0.03% NH$_4$OH in acetonitrile (v/v); Gradient: 95.0% H$_2$O/5.0% Acetonitrile linear to 60.0% H$_2$O/40.0% Acetonitrile in 10.5 min, 60.0% H$_2$O/40.0% Acetonitrile linear to 0% H$_2$O/100% Acetonitrile in 0.5 min HOLD at 0% H$_2$O/100% Acetonitrile from 11.0 to 12.0 min. Flow: 25 mL/min. Analytical QC Column: Waters Atlantis dC18 4.6×50, 5μ; Mobile phase A: 0.05% TFA in water (v/v); Mobile phase B: 0.05% TFA in acetonitrile (v/v); Gradient: 95.0% H$_2$O/5.0% Acetonitrile linear to 5% H$_2$O/95% Acetonitrile in 4.0 min, HOLD at 5% H$_2$O/95% Acetonitrile to 5.0 min. Flow: 2 mL/min. Retention time, 1.75 min. $^1$H NMR (600 MHz, DMSO-d6) δ 8.66 (s, 1H), 8.13 (s, 1H), 7.86 (d, 1H), 7.84 (br. s., 1H), 7.66 (s, 1H), 7.61 (br. s., 1H), 7.38 (d, 1H), 7.10-7.04 (m, 1H), 4.78 (d, 1H), 4.59 (dd, 1H), 4.43 (dd, 1H), 4.20 (d, 1H), 3.92 (t, 1H), 3.85-3.75 (m, 2H), 3.59-3.52 (m, 1H), 3.49 (dd, 1H), 3.43 (1H obscured by water), 2.66-2.60 (m, 1H), 2.57-2.51 (m, 1H), 2.18-2.09 (m, 1H). MS m/z 358.1 [M+H]+.

Example 29

7-methoxy-1-[(3-oxo-2-azabicyclo[3.1.0]hex-1-yl)methoxy]isoquinoline-6-carboxamide

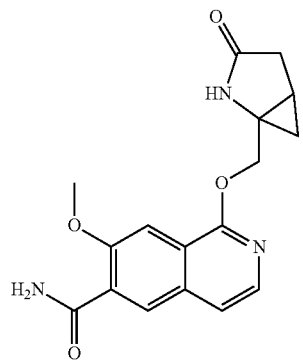

Step 1: Preparation of N-(4-methoxybenzyl)but-3-en-1-amine

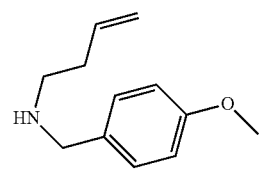

To a solution of but-3-en-1-amine (1.89 mL, 20 mmol) in EtOH (40 mL) was added 4-methoxybenzaldehyde (2.48 mL, 20 mmol). After 15 min, NaBH$_3$CN (1.55 g, 24 mmol) was added in one portion. After 2 h, another portion of NaBH$_3$CN (1.55 g, 24 mmol) was added and stirring continued for 4 h. Oven-dried powdered 4 Å molecular sieves (3 g) were then added and the mixture was stirred overnight. The mixture was filtered through Celite® and the cake was rinsed with MeOH. The solvent was evaporated under reduced pressure and the resulting crude yellow oil was purified using silica gel column chromatography eluting with 10% MeOH in DCM to afford the title compound as a pale yellow oil (2.69 g, 70% yield). $^1$H NMR (CDCl$_3$, 400 MHz): δ 7.38 (d, 2H), 6.93 (d, 2H), 5.71 (ddt, 1H), 5.21 (dd, 1H), 5.18-5.16 (m, 1H), 4.05 (s, 2H), 3.79 (s, 3H), 2.92 (t, 2H), 2.51-2.46 (m, 2H). MS m/z 192 [M+H]$^+$

Step 2: Preparation of Methyl [but-3-en-1-yl(4-methoxybenzyl)amino](oxo)acetate

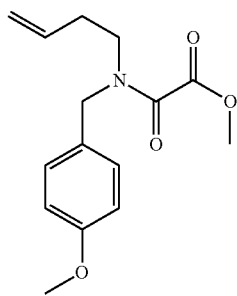 [SMILES: C=CCCN(Cc1ccc(OC)cc1)C(=O)C(=O)OC]

N-(4-Methoxybenzyl)but-3-en-1-amine (6.87 g, 35.92 mmol) was dissolved in DCM (40 mL) and aqueous saturated NaHCO₃ (120 mL) was added. Under vigorous stirring, methyl chloro(oxo)acetate (13.20 g, 108 mmol) was added dropwise over 5 min. The mixture was stirred for 2 h. The aqueous layer was extracted with DCM and combined organic extracts were dried over Na₂SO₄. The compound was obtained as a pale yellow oil (7.18 g, 72% yield) as mixture of two rotamers in a 1:1 ratio, and was used without purification. ¹H NMR (CDCl₃, 400 MHz): δ 7.23 (d, 1H), 7.21 (d, 1H), 6.90 (d, 1H), 6.88 (d, 1H), 5.79-5.71 (m, 0.5H), 5.71-5.62 (m, 0.5H), 5.10-5.06 (m, 1H), 5.05-5.01 (m, 1H), 4.58 (s, 1H), 4.39 (s, 1H), 3.89 (s, 1.5H), 3.87 (s, 1.5H), 3.82 (s, 1.5H), 3.81 (s, 1.5H), 3.35 (dd, 1H), 3.25-3.21 (m, 1H), 2.35-2.30 (m, 1H), 2.30-2.25 (m, 1H). MS m/z 278 [M+H]⁺

Step 3: Preparation of N-(but-3-en-1-yl)-2-hydroxy-N-(4-methoxybenzyl)acetamide

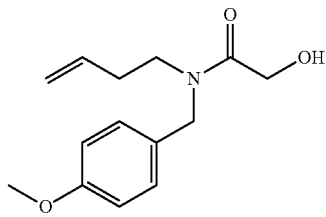 [SMILES: C=CCCN(Cc1ccc(OC)cc1)C(=O)CO]

To a solution of methyl [but-3-en-1-yl(4-methoxybenzyl)amino](oxo)acetate (4.25 g, 15.3 mmol) in MeOH (61.3 mL) was added sodium borohydride (3.00 g, 79.2 mmol) in portions. The reaction was exothermic. After addition was complete, the reaction mixture was stirred until it returned to room temperature. MeOH was removed under reduced pressure and the resulting slurry was partitioned in DCM/saturated aqueous NH₄Cl solution (40 mL, 1:1 v/v). Water was then added. The aqueous layer was extracted with DCM and the combined organic extracts were dried over Na₂SO₄, filtered and evaporated to dryness to afford the title compound as a colorless oil (3.70 g, ~97% yield) as a mixture of two rotamers in a 1:1 ratio. This material was used without further purification. ¹H NMR (CDCl₃, 400 MHz): δ 7.20 (d, 1H), 7.08 (d, 1H), 6.90 (d, 1H), 6.87 (d, 1H), 5.82-5.73 (m, 0.5H), 5.72-5.63 (m, 0.5H), 5.10 (d, 1H), 5.07-5.02 (m, 1H), 4.62 (s, 1H), 4.29 (s, 1H), 4.22 (d, 1H), 4.21 (d, 1H), 3.82 (s, 1.5H), 3.81 (s, 1.5H), 3.68 (t, 0.5H), 3.65 (t, 0.5H), 3.51-3.45 (m, 1H), 3.13-3.08 (m, 1H), 2.35-2.30 (m, 1H), 2.29-2.24 (m, 1H). MS m/z 250 [M+H]⁺

Step 4: Preparation of N-(but-3-en-1-yl)-2-{[tert-butyl(dimethyl)silyl]oxy}-N-(4-methoxybenzyl)acetamide

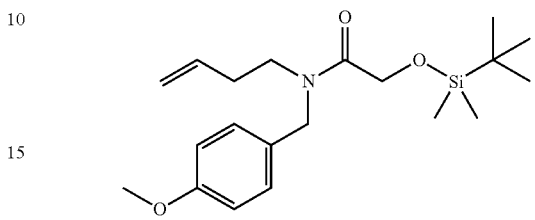

To a solution of N-(but-3-en-1-yl)-2-hydroxy-N-(4-methoxybenzyl)acetamide (6.00 g, 24.1 mmol) in DCM (96.3 mL) was added imidazole (2.47 g, 36.10 mmol) followed by TBDMSCl (4.49 g, 28.9 mmol) and the reaction mixture was stirred overnight. Water was added and the aqueous phase was extracted with DCM. The combined organic extracts were washed with water, dried over Na₂SO₄ and concentrated under reduced pressure. The residue was dissolved in MeOH and concentrated. The crude oil was purified using silica gel column chromatography eluting with heptane/EtOAc to afford the title compound as a colorless oil (7.72 g, 88% yield) as a mixture of two rotamers in a 1:1 ratio. ¹H NMR (CDCl₃, 400 MHz): δ 7.19 (d, 1H), 7.12 (d, 1H), 6.88 (d, 1H), 6.85 (d, 1H), 5.80-5.74 (m, 0.5H), 5.74-5.67 (m, 0.5H), 5.06 (d, 1H), 5.04-4.98 (m, 1H), 4.56 (s, 1H), 4.52 (s, 1H), 4.37 (s, 1H), 4.34 (s, 1H), 3.82 (s, 1.5H), 3.81 (s, 1.5H), 3.38 (t, 1H), 3.29 (t, 1H), 2.33-2.29 (m, 1H), 2.29-2.26 (m, 1H), 0.93 (s, 4.5H), 0.89 (s, 4.5H), 0.14 (s, 3H), 0.09 (s, 3H).

Step 5: Preparation of 1-({[tert-butyl(dimethyl)silyl]oxy}methyl)-2-(4-methoxybenzyl)-2-azabicyclo[3.1.0]hexane

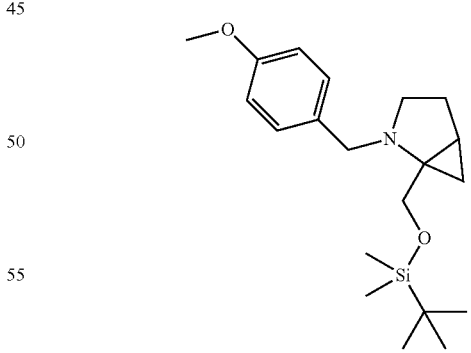

A dried flask was charged with N-(but-3-en-1-yl)-2-{[tert-butyl(dimethyl)silyl]oxy}-N-(4-methoxybenzyl)acetamide (4.00 g, 11.0 mmol) and placed under inert atmosphere. Dry THF (110 mL) was added and to the well-stirred solution was added titanium isopropoxide (4.69 g, 16.5 mmol), followed by dropwise addition over 60 min with syringe pump of cyclopentylmagnesium bromide (22.0 mL, 2.0 M in diethyl ether, 44.0 mmol). After 2 h, the reaction was quenched with a cold Rochelle's salt solution and extracted with EtOAc. The combined organic extracts were washed with water and brine, and dried over Na$_2$SO$_4$. After filtration, the volatiles were removed under reduced pressure to yield the crude product. The crude oil was purified using silica gel column chromatography eluting with heptane/EtOAc to afford the title compound as a colorless oil (2.00 g, 52% yield). $^1$H NMR (CDCl$_3$, 400 MHz): δ 7.27 (d, 2H), 6.84 (d, 2H), 4.18 (d, 1H), 4.05 (d, 1H), 3.80 (s, 3H), 3.69 (d, 1H), 3.18 (d, 1H), 2.89-2.81 (m, 1H), 1.97-1.84 (m, 2H), 1.77-1.68 (m, 1H), 1.29 (td, 1H), 0.89 (s, 9H), 0.85 (t, 1H), 0.49 (dd, 1H), 0.06 (s, 6H). MS m/z 348 [M+H]$^+$ Step 6: Preparation of 2-azabicyclo[3.1.0]hex-1-ylmethanol hydrochloride

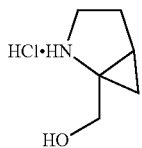

At 0° C. under inert atmosphere, to a solution of 1-({[tert-butyl(dimethyl)silyl]oxy}methyl)-2-(4-methoxybenzyl)-2-azabicyclo[3.1.0]hexane (2.00 g, 5.75 mmol) in 1,2-dichloroethane (19.2 mL) was added ACE-Cl (1.08 g, 7.48 mmol) and the mixture was stirred at 0° C. for 30 min. Volatiles were removed under reduced pressure and the resulting crude material was solubilized in MeOH (29 mL). The mixture was heated at 50° C. for 2 h and volatiles were evaporated under reduced pressure. The resulting brown gum was triturated with DCM/heptane (3:1) and the supernatant was discarded. This operation was repeated 5 times, and the title product was obtained as a pale brown solid (860 mg, 99% yield) and was used without further purification. $^1$H NMR (DMSO-d6, 400 MHz): δ 9.45 (br. s., 1H), 9.23 (br. s., 1H), 5.33 (br. s., 1H), 3.83-3.76 (m, 1H), 3.65 (d, 1H), 3.30-3.24 (m, 1H), 2.94-2.81 (m, 1H), 2.08-1.91 (m, 2H), 1.65 (td, 1H), 1.10-1.05 (m, 1H), 0.87-0.80 (m, 1H).

Step 7: Preparation of tert-butyl 1-({[tert-butyl(dimethyl)silyl]oxy}methyl)-2-azabicyclo[3.1.0]hexane-2-carboxylate

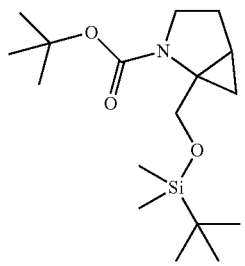 [SMILES: CC(C)(C)OC(=O)N1CCC2CC21CO[Si](C)(C)C(C)(C)C]

To a solution of crude 2-azabicyclo[3.1.0]hex-1-ylmethanol hydrochloride (860 mg, 5.75 mmol) in DCM (28.7 mL) was added TEA (640 mg, 6.32 mmol) followed by N,N-dimethylpyridin-4-amine (353 mg, 2.87 mmol) and BOC$_2$O (1.42 g, 6.32 mmol). The mixture was stirred for 24 h, and then imidazole (472 mg, 6.90 mmol) was added, followed by TBDMSCl (983 mg, 6.32 mmol). The mixture was stirred at room temperature overnight. The reaction was quenched with saturated aqueous NH$_4$Cl and extracted with DCM. The combined organic extracts were dried over Na$_2$SO$_4$. After filtration, the volatiles were removed under reduced pressure to yield the crude product. The residue was purified using silica gel column chromatography eluting with heptane/EtOAc to afford the title compound as a pale yellow oil (1.52 g, 81% yield). $^1$H NMR (CDCl$_3$, 400 MHz): δ 4.32 (br. s., 1H), 3.71-3.60 (m, 2H), 3.45 (br. s., 1H), 2.16-2.05 (m, 1H), 1.82-1.73 (m, 1H), 1.65-1.57 (m, 1H), 1.47 (s, 9H), 1.05 (dd, 1H), 0.88 (s, 9H), 0.64 (t, 1H), 0.04 (s, 6H).

Step 8: Preparation of tert-Butyl 1-({[tert-butyl(dimethyl)silyl]oxy}methyl)-3-oxo-2-azabicyclo[3.1.0]hexane-2-carboxylate

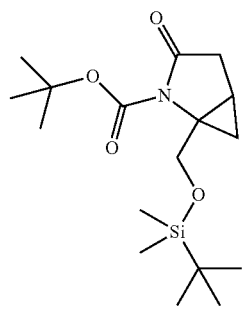 [SMILES: CC(C)(C)OC(=O)N1C(=O)CC2CC21CO[Si](C)(C)C(C)(C)C]

Sodium metaperiodate (989 mg, 4.58 mmol) was dissolved in water (25 mL) under N$_2$, and ruthenium dioxide hydrate (70 mg, 0.46 mmol) was added. After 5 min, tert-butyl 1-({[tert-butyl(dimethyl)silyl]oxy}methyl)-2-azabicyclo[3.1.0]hexane-2-carboxylate (500 mg, 1.53 mmol) was added as a solution in EtOAc (25 mL), and the resulting biphasic solution was stirred vigorously for 5 h. The reaction mixture was extracted with EtOAc. The combined organic layers were washed with NaHSO$_3$ several times until a clear, colorless organic layer was obtained. The organic layer was further washed with brine and dried over Na$_2$SO$_4$. The residue was purified using silica gel column chromatography eluting with heptane/EtOAc to afford the title compound as a colorless oil (260 mg, 50% yield). $^1$H NMR (CDCl$_3$, 400 MHz): δ 4.40 (d, 1H), 3.58 (d, 1H), 2.89 (dd, 1H), 2.49 (d, 1H), 1.55 (s, 9H), 1.53-1.45 (m, 1H), 1.10 (dd, 1H), 0.88 (s, 9H), 0.66 (t, 1H), 0.05 (s, 6H). MS m/z 242 [M-Boc+H]$^+$ (Boc-deprotection under LCMS conditions).

Step 9: Preparation of tert-butyl (3-oxo-2-azabicyclo[3.1.0]hex-1-yl)methyl carbonate

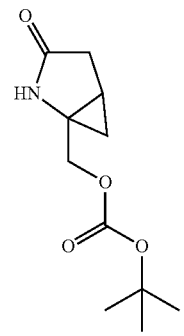

To a solution tert-butyl 1-({[tert-butyl(dimethyl)silyl]oxy}methyl)-3-oxo-2-azabicyclo[3.1.0]hexane-2-carboxylate (155 mg, 0.45 mmol) in THF (0.76 mL) at room temperature was added TBAF (0.73 mL, 1.0 M in THF, 0.73 mmol) and the mixture was stirred for 30 min, then diluted with EtOAc and water. The aqueous layer was extracted with EtOAc and the combined organic layers were dried over Na$_2$SO$_4$ and concentrated to afford the title compound as a pale yellow oil (103 mg, 99%) which was used without further purification. $^1$H NMR (CDCl$_3$, 400 MHz): δ 6.03 (br. s., 1H), 4.34 (d, 1H), 4.14 (d, 1H), 2.77 (dd, 1H), 2.35 (d, 1H), 1.67-1.57 (m, 1H), 1.51 (s, 9H), 1.14 (dd, 1H), 0.72 (t, 1H). MS m/z 228 [M+H]$^+$

Step 10: Preparation of 7-methoxy-1-[(3-oxo-2-azabicyclo[3.1.0]hex-1-yl)methoxy]isoquinoline-6-carbonitrile

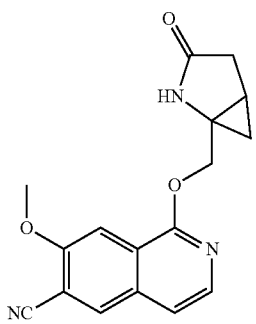 [SMILES: COc1cc2c(OCC34CC3CC(=O)N4)nccc2cc1C#N]

To a solution of tert-butyl (3-oxo-2-azabicyclo[3.1.0]hex-1-yl)methyl carbonate (103 mg, 0.453 mmol) in DMF (3.5 mL) was added KHMDS (1.36 mL, 1.0 M in THF, 1.36 mmol) and the mixture was stirred at −10° C. for 15 min. Then a solution of 1-chloro-7-methoxyisoquinoline-6-carbonitrile (104 mg, 0.48 mmol) in DMF (1.0 mL) and the mixture was stirred at −10° C. for 2 h. It was then quenched with saturated aqueous NH$_4$Cl and diluted with DCM. The aqueous layer was extracted with DCM and the combined organic layers were washed with brine and dried over Na$_2$SO$_4$. The crude material was purified using silica gel column chromatography eluting with DCM/EtOAc to afford the title compound as a yellow solid (50 mg, 36% yield). $^1$H NMR (CDCl3, 400 MHz): δ 8.08 (s, 1H), 7.95 (d, 1H), 7.58 (s, 1H), 7.23 (d, 1H), 6.60 (br. s., 1H), 4.93 (d, 1H), 4.58 (d, 1H), 4.08 (s, 3H), 2.82 (dd, 1H), 2.41 (d, 1H), 1.79-1.72 (m, 1H), 0.89 (t, 1H), 0.74 (t, 1H). MS m/z 310 [M+H]$^+$

Step 11: Preparation of 7-methoxy-1-[(3-oxo-2-azabicyclo[3.1.0]hex-1-yl)methoxy]isoquinoline-6-carboxamide

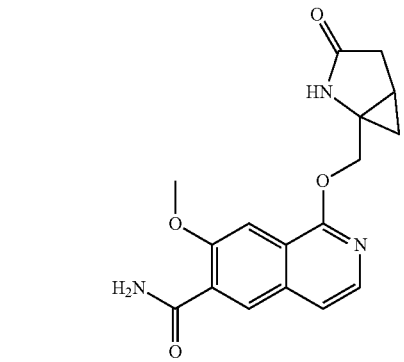 [SMILES: COc1cc2c(OCC34CC3CC(=O)N4)nccc2cc1C(N)=O]

A solution of 7-methoxy-1-[(3-oxo-2-azabicyclo[3.1.0]hex-1-yl)methoxy]isoquinoline-6-carbonitrile (50 mg, 0.16 mmol) in DMSO (1.6 mL) was treated with K$_2$CO$_3$ (112 mg, 0.81 mmol). The resulting mixture was stirred for 5 min, after which time hydrogen peroxide (0.064 mL, 50% w/w in water, 1.13 mmol) was added to the reaction mixture. Stirring was continued for 5 h. The reaction mixture was quenched with Me$_2$S (80.3 mg, 1.29 mmol) and stirred at room temperature for 30 min before the reaction was filtered through Celite®. The cake was washed with DCM and EtOAc and the filtrate was concentrated under reduced pressure to give a DMSO solution which was dried at 45° C. overnight with a stream of nitrogen. The crude material was purified using silica gel column chromatography eluting with DCM/MeOH to afford the title compound as a pale yellow solid (33 mg, 62% yield). $^1$H NMR (CDCl$_3$—with one drop of CD$_3$OD—400 MHz): δ 8.42 (s, 1H), 7.76 (d, 1H), 7.56 (br. s., 1H), 7.18 (d, 1H), 4.70 (d, 1H), 4.55-4.46 (m, 1H), 4.03-3.98 (m, 3H), 2.68 (dd, 1H), 2.27 (d, 1H), 1.65 (br. s., 1H), 1.22-1.10 (m, 1H), 0.67-0.59 (m, 1H). MS m/z 328 [M+H]$^+$ This racemic material (29 mg) was separated by chiral chromatography leading to two enantiomers.

Enantiomer 1: pale yellow solid, 12 mg (100% ee), MS m/z 350.1 [M+Na]$^+$. Enantiomer 2: pale yellow solid, 13 mg (99.5% ee). MS m/z, 328.1 [M+H]$^+$. 1H NMR (400 MHz, DMSO-d6) d=8.58 (s, 1H), 8.17 (s, 1H), 7.89 (d, 1H), 7.84 (br. s., 1H), 7.69 (br. s, 2H), 7.42 (d, 1H), 4.70 (d, 1H), 4.58 (d, 1H), 4.00 (s, 3H), 2.70-2.62 (m, 1H), 1.74-1.65 (m, 1H), 1.17 (dd 1H), 0.61 (t, 1H) one proton obscured, presumably overlapping with water.

Example 30 (Enantiomer 1)

7-methoxy-1-{[(1S,5S)-3-oxo-2-azabicyclo[3.1.0]hex-1-yl]methoxy}isoquinoline-6-carboxamide

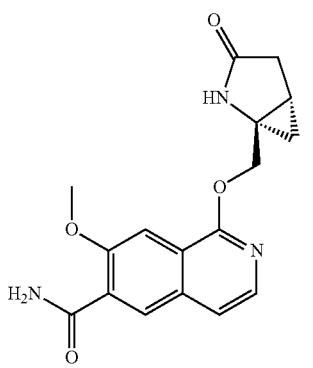 [SMILES: COc1cc2c(OC[C@]34C[C@H]3CC(=O)N4)nccc2cc1C(N)=O]

Obtained as pale yellow solid (12 mg). $^1$H NMR (CDCl$_3$—with one drop of CD$_3$OD—400 MHz): δ 8.41 (s, 1H), 7.77 (d, 1H), 7.56 (br. s., 1H), 7.18 (d, 1H), 4.71 (d, 1H), 4.57-4.47 (m, 1H), 4.05-3.99 (m, 3H), 2.68 (dd, 1H), 2.26 (d, 1H), 1.63 (br. s., 1H), 1.22-1.11 (m, 1H), 0.66-0.58 (m, 1H). MS m/z 350 [M+Na]$^+$.

Example 31 (Enantiomer 2)

7-methoxy-1-{[(1R,5R)-3-oxo-2-azabicyclo[3.1.0]hex-1-yl]methoxy}isoquinoline-6-carboxamide

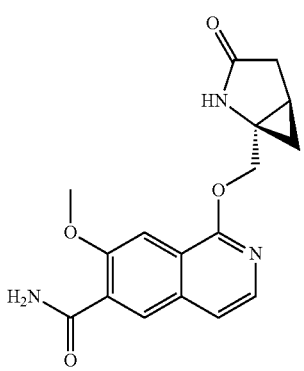 [SMILES: COc1cc2c(OC[C@@]34C[C@@H]3CC(=O)N4)nccc2cc1C(N)=O]

Obtained as pale yellow solid (13 mg). $^1$H NMR (CDCl$_3$—with one drop of CD$_3$OD—400 MHz): δ 8.39 (s, 1H), 7.76 (d, 1H), 7.54 (br. s., 1H), 7.17 (d, 1H), 4.73 (d, 1H), 4.56-4.47 (m, 1H), 4.03-3.97 (m, 3H), 2.69 (dd, 1H), 2.26 (d, 1H), 1.64 (br. s., 1H), 1.23-1.11 (m, 1H), 0.66-0.59 (m, 1H). MS m/z 328 [M+H]$^+$.

Example 32

5-{[(2S,3S,4S)-3-ethyl-4-fluoro-5-oxopyrrolidin-2-yl]methoxy}-3-methoxy-1,6-naphthyridine-2-carboxamide

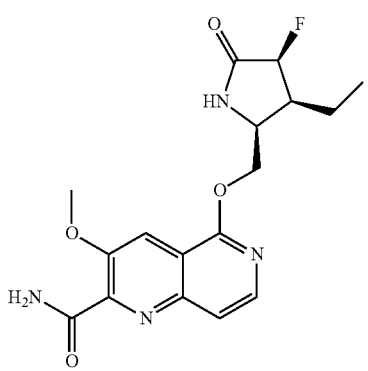 [SMILES: CC[C@@H]1[C@H](F)C(=O)N[C@@H]1COc1nccc2nc(C(N)=O)c(OC)cc12]

Step 1: Preparation of 1-(aminooxy)-2,2-dimethylpropan-1-one triflate

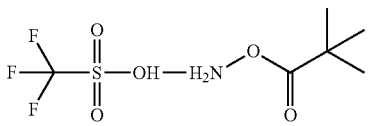 [SMILES: CC(C)(C)C(=O)ONOS(=O)(=O)C(F)(F)F]

In air, tert-butyl hydroxycarbamate (10.68 g, 80.21 mmol) was weighed in a reaction flask equipped with a stir bar. CHCl$_3$ (201 mL) and 2,2-dimethylpropanoic anhydride (17.9 g, 96.3 mmol) were successively added, then the tube was sealed. The reaction was stirred at 80° C. for 16 h. The reaction mixture was poured into saturated aqueous NaHCO$_3$ solution, and the organic layer was separated, washed with saturated aqueous NaHCO$_3$, dried over MgSO$_4$ and evaporated to afford a white solid. This solid was charged in a round bottom flask equipped with a stir bar. Diethyl ether (201 mL) was added and the flask was closed with a septum and cooled to 0° C. Triflic acid (12.00 g, 80.2 mmol) was added in one portion and the reaction was stirred at room temperature for 1 h. The reaction mixture was diluted with heptane (400 mL): a precipitate formed and was collected by filtration on a fritted funnel to afford the title compound as a white solid (11.9 g, 55% yield). $^1$H NMR (DMSO-d6, 400 MHz): δ 9.44-8.84 (m, 3H), 1.21 (s, 9H). $^{19}$F NMR (DMSO-d6, 376 MHz): δ −77.0.

Step 2: Preparation of N-[(2,2-dimethylpropanoyl)oxy]-5-methoxypyridine-3-carboxamide

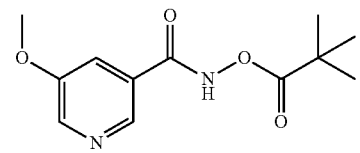 [SMILES: COc1cncc(C(=O)NOC(=O)C(C)(C)C)c1]

To a solution of 5-methoxypyridine-3-carboxylic acid (5.00 g, 32.6 mmol) in DCM (54.4 mL) and DMF (1.1 mL) was added at room temperature under inert atmosphere oxalyl chloride (4.35 g, 34.3 mmol). After 3 h, a solution of 1-(aminooxy)-2,2-dimethylpropan-1-one triflate (8.90 g, 33.3 mmol) in DCM (27.2 mL) and pyridine (5.68 g, 71.8 mmol) (prepared under nitrogen with sonication) was added via syringe and the resulting mixture was stirred at room temperature for 3 h. The reaction was then quenched with a saturated aqueous NH$_4$Cl solution, and the aqueous layer was extracted with DCM. The combined organic extracts were dried over Na$_2$SO$_4$. The residue was purified using silica gel column chromatography eluting with DCM/EtOAc to afford the title compound as a white solid (5.3 g, 64% yield). $^1$H NMR (DMSO-d6, 400 MHz): δ 12.49 (s, 1H), 8.57 (s, 1H), 8.49 (s, 1H), 7.70 (br. s., 1H), 3.89 (s, 3H), 1.29 (s, 9H). MS m/z 253 [M+H]$^+$.

Step 3: Preparation of N-[(2,2-dimethylpropanoyl)oxy]-5-methoxypyridine-3-carboxamide 1-oxide

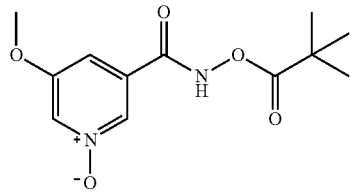 [SMILES: COc1cc(C(=O)NOC(=O)C(C)(C)C)c[n+]([O-])c1]

A flask containing N-[(2,2-dimethylpropanoyl)oxy]-5-methoxypyridine-3-carboxamide (3.30 g, 13.1 mmol) was charged with methyl(trioxo)rhenium (32.6 mg, 0.131 mmol) followed by DCM (17.4 mL). 30% aq H$_2$O$_2$ (2.94 mL, 28.8 mmol) was added to the reaction mixture which was stirred at room temperature for 5 h. Aqueous sodium thiosulfate (4 mL) was added and the mixture was stirred at room temperature for 15 min. The reaction mixture was diluted with DCM (30 mL). The organic layer was dried over MgSO$_4$, filtered and concentrated under reduced pressure providing a thick oil. The oil was dissolved in iPrOH (20 mL) and concentrated under reduced pressure providing the title compound as a white solid (3.33 g, 95% yield). $^1$H NMR (DMSO-d6, 400 MHz): δ 12.63 (s, 1H), 8.27 (s, 1H), 8.18 (s, 1H), 7.33 (s, 1H), 3.88 (s, 3H), 1.28 (s, 9H). MS m/z 269.0 [M+H]$^+$ Step 4: Preparation of 3-methoxy-6a,7,10,10a-tetrahydro-7,10-methanobenzo[h][1,6]naphthyridin-5(6H)-one 1-oxide

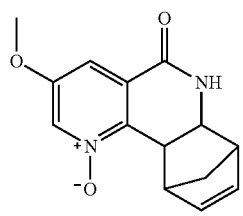 [SMILES: COc1cc2c([n+]([O-])c1)C1C3C=CC(C3)C1NC2=O]

A vial was charged with N-[(2,2-dimethylpropanoyl)oxy]-5-methoxypyridine-3-carboxamide 1-oxide (530 mg, 1.98 mmol), NaOAc (81.0 mg, 0.99 mmol) and bis(pentamethylcyclopentadienyl)dichlororhodium (30.5 mg, 0.049 mmol). MeOH (10 mL) was added followed by bicyclo[2.2.1]hepta-2,5-diene (273 mg, 3.0 mmol). The vial was sealed and stirred at 50° C. for 2 h. The mixture was cooled to room temperature and filtered. The white solid was washed with cold MeOH and thoroughly dried under reduced pressure. Once dried, the title compound was obtained as a white solid (435 mg, 85% yield) and was used without further purification. $^1$H NMR (DMSO-d6, 400 MHz): δ 8.52 (br. s., 1H), 8.32 (s, 1H), 7.41 (s, 1H), 6.45-6.41 (m, 1H), 6.19-6.16 (m, 1H), 3.86 (s, 3H), 3.61 (d, 1H), 3.22 (br. s., 1H), 3.07 (d, 1H), 2.92 (br. s., 1H), 1.38-1.33 (m, 1H), 1.29-1.24 (m, 1H). MS m/z 259 [M+H]$^+$ Step 5: Preparation of 3-methoxy-1,6-naphthyridin-5(6H)-one 1-oxide

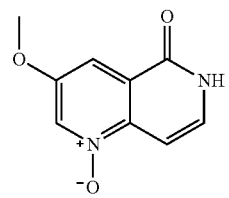

A suspension of 3-methoxy-6a,7,10,10a-tetrahydro-7,10-methanobenzo[h][1,6]naphthyridin-5(6H)-one 1-oxide (44.0 mg, 0.17 mmol) in toluene (0.6 mL) and MeOH (0.6 mL) was heated in a sealed flask at 130° C. for 1 h under microwave irradiation. The cap was removed and the reaction was monitored by LCMS. This operation was repeated five times, at which time LCMS showed complete consumption of the starting material. The resulting solution was concentrated under reduced pressure, thus providing the title compound as a pale yellow solid (33 mg, 99% yield). $^1$H NMR (DMSO-d6, 400 MHz): δ 11.78 (br. s., 1H), 8.51 (s, 1H), 7.52 (s, 1H), 7.34 (t, 1H), 6.99 (d, 1H), 3.91 (s, 3H). MS m/z 193 [M+H]$^+$ Step 6: Preparation of 3-methoxy-5-oxo-5,6-dihydro-1,6-naphthyridine-2-carbonitrile

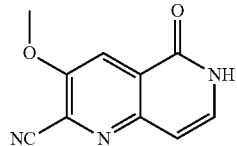

To a solution of 3-methoxy-1,6-naphthyridin-5(6H)-one 1-oxide (150 mg, 0.776 mmol) in DCM (2.59 mL) was added dimethylcarbamic chloride (125 mg, 1.16 mmol) followed by TMSCN (154 mg, 1.55 mmol). DMF (0.2 mL) was added and the mixture was stirred at 50° C. for 5 h. Volatiles were removed under reduced pressure and the residue was purified using silica gel column chromatography eluting with DCM/MeOH to afford the title compound as a yellow solid (118 mg, 76% yield). $^1$H NMR (DMSO-d6, 400 MHz): δ 11.73 (br. s., 1H), 8.21 (s, 1H), 7.41 (t, 1H), 6.63 (d, 1H), 4.08 (s, 3H). MS m/z 202 [M+H]$^+$

Step 7: Preparation of 5-chloro-3-methoxy-1,6-naphthyridine-2-carbonitrile

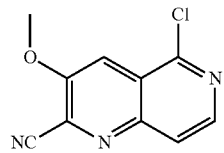

A dried vial was charged with 3-methoxy-5-oxo-5,6-dihydro-1,6-naphthyridine-2-carbonitrile (150 mg, 0.746 mmol), pyridinium hydrochloride (86 mg, 0.746 mmol) and phosphoryl chloride (2.76 mL). The reaction was heated at 90° C. for 1 h and then was cooled to room temperature. The solution was carefully poured into a beaker containing a stirred mixture of an aqueous Na$_2$HPO$_4$ solution and ice. The precipitate was filtered, washed with water and dried under vacuum. The title compound was obtained as a beige solid (111 mg, 68% yield) and was used without further purification. $^1$H NMR (DMSO-d6, 400 MHz): δ 8.53 (d, 1H), 8.15 (s, 1H), 8.01 (d, 1H), 4.18 (s, 3H). MS m/z 220 [M+H]$^+$

Step 8: Preparation of 5-chloro-3-methoxy-1,6-naphthyridine-2-carboxamide

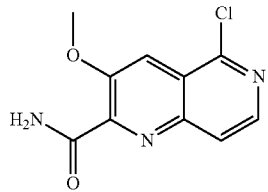 [SMILES: COc1cc2c(Cl)nccc2nc1C(N)=O]

A solution of 5-chloro-3-methoxy-1,6-naphthyridine-2-carbonitrile (149 mg, 0.678 mmol) in DMSO (6.78 mL) was treated with K$_2$CO$_3$ (469 mg, 3.39 mmol). The resulting mixture was stirred for 5 min, after which time an aqueous solution of 50% hydrogen peroxide (269 uL, 4.75 mmol) was added. After 5 min, the reaction mixture was quenched with dimethyl disulfide (337 mg, 5.43 mmol) and stirred at room temperature for 30 min before the reaction was filtered through celite. The cake was washed with DCM, then EtOAc, and the filtrate was concentrated under reduced pressure to give a DMSO solution which was dried at 45° C. overnight with a stream of nitrogen. The crude material was purified using silica gel column chromatography eluting with DCM/MeOH to afford the title compound as pale yellow solid (62 mg, 38% yield). $^1$H NMR (DMSO-d6, 400 MHz): δ 8.45 (d, 1H), 8.10 (br. s., 1H), 7.93 (d, 1H), 7.90 (s, 1H), 7.84 (br. s., 1H), 4.04 (s, 3H). MS m/z 238 [M+H]$^+$

Step 9: Preparation of 5-{[(2S,3S,4S)-3-ethyl-4-fluoro-5-oxopyrrolidin-2-yl]methoxy}-3-methoxy-1,6-naphthyridine-2-carboxamide To a solution of (3S,4S,5S)-4-ethyl-3-fluoro-5-(hydroxymethyl)pyrrolidin-2-one (38 mg, 0.236 mmol) and 5-chloro-3-methoxy-1,6-naphthyridine-2-carboxamide (59 mg, 0.25 mmol) in DMF (1.24 mL) was added KHMDS (0.95 mL, 1.0 M in THF, 0.95 mmol) at room temperature. The mixture was heated at 50° C. and stirred for 2 h. The reaction was then cooled and quenched with saturated aqueous NH$_4$Cl solution and diluted with DCM. The aqueous layer was extracted with DCM and combined organic layers were washed with brine and dried over Na$_2$SO$_4$. The crude material was purified using silica gel column chromatography eluting with DCM/MeOH to afford the title compound as an off-white solid (24 mg, 27% yield). $^1$H NMR (DMSO-d6, 500 MHz): δ 8.93 (s, 1H), 8.11 (d, 1H), 8.06 (s, 1H), 8.02 (br. s., 1H), 7.73 (br. s., 1H), 7.44 (dd, 1H), 4.97-4.83 (m, 1H), 4.61 (dd, 1H), 4.23 (dd, 1H), 4.14-4.07 (m, 1H), 3.95 (s, 3H), 2.68-2.56 (m, 1H), 1.63-1.56 (m, 2H), 1.02 (t, 3H). MS m/z 364 [M+H]$^+$.

Example 33

1-(((2S,3S,4S)-4-fluoro-3-methyl-5-oxopyrrolidin-2-yl)methoxy)-7-methoxy-N-methylisoquinoline-6-carboxamide

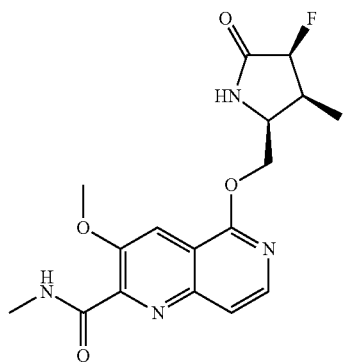

Step 1: Preparation of 1-(((2S,3S,4S)-4-fluoro-3-methyl-5-oxopyrrolidin-2-yl)methoxy)-7-methoxyisoquinoline-6-carboxylic acid

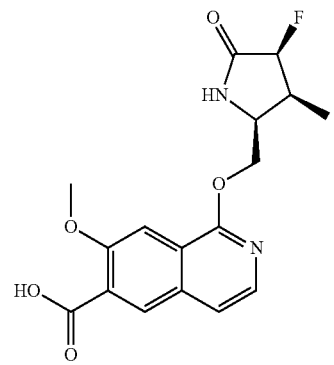 [SMILES: COc1cc2c(OC[C@H]3NC(=O)[C@@H](F)[C@H]3C)nccc2cc1C(=O)O]

1-(((2S,3S,4S)-4-fluoro-3-methyl-5-oxopyrrolidin-2-yl)methoxy)-7-methoxyisoquinoline-6-carboxamide (250 mg, 0.72 mmol) was dissolved in TFA (5 mL) at room temperature then cooled to 0° C. After 5 min, the mixture was treated with NaNO$_2$ (497 mg, 7.20 mmol) and stirred for 15 min. The reaction mixture was poured into a beaker of ice water (60 g) with stirring. The aqueous layer was extracted with EtOAc (60 mL×3) and the organic layer was dried over Na$_2$SO$_4$ to afford crude 1-(((2S,3S,4S)-4-fluoro-3-methyl-5-oxopyrrolidin-2-yl)methoxy)-7-methoxyisoquinoline-6-carboxylic acid. 100% ee. (Column: Chiralpak AD-H 250×4.6 mm I.D., 5 µm Mobile phase: iso-propanol in CO2 from 5% to 40% Flow rate: 2.5 mL/min Retention Time: 7.8 min Wavelength: 220 nm MS m/e 348.8 [M+H]$^+$. This material was used without further purification in the next reaction.

Step 2: Preparation of 1-(((2S,3S,4S)-4-fluoro-3-methyl-5-oxopyrrolidin-2-yl)methoxy)-7-methoxy-N-methylisoquinoline-6-carboxamide To a solution of 1-(((2S,3S,4S)-4-fluoro-3-methyl-5-oxopyrrolidin-2-yl)methoxy)-7-methoxyisoquinoline-6-carboxylic acid (70 mg, 0.20 mmol) in DCM (4 mL) were added EDCI (62 mg, 0.32 mmol) and HOBT (46 mg, 0.34 mmol), followed by methylamine hydrochloride (41 mg, 0.60 mmol) and DIPEA (130 mg, 1.00 mmol). The pale yellow reaction mixture was stirred for 16 h at room temperature. The reaction mixture was diluted with 30 mL of EtOAc and washed with 20 mL of saturated aqueous NaHCO$_3$ solution. The biphasic mixture was filtered and washed with 3×8 mL of water and 3×6 mL of MTBE. The cake was collected and dried in vacuo to give 1-(((2S,3S,4S)-4-fluoro-3-methyl-5-oxopyrrolidin-2-yl)methoxy)-7-methoxy-N-methylisoquinoline-6-carboxamide (49 mg, 67% yield) as a white solid. $^1$H NMR (400 MHz, DMSO-d6) δ 8.76 (br. s., 1H), 8.35 (br. s., 1H), 8.12 (s, 1H), 7.91 (d, 1H), 7.71 (s, 1H), 7.43 (d, 1H), 5.03-4.82 (m, 1H), 4.57 (d, 1H), 4.33-4.22 (m, 1H), 4.04 (br. s., 1H), 3.96 (s, 3H), 2.91 (m, 1H), 2.82 (d, 3H), 1.09 (d, 3H). $^{19}$F NMR (376 MHz, DMSO-d6,) −200.80 (br. s., 1F). MS m/e 362.0 [M+H]$^+$.

Biological Activity:

IRAK4 Enzymatic DELFIA Assay, Protocol A.

This is an in vitro assay to measure IRAK4 enzymatic activity utilizing the DELFIA (Dissociation-Enhanced Lanthanide Fluorescent Immunoassay, Perkin-Elmer) platform, with the human IRAK4 FL (Full Length) construct to characterize IRAK4 inhibitor and control compounds at 600 µM ATP (K$_M$). The final amount of enzyme in the assay is 0.1 nM IRAK4 FL, final concentration of substrate is 50 nM, and final concentration of DMSO is 2.5%.

The test compound was solubilized in DMSO to a stock concentration of 30 mM. The dose response plates were prepared with a 4 mM primary compound concentration (40-fold multiple of the final in-assay concentration), and diluted in DMSO in a four-fold series for a total of 11 data points. 1 µL of the compound dilution plate is spotted into ultra-clear polypropylene, 384-well, U-bottom plates (Corning Life Sciences).

To begin the assay, 19 µL of reaction mixture containing 20 mM HEPES pH=7.5, 5 mM MgCl$_2$, 0.0025% Brij-35, 600 µM ATP, 0.21 nM Full-length phosphorylated recombinant human IRAK4 (GenBank ID AF445802) are aliquoted into the polypropylene, 384-well, U-bottom plates containing 1 µL of test compound, mixed briefly and incubated for 20 minutes at room temperature (RT). Then, 20 µL of 20 mM HEPES pH=7.5, 5 mM MgCl$_2$, 0.0025% Brij-35, 600 µM ATP, and 100 nM ERM-biotinylated peptide (AGAGRDKYKTLRQIR) is added to start the reaction. The reaction is incubated for 60 minutes at RT and stopped by the addition of 20 µL 0.3M EDTA.

50 µL of the reaction mixture was transferred to a streptavidin-coated detection plate (DELFIA streptavidin coated plates, 384-well, white plates, Perkin-Elmer Life Sciences) and incubated for 30 minutes at RT. The plates were washed 4× with 75 µL per well of PBS containing 0.05% Tween-20. Plates were then incubated with 50 µL per well of antibody cocktail of Anti-pERM antibody at 0.125 µg/mL (Cell Signaling Technology), plus Anti-Rabbit IgG EuN1 at 0.25 µg/ml (Perkin-Elmer Life Sciences) in a solution of 10 mM MOPS pH=7.5, 150 mM NaCl, 0.05% Tween-20, 0.02% NaN$_3$, 1% BSA, 0.1% Gelatin for 45 minutes. The plates were then washed as before. 50 µL per well of DELFIA Enhancement Solution (Perkin-Elmer Life Sciences) was added to the plate and incubated for 15 minutes at RT prior to being read on an Envision Model 2104 multi-label reader using a 340 nm excitation wavelength and a 665 nm emission wavelength for detection.

IRAK4 Enzymatic DELFIA Assay, Protocol B.

This is an in vitro assay to measure IRAK4 enzymatic activity utilizing the DELFIA (Dissociation-Enhanced Lanthanide Fluorescent Immunoassay, Perkin-Elmer) platform, with inactive, unphosphorylated (0-phos), human IRAK4 FL (Full Length) construct to characterize IRAK4 inhibitor and control compounds at 600 µM ATP (K$_M$). The final amount of enzyme in the assay is 0.1 nM inactive, 0-phos, IRAK4 FL, final concentration of substrate is 50 nM, and final concentration of DMSO is 2.5%.

The test compound is solubilized in DMSO to a stock concentration of 30 mM. The dose response plates were prepared with a 4 mM primary compound concentration, serialized in DMSO and spotted (1 µL) into 384-well polypropylene plates as before.

To begin the assay, 19 uL of reaction mixture containing 20 mM HEPES pH=7.5, 5 mM MgCl$_2$, 0.0025% Brij-35, 600 uM ATP, 0.21 nM inactive, 0-phos, full-length recombinant human IRAK4 (GenBank ID AF445802) were aliquoted into the polypropylene plates containing 1 µL of test compound as before. 20 uL of 20 mM HEPES pH=7.5, 5 mM MgCl$_2$, 0.0025% Brij-35, 600 µM ATP, and 100 nM ERM-biotinylated peptide (AGAGRDKYKTLRQIR) was added to start the reaction, which was run for 90 minutes at RT and stopped by the addition of 20 µL 0.3M EDTA.

50 µL of the reaction mixture was transferred to a streptavidin-coated detection plate (DELFIA streptavidin coated plates, 384-well, white plates, Perkin-Elmer Life Sciences) and incubated for 30 minutes at RT. The plates were washed 4× with 75 µL per well of PBS containing 0.05% Tween-20. Plates were then incubated with 50 µL per well of antibody cocktail of Anti-pERM antibody at 0.125 µg/mL (Cell Signaling Technology), plus Anti-Rabbit IgG EuN1 at 0.25 µg/ml (Perkin-Elmer Life Sciences) in a solution of 10 mM MOPS pH=7.5, 150 mM NaCl, 0.05% Tween-20, 0.02% NaN$_3$, 1% BSA, 0.1% Gelatin for 45 minutes. The plates were then washed as before. 50 µL per well of DELFIA Enhancement Solution (Perkin-Elmer Life Sciences) was added to the plate and incubated for 15 minutes at RT prior to being read on an Envision Model 2104 multi-label reader using a 340 nm excitation wavelength and a 665 nm emission wavelength for detection.

TABLE 1

| Example No. | Delfia Protocol A IRAK4 IC50 (nM) | Delfia Protocol B IRAK4 IC50 (nM) | IUPAC NAME |
|---|---|---|---|
| 1 | 7.5 | 2 | 8-{[(2S,3S,4S)-3-ethyl-4-fluoro-5-oxopyrrolidin-2-yl]methoxy}-2-methoxyquinoline-3-carboxamide |
| 2 | 188 | 4 | 4-(1,3-oxazol-2-yl)-1-{[(2S)-5-oxopyrrolidin-2-yl]methoxy}-7-(propan-2-yloxy)isoquinoline-6-carboxamide |
| 3 | 2900 | 230 | 4-(4-methyl-1H-imidazol-2-yl)-1-{[(2S)-5-oxopyrrolidin-2-yl]methoxy}-7-(propan-2-yloxy)isoquinoline-6-carboxamide |
| 4 | 112 | 10 | 4-(1-methyl-1H-pyrazol-3-yl)-1-{[(2S)-5-oxopyrrolidin-2-yl]methoxy}-7-(propan-2-yloxy)isoquinoline-6-carboxamide |
| 5 | 3.7 | 1.1 | 4-(1-methyl-1H-pyrazol-4-yl)-1-{[(2S)-5-oxopyrrolidin-2-yl]methoxy}-7-(propan-2-yloxy)isoquinoline-6-carboxamide |
| 6 | 227 | 3.0 | 4-(4-methyl-1,3-oxazol-2-yl)-1-{[(2S)-5-oxopyrrolidin-2-yl]methoxy}-7-(propan-2-yloxy)isoquinoline-6-carboxamide |
| 7 | 57 | 3.2 | 4-(4,5-dimethyl-1,3-oxazol-2-yl)-1-{[(2S)-5-oxopyrrolidin-2-yl]methoxy}-7-(propan-2-yloxy)isoquinoline-6-carboxamide |
| 8 | 2100 | 190 | 4[4-(hydroxymethyl)-1H-imidazol-2-yl]-1-{[(2S)-5-oxopyrrolidin-2-yl]methoxy}-7-(propan-2-yloxy)isoquinoline-6-carboxamide |
| 9 | 89 | 4.3 | 4-(5-methyl-1,3-oxazol-2-yl)-1-{[(2S)-5-oxopyrrolidin-2-yl]methoxy}-7-(propan-2-yloxy)isoquinoline-6-carboxamide |
| 10 | >100000 | 5700 | 1-{[(2S,3R)-3-ethyl-5-oxopyrrolidin-2-yl]methoxy}-4-[(phenylsulfonyl)amino]-7-(propan-2-yloxy)isoquinoline-6-carboxamide |
| 11 | >100000 | 1300 | 1-{[(2S,3R)-3-ethyl-5-oxopyrrolidin-2-yl]methoxy}-7-(propan-2-yloxy)-4-[(pyridin-3-ylsulfonyl)amino]isoquinoline-6-carboxamide |
| 12 | >100000 | 6500 | 1-{[(2S,3R)-3-ethyl-5-oxopyrrolidin-2-yl]methoxy}-4-[(1H-imidazol-4-ylsulfonyl)amino]-7-(propan-2-yloxy)isoquinoline-6-carboxamide |
| 13 | >100000 | 12000 | 1-{[(2S,3R)-3-ethyl-5-oxopyrrolidin-2-yl]methoxy}-4-{[(1-methyl-1H-imidazol-4-Asulfonyl]aminol-7-(propan-2-yloxy)isoquinoline-6-carboxamide |
| 14 | 29000 | 15000 | 4-{[(1,2-dimethyl-1H-imidazol-4-Asulfonyl]aminol-1-{[(2S,3R)-3-ethyl-5-oxopyrrolidin-2-yl]methoxy}-7-(propan-2-yloxy)isoquinoline-6-carboxamide |
| 15 | 2.2 | 0.5 | 4-amino-1-{[(2S,3S,4S)-3-ethyl-4-fluoro-5-oxopyrrolidin-2-yl]methoxy}-7-methoxyisoquinoline-6-carboxamide |
| 16 | 4500 | 390 | 1-{[(4R,7S)-7-fluoro-6-oxo-5-azaspiro[2.4]hept-4-yl]methoxy}-7-(propan-2-yloxy)isoquinoline-6-carboxamide |
| 17 | 20.7 | 1.2 | 1-{[(4S)-7-fluoro-6-oxo-5-azaspiro[2.4]hept-4-yl]methoxy}-7-(propan-2-yloxy)isoquinoline-6-carboxamide |
| 18 | 16000 | 870 | 1-{[(4R,7R)-7-fluoro-6-oxo-5-azaspiro[2.4]hept-4-yl]methoxy}-7-(propan-2-yloxy)isoquinoline-6-carboxamide |
| 19 | 5.4 | 0.6 | 1-(((4S,7S)-7-fluoro-6-oxo-5-azaspiro[2.4]heptan-4-yl)methoxy)-7-isopropoxyisoquinoline-6-carboxamide |
| 21 | 38.5 | 21 | 1-{[(4S,7R)-7-fluoro-6-oxo-5-azaspiro[2.4]hept-4-yl]methoxy}-7-methoxyisoquinoline-6-carboxamide |
| 22 | 26000 | 1700 | 1-{[(4R,7S)-7-fluoro-6-oxo-5-azaspiro[2.4]hept-4-yl]methoxy}-7-methoxyisoquinoline-6-carboxamide |
| 23 | 1450 | 110 | 1-{[(4R,7R)-7-fluoro-6-oxo-5-azaspiro[2.4]hept-4-yl]methoxy}-7-methoxyisoquinoline-6-carboxamide |
| 24 | 5.2 | 0.8 | 1-{[(4S,7S)-7-fluoro-6-oxo-5-azaspiro[2.4]hept-4-yl]methoxy}-7-methoxyisoquinoline-6-carboxamide |
| 25 | 47 | 2.7 | 4-{[(2S,3R)-3-ethyl-5-oxopyrrolidin-2-yl]methoxy}-6-methoxyisoquinoline-7-carboxamide |
| 26 | 7.7 | 0.3 | 4-{[(2S,3S,4S)-3-ethyl-4-fluoro-5-oxopyrrolidin-2-yl]methoxy}-6-methoxyisoquinoline-7-carboxamide |
| 27 | 0.8 | 0.1 | 5-{[(2S,3S,4S)-3-ethyl-4-fluoro-5-oxopyrrolidin-2-yl]methoxy}-3-methoxynaphthalene-2-carboxamide |
| 28 | 1900 | NT | (3S,6R)-5-oxo-2,3,4,5,6,7,9,10-octahydro-12,14-(ethanediylidene)-3,6-methanopyrido[2,3-l][1,4,11,8]trioxazacyclopentadecine-19-carboxamide |
| 29 | 4200 | 350 | 7-methoxy-1-[(3-oxo-2-azabicyclo[3.1.0]hex-1-yl)methoxy]isoquinoline-6-carboxamide |
| 30 | 4300 | 151 | 7-methoxy-1-{[(1S,5S)-3-oxo-2-azabicyclo[3.1.0]hex-1-yl]methoxyisoquinoline-6-carboxamide |
| 31 | >100000 | 1200.0 | 7-methoxy-1-{[(1R,5R)-3-oxo-2-azabicyclo[3.1.0]hex-1-yl]methoxyisoquinoline-6-carboxamide |
| 32 | 27 | 4.5 | 5-{[(2S,3S,4S)-3-ethyl-4-fluoro-5-oxopyrrolidin-2-yl]methoxy}-3-methoxy-1,6-naphthyridine-2-carboxamide |
| 33 | NT | 2000 | 1-{[(2S,3S,4S)-4-fluoro-3-methyl-5-oxopyrrolidin-2-yl]methoxy}-7-methoxy-N-methylisoquinoline-6-carboxamide |

We claim:
1. A compound of Formula IIc, IIe, IIf, IIg, IIh, IIi, III, IIm, IIn, IIo, IIp, IIq, IIr, IIs, IIt, IIu, IIv, or IIx:
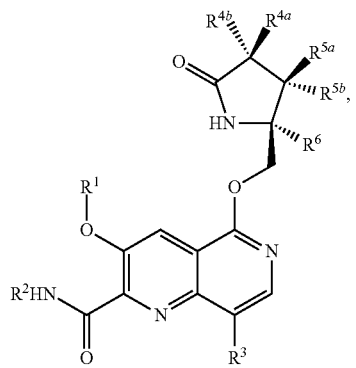
IIc
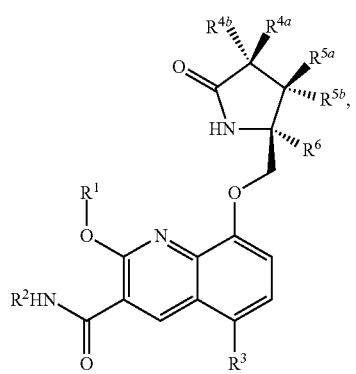
IIe
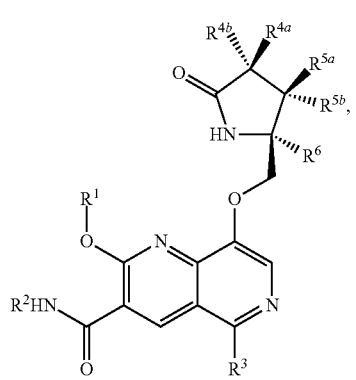
IIf
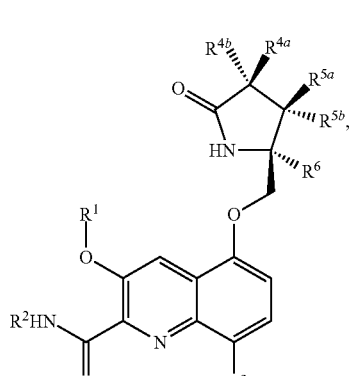
IIg
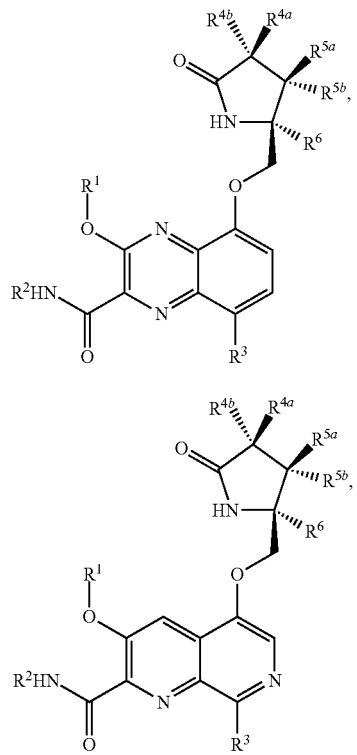
IIh
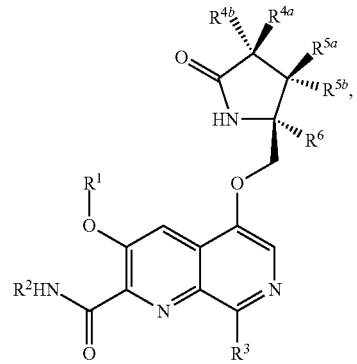
IIi
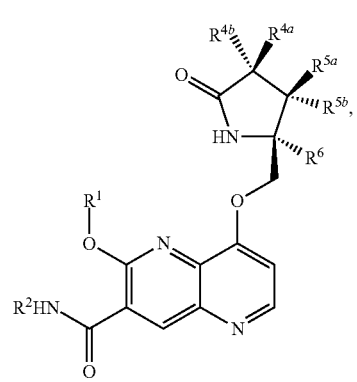
III
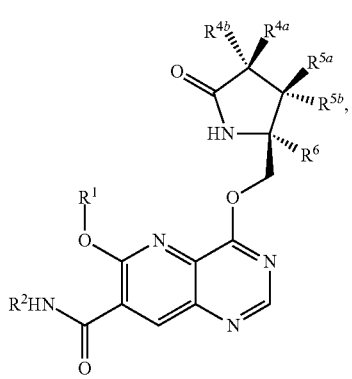
IIm

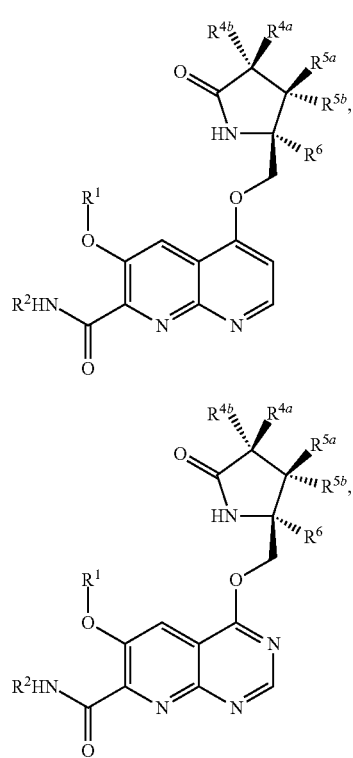
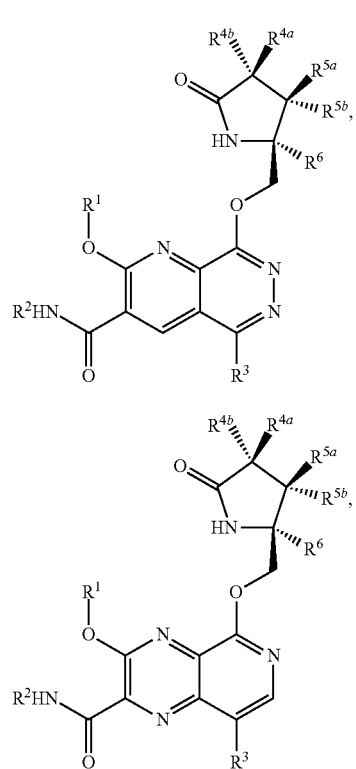
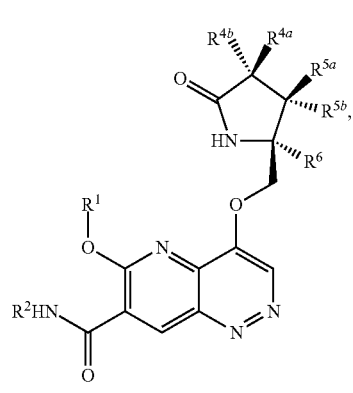
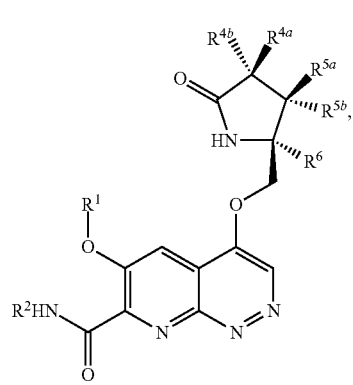
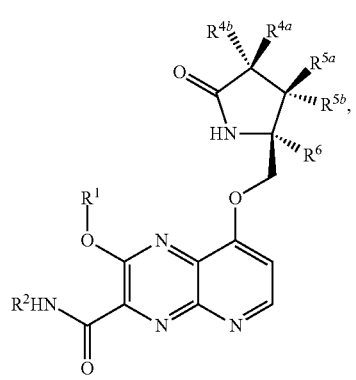

141

-continued

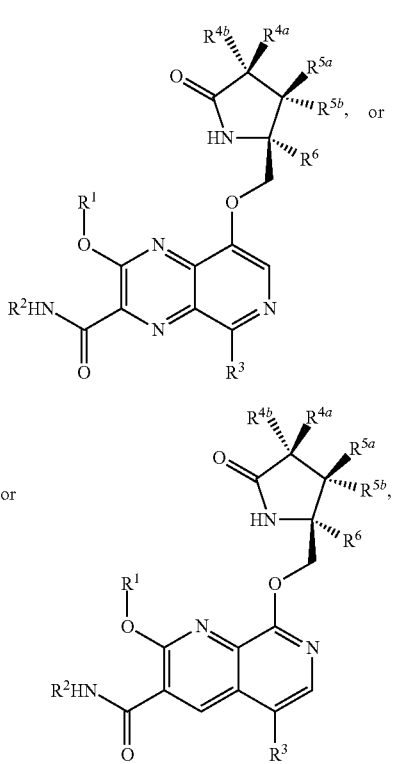

IIv or

IIx wherein
R¹ is C₁-C₆alkyl or —(C₁-C₆alkyl)ₙ(C₁-C₆cycloalkyl), wherein the alkyl or cycloalkyl is optionally substituted with deuterium, halogen, CN, OH, or C₁-C₆ alkoxy;
R² is hydrogen;
R³ is hydrogen, deuterium, halogen, nitrile, —(CH₂)ₜNR⁸ᵃR⁸ᵇ, —(CH₂)ₜ(6- to 10-membered aryl) or a —(CH₂)ₜ(5- to 10-membered heteroaryl), having one to three heteroatoms selected from N, O or S, wherein said aryl or heteroaryl is optionally substituted by one to three C₁-C₆alkyl, deuterium, halogen, CN, OH, hydroxyC₁-C₆ alkyl, or C₁-C₆ alkoxy;
R⁴ᵃ and R⁴ᵇ are each independently hydrogen, fluorine, OH, C₁-C₃ alkoxy, or CH₂OR⁷, wherein R⁷ taken together with R¹ is a C₁-C₄alkylene, optionally substituted with halogen or alkyl;
R⁵ᵃ and R⁵ᵇ are independently hydrogen, C₁-C₃ alkyl, or C₁-C₃-alkoxy, wherein said alkyl or alkoxy is optionally substituted with one to three deuterium, halogen, OH or CN; or R⁵ᵃ and R⁵ᵇ taken together with the atom to which they are bonded forms a C₃-C₇cycloalkyl or C₃-C₇heterocycloalkyl, wherein said cycloalkyl or heterocycloalkyl is optionally substituted with one to three deuterium, halogen, OH, CN or C₁-C₃alkyl;
R⁶ is hydrogen or C₁-C₃ alkyl; or R⁵ᵇ and R⁶ taken together with the atoms to which they are bonded form a C₃-C₇cycloalkyl or C₃-C₇heterocycloalkyl, wherein said cycloalkyl or heterocycloalkyl is optionally substituted with one to three deuterium, halogen, OH, CN or C₁-C₃alkyl;
R⁸ᵃ and R⁸ᵇ are each independently hydrogen, —S(O)₂R⁹ or —C(O)R⁹;
R⁹ is C₁-C₆alkyl, C₁-C₆cycloalkyl, 6- to 10-membered aryl, or a 5- to 10-membered heteroaryl, having one to three heteroatoms, wherein said alkyl, cycloalkyl, aryl

142 or heteroaryl are optionally substituted by one to three C₁-C₆alkyl, halogen, CN, OH, C₁-C₆ alkoxy or C₁-C₆ hydroxy;
n is 0 or 1;
t is 0, 1, 2 or 3;
or a pharmaceutically acceptable salt thereof.
2. The compound of claim 1 wherein
R¹ is C₁-C₆alkyl;
R² is hydrogen;
R³ is hydrogen, deuterium, —(CH₂)ₜNR⁸ᵃR⁸ᵇ, —(CH₂)ₜ(6- to 10-membered aryl) or a —(CH₂)ₜ(5- to 10-membered heteroaryl), having one to three heteroatoms selected from N, O or S, wherein said aryl or heteroaryl is optionally substituted by one to three C₁-C₆alkyl, deuterium, halogen, CN, OH, hydroxyC₁-C₆ alkyl or C₁-C₆ alkoxy;
R⁶ is hydrogen;
R⁸ᵃ and R⁸ᵇ are each independently hydrogen, —S(O)₂R⁹ or —C(O)R⁹;
R⁹ is C₁-C₆alkyl, C₁-C₆cycloalkyl, 6- to 10-membered aryl, or a 5- to 10-membered heteroaryl, having one to three heteroatoms, wherein said alkyl, cycloalkyl, aryl or heteroaryl are optionally substituted by one to three C₁-C₆alkyl, halogen, CN, OH, C₁-C₆ alkoxy or C₁-C₆ hydroxy; and
t is 0 or 1;
or a pharmaceutically acceptable salt thereof.
3. The compound of claim 2 wherein the aryl and heteroaryl of R³ is selected from phenyl, pyrazolyl, imidazolyl and oxazolyl, optionally substituted by one or two C₁-C₆alkyl or C₁-C₆hydroxyalkyl; or a pharmaceutically acceptable salt thereof.
4. The compound of claim 2 wherein
R³ is hydrogen, deuterium or —(CH₂)ₜNR⁸ᵃR⁸ᵇ;
R⁸ᵃ and R⁸ᵇ are each independently hydrogen or —S(O)₂R⁹;
R⁹ is C₁-C₆alkyl, C₁-C₆cycloalkyl, 6- to 10-membered aryl, or a 5- to 10-membered heteroaryl, having one to three heteroatoms, wherein said alkyl, cycloalkyl, aryl or heteroaryl are optionally substituted by one to three C₁-C₆alkyl, halogen, CN, OH, C₁-C₆ alkoxy or C₁-C₆ hydroxy; and
t is 0 or 1;
or a pharmaceutically acceptable salt thereof.
5. A compound selected from:
8-{[(2S,3S,4S)-3-ethyl-4-fluoro-5-oxopyrrolidin-2-yl]methoxy}-2-methoxyquinoline-3-carboxamide;
4-(1,3-oxazol-2-yl)-1-{[(2S)-5-oxopyrrolidin-2-yl]methoxy}-7-(propan-2-yloxy)isoquinoline-6-carboxamide;
4-(4-methyl-1H-imidazol-2-yl)-1-{[(2S)-5-oxopyrrolidin-2-yl]methoxy}-7-(propan-2-yloxy)isoquinoline-6-carboxamide;
4-(1-methyl-1H-pyrazol-3-yl)-1-{[(2S)-5-oxopyrrolidin-2-yl]methoxy}-7-(propan-2-yloxy)isoquinoline-6-carboxamide;
4-(1-methyl-1H-pyrazol-4-yl)-1-{[(2S)-5-oxopyrrolidin-2-yl]methoxy}-7-(propan-2-yloxy)isoquinoline-6-carboxamide;
4-(4-methyl-1,3-oxazol-2-yl)-1-{[(2S)-5-oxopyrrolidin-2-yl]methoxy}-7-(propan-2-yloxy)isoquinoline-6-carboxamide;
4-(4,5-dimethyl-1,3-oxazol-2-yl)-1-{[(2S)-5-oxopyrrolidin-2-yl]methoxy}-7-(propan-2-yloxy)isoquinoline-6-carboxamide;

4-[4-(hydroxymethyl)-1H-imidazol-2-yl]-1-{[(2S)-5-oxopyrrolidin-2-yl]methoxy}-7-(propan-2-yloxy)isoquinoline-6-carboxamide;

4-(5-methyl-1,3-oxazol-2-yl)-1-{[(2S)-5-oxopyrrolidin-2-yl]methoxy}-7-(propan-2-yloxy)isoquinoline-6-carboxamide;

1-{[(2S,3R)-3-ethyl-5-oxopyrrolidin-2-yl]methoxy}-4-[(phenylsulfonyl)amino]-7-(propan-2-yloxy)isoquinoline-6-carboxamide;

1-{[(2S,3R)-3-ethyl-5-oxopyrrolidin-2-yl]methoxy}-7-(propan-2-yloxy)-4-[(pyridin-3-ylsulfonyl)amino]isoquinoline-6-carboxamide;

1-{[(2S,3R)-3-ethyl-5-oxopyrrolidin-2-yl]methoxy}-4-[(1H-imidazol-4-ylsulfonyl)amino]-7-(propan-2-yloxy)isoquinoline-6-carboxamide;

1-{[(2S,3R)-3-ethyl-5-oxopyrrolidin-2-yl]methoxy}-4-{[(1-methyl-1H-imidazol-4-yl)sulfonyl]amino}-7-(propan-2-yloxy)isoquinoline-6-carboxamide;

4-{[(1,2-dimethyl-1H-imidazol-4-yl)sulfonyl]amino}-1-{[(2S,3R)-3-ethyl-5-oxopyrrolidin-2-yl]methoxy}-7-(propan-2-yloxy)isoquinoline-6-carboxamide;

4-amino-1-{[(2S,3S,4S)-3-ethyl-4-fluoro-5-oxopyrrolidin-2-yl]methoxy}-7-methoxyisoquinoline-6-carboxamide;

1-{[(4R,7S)-7-fluoro-6-oxo-5-azaspiro[2.4]hept-4-yl]methoxy}-7-(propan-2-yloxy)isoquinoline-6-carboxamide;

1-{[(4S)-7-fluoro-6-oxo-5-azaspiro[2.4]hept-4-yl]methoxy}-7-(propan-2-yloxy)isoquinoline-6-carboxamide;

1-{[(4R,7R)-7-fluoro-6-oxo-5-azaspiro[2.4]hept-4-yl]methoxy}-7-(propan-2-yloxy)isoquinoline-6-carboxamide;

1-(((4S,7R)-7-fluoro-6-oxo-5-azaspiro[2.4]heptan-4-yl)methoxy)-7-isopropoxyisoquinoline-6-carboxamide;

1-{[(4S,7R)-7-fluoro-6-oxo-5-azaspiro[2.4]hept-4-yl]methoxy}-7-methoxyisoquinoline-6-carboxamide;

1-{[(4R,7S)-7-fluoro-6-oxo-5-azaspiro[2.4]hept-4-yl]methoxy}-7-methoxyisoquinoline-6-carboxamide;

1-{[(4R,7R)-7-fluoro-6-oxo-5-azaspiro[2.4]hept-4-yl]methoxy}-7-methoxyisoquinoline-6-carboxamide;

1-{[(4S,7S)-7-fluoro-6-oxo-5-azaspiro[2.4]hept-4-yl]methoxy}-7-methoxyisoquinoline-6-carboxamide;

4-{[(2S,3R)-3-ethyl-5-oxopyrrolidin-2-yl]methoxy}-6-methoxyisoquinoline-7-carboxamide;

4-{[(2S,3S,4S)-3-ethyl-4-fluoro-5-oxopyrrolidin-2-yl]methoxy}-6-methoxyisoquinoline-7-carboxamide;

5-{[(2S,3S,4S)-3-ethyl-4-fluoro-5-oxopyrrolidin-2-yl]methoxy}-3-methoxynaphthalene-2-carboxamide;

(3S,6R)-5-oxo-2,3,4,5,6,7,9,10-octahydro-12,14-(ethanediylidene)-3,6-methanopyrido[2,3-l][1,4,11,8]trioxazacyclopentadecine-19-carboxamide;

7-methoxy-1-[(3-oxo-2-azabicyclo[3.1.0]hex-1-yl)methoxy]isoquinoline-6-carboxamide;

7-methoxy-1-{[(1S,5S)-3-oxo-2-azabicyclo[3.1.0]hex-1-yl]methoxy}isoquinoline-6-carboxamide;

7-methoxy-1-{[(1R,5R)-3-oxo-2-azabicyclo[3.1.0]hex-1-yl]methoxy}isoquinoline-6-carboxamide;

5-{[(2S,3S,4S)-3-ethyl-4-fluoro-5-oxopyrrolidin-2-yl]methoxy}-3-methoxy-1,6-naphthyridine-2-carboxamide; and 1-{[(2S,3S,4S)-4-fluoro-3-methyl-5-oxopyrrolidin-2-yl]methoxy}-7-methoxy-N-methylisoquinoline-6-carboxamide;

or pharmaceutically acceptable salts thereof.

6. A pharmaceutical composition comprising a compound of claim 5, or a pharmaceutically acceptable salt thereof, and at least one pharmaceutically acceptable vehicle, diluent or carrier.

7. A pharmaceutical combination comprising a therapeutically effective amount:
a first compound; a second compound; and a pharmaceutically acceptable carrier, vehicle, or diluent; wherein
the first compound is a compound of claim 5 or a pharmaceutically acceptable salt thereof;
the second compound is selected from the group consisting of a corticosteroid, hydroxychloroquine, cyclophosphamide, azathioprine, mycophenolate mofetil, methotrexate, Janus kinase inhibitor, statin, calcipotriene, angiotensin-converting enzyme inhibitor and angiotensin receptor blocker.

8. The combination of claim 7 wherein the second compound is a janus kinase inhibitor.

9. The combination of claim 8 wherein the janus kinase inhibitor is selected from ruxolitinib, baricitinib, tofacitinib, Decernotinib, Cerdulatinib, JTE-052, Peficitinib, GLPG-0634, INCB-47986, INCB-039110, PF-04965842, XL-019, ABT-494, R-348, GSK-2586184, AC-410, BMS-911543 and PF-06263276.

10. A method of treating a disease selected from systemic lupus erythematosus (SLE), lupus nephritis, rheumatoid arthritis, psoriasis, or atopic dermatitis, in a human comprising administering to the human having said disease a therapeutically effective amount of a compound of claim 5, or a pharmaceutically acceptable salt thereof.

* * * * *